US010640549B2

United States Patent
Derewenda et al.

(10) Patent No.: US 10,640,549 B2
(45) Date of Patent: May 5, 2020

(54) RECOMBINANT ANTIBODIES THAT RECOGNIZE THE C-TERMINAL DOMAINS OF EBOLA VIRUS NUCLEOPROTEIN

(71) Applicants: UNIVERSITY OF VIRGINIA PATENT FOUNDATION, Charlottesville, VA (US); THE UNIVERSITY OF CHICAGO, Chicago, IL (US)

(72) Inventors: Zygmunt S. Derewenda, Charlottesville, VA (US); Daniel A. Engel, Charlottesville, VA (US); Anthony Kossiakoff, Chicago, IL (US); Elena K. Davydova, Chicago, IL (US); Mateusz Jaskolowski, Kargoszyn (PL)

(73) Assignees: University of Virginia Patent Foundation, Charlottesville, VA (US); The University of Chicago, Chicago, IL (US)

( * ) Notice: Subject to any disclaimer, the term of this patent is extended or adjusted under 35 U.S.C. 154(b) by 19 days.

(21) Appl. No.: 15/518,417

(22) PCT Filed: Oct. 16, 2015

(86) PCT No.: PCT/US2015/056017
§ 371 (c)(1),
(2) Date: Apr. 11, 2017

(87) PCT Pub. No.: WO2016/061504
PCT Pub. Date: Apr. 21, 2016

(65) Prior Publication Data
US 2018/0334494 A1    Nov. 22, 2018

Related U.S. Application Data

(60) Provisional application No. 62/065,392, filed on Oct. 17, 2014.

(51) Int. Cl.
| | | |
|---|---|---|
| C07K 16/10 | (2006.01) | |
| C12Q 1/70 | (2006.01) | |
| A61K 39/42 | (2006.01) | |
| G01N 33/569 | (2006.01) | |

(52) U.S. Cl.
CPC ............ *C07K 16/10* (2013.01); *A61K 39/42* (2013.01); *C12Q 1/701* (2013.01); *G01N 33/56983* (2013.01); *C07K 2317/24* (2013.01); *C07K 2317/33* (2013.01); *C07K 2317/55* (2013.01); *C07K 2317/56* (2013.01); *C07K 2317/565* (2013.01); *C07K 2317/92* (2013.01); *C12N 2760/14111* (2013.01); *C12N 2760/14122* (2013.01); *G01N 2333/08* (2013.01)

(58) Field of Classification Search
CPC .............. C07K 16/10; C07K 2317/565; C07K 2317/56; C07K 2317/24; C07K 2317/33; C07K 2317/55; A61K 39/42; C12N 2760/14111; C12N 2760/14122
See application file for complete search history.

(56) References Cited

U.S. PATENT DOCUMENTS

2012/0251502 A1    10/2012  Towner et al.

FOREIGN PATENT DOCUMENTS

| WO | WO2008/143679 | 11/2008 |
|---|---|---|
| WO | WO2012/064836 | 5/2012 |
| WO | WO2012/106490 | 8/2012 |
| WO | WO2013/184218 | 12/2018 |

OTHER PUBLICATIONS

Dziubanska, P. J., et al., 2014, The structure of the C-terminal domain of the Zaire ebolavirus nucleoprotein, Acta Cryst. D70:2420-2429.*
Sela-Culang, I., et al., Oct. 2013, The structural basis of antibody-antigen recognition, Front. Immunol. 4:article 302, 1-13.*
Nikoloudis, D., et al., 2014, A complete, multi-level conformational clustering of antibody complementarity-determining regions, PeerJ 2e:456; DOI 10.7717/peerj.456, pp. 1-40.*
Xiang, J., et al., 1999, Light-chain framework region residue Tyr71 of chimeric B72.3 antibody plays an important role in influencing the TAG72 antigen binding, Prot. Engineer. 12(5):417-421.*
Winkler, K., et al., 2000, Changing the antigen binding specificity by single point mutations of an anti-p24 (HIV-1) antibody, J. Immunol. 165:4505-4514.*
Liu, Z., et al., 1999, Fine mapping of the antigen-antibody interaction of scFv215, a recombinant antibody inhibiting RNA polymerase II from *Drosophila melanogaster*, J. Mol. Recog. 12:103-111.*
PCT Search Report and Written Opinion for PCT/US2015/056017, completed Mar. 16, 2016.
Changula, Katendi, et al.; Mapping of Conserved and Species-Specific Antibody Epitopes on the Ebola Virus Nucleoprotein; 2013; Virus Research; vol. 176; pp. 83-90.
Dziubanska, Paulina J., et al.; The Structure of the C-Terminal Domain of the Zaire Ebolavirus Nucleoprotein; 2014; Acta. Cryst.; vol. D70; pp. 2420-2429.

(Continued)

*Primary Examiner* — Jeffrey S Parkin
(74) *Attorney, Agent, or Firm* — Barnes & Thornburg LLP

(57) ABSTRACT

This disclosure is directed to compositions and methods for utilizing the boundaries of the C-terminal domains of Nucleoprotein from Zaire Ebola virus as highly stable recombinant protein antigens to generate antibodies for diagnosis and treatment of Ebola virus infection.

12 Claims, 15 Drawing Sheets

Specification includes a Sequence Listing.

(56) References Cited

OTHER PUBLICATIONS

Kamata, Teddy, et al.; Determination of Specific Antibody Responses to the Six Species of Ebola and Marburg Viruses by Multiplexed Protein Microarrays; Dec. 2014; Clinical and Vaccine Immunology; vol. 21; No. 12; pp. 1605-1612.

* cited by examiner

PREDICTED EPITOPE

FAB20

>HEAVY CHAIN SEQUENCE-SEQ ID NO: 212

HC1-CDR #11; SEQ ID NO: 43
EISEVQLVESGGGLVQPGGSLRLSCAASGFNISYSSIHWVRQAPGKGLEWVASIYSYSGYTSYADSVKGR
HC2-CDR #99; SEQ ID NO: 96

HC3-CDR #188; SEQ ID NO: 145
FTISADTSKNTAYLQMNSLRAEDTAVYYCARSYWYHVGSWHYTGMDYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHT

*FIG. 9A*

FAB20

>LIGHT CHAIN SEQUENCE-SEQ ID NO: 213
SDIQMTQSPSSLSASVGDRVTITCRASQSVSSAVAWYQQKPGKAPKLLIYSASSLYSGVPSRFSGSRSGT
LC3-CDR #234; SEQ ID NO: 35
DFTLTISSLQPEDFATYYCQQSSSSLITFGQGTKVEIKRTVAAPSVFIFPPSDSQLKSGTASVVCLLNNFYPRE
AKVQWKVDNALQSGNSQESVTEQDSKDSTYSLSSTLTLSKADYEKHKVYACEVTHQGLSSPVTKSFNRGEC

*FIG. 9B*

FAB6

>HEAVY CHAIN SEQUENCE-SEQ ID NO: 210

HC1-CDR #32; SEQ ID NO: 105

EISEVQLVESGGGLVQPGGSLRLSCAASGFN<u>VYYYIHW</u>RQAPGKGLEWVAS<u>ISPYYGYTSSYADSVKG</u>

HC2-CDR #85; SEQ ID NO: 51

HC3-CDR #174; SEQ ID NO: 104

RFTISADTSKNTAYLQMNSLRAEDTAVYYCAR<u>WSYDQSMSYKSGMDYW</u>GQGTLVTVSSASTKGPSVFPLAPSSK
STSGGTAALGCLVKDYFPEPVTVSWNSGALTSGVHTFPAVLQSSGLYSLSSVVTVPSSSLGTQTYICNVNHKPS
NTKVDKKVEPKSCDKTHT

*FIG. 10A*

FAB6

>LIGHT CHAIN SEQUENCE-SEQ ID NO: 211

SDIQMTQSPSSLSASVGDRVTITCRASQSVSSAVAWYQQKPGKAPKLLIYSASSLYSGVPSRFSGSRSGT

LC3-CDR #245; SEQ ID NO: 106

DFTLTISSLQPEDFATYYCQQ<u>YSYSLV</u>TFGQGTKVEIKRTVAAPSVFIFPPSDSQLKSGTASVVCLLNNFYPRE
AKVQWKVDNALQSGNSQESVTEQDSKDSTYSLSSTLTLSKADYEKHKVYACEVTHQGLSSPVTKSFNRGEC

*FIG. 10B*

SEQUENCE LISTING

```
<160> NUMBER OF SEQ ID NOS: 217

<210> SEQ ID NO 1
<211> LENGTH: 103
<212> TYPE: PRT
<213> ORGANISM: Ebola virus

<400> SEQUENCE: 1

Gly Ala Met Ala Lys Pro His Ser Glu Gln Ser Val Glu Glu Met Tyr
1               5                   10                  15

Arg His Ile Leu Gln Thr Gln Gly Pro Phe Asp Ala Ile Leu Tyr Tyr
            20                  25                  30

Tyr Met Met Thr Glu Glu Pro Ile Val Phe Ser Thr Ser Asp Gly Lys
        35                  40                  45

Glu Tyr Val Tyr Pro Asp Ser Leu Glu Gly Glu His Pro Pro Trp Leu
    50                  55                  60

Ser Glu Lys Glu Ala Leu Asn Glu Asp Asn Arg Phe Ile Thr Met Asp
65                  70                  75                  80

Asp Gln Gln Phe Tyr Trp Pro Val Met Asn His Arg Asn Lys Phe Met
                85                  90                  95

Ala Ile Leu Gln His His Lys
            100

<210> SEQ ID NO 2
<211> LENGTH: 102
<212> TYPE: PRT
<213> ORGANISM: Ebola virus

<400> SEQUENCE: 2
```

```
Gly Ala Met Ala Asn Ser Lys Ser Ala Leu Glu Glu Thr Tyr
1               5                   10                  15

Tyr His Leu Leu Lys Thr Gln Gly Pro Phe Glu Ala Ile Asn Tyr Tyr
                20                  25                  30

His Leu Met Ser Asp Glu Pro Ile Ala Phe Ser Thr Glu Ser Gly Lys
                35                  40                  45

Glu Tyr Ile Phe Pro Asp Ser Leu Glu Glu Ala Tyr Pro Pro Trp Leu
            50                  55                  60

Ser Glu Lys Glu Ala Leu Gly Lys Glu Asn Arg Tyr Leu Val Ile Asp
65                  70                  75                  80

Gly Gln Gln Phe Leu Trp Pro Val Met Ser Leu Arg Asp Lys Phe Leu
                85                  90                  95

Ala Val Leu Gln His Asp
                100
```

<210> SEQ ID NO 3
<211> LENGTH: 103
<212> TYPE: PRT
<213> ORGANISM: Ebola virus

<400> SEQUENCE: 3

```
Gly Ala Met Ala Asn Ala Gln Ser Glu Gln Ser Ile Ala Glu Met Tyr
1               5                   10                  15

Gln His Ile Leu Lys Thr Gln Gly Pro Phe Asp Ala Ile Leu Tyr Tyr
                20                  25                  30

His Met Met Lys Glu Glu Pro Ile Ile Phe Ser Thr Ser Asp Gly Lys
                35                  40                  45

Glu Tyr Thr Tyr Pro Asp Ser Leu Glu Asp Glu Tyr Pro Pro Trp Leu
            50                  55                  60

Ser Glu Lys Glu Ala Met Asn Glu Asp Asn Arg Phe Ile Thr Met Asp
65                  70                  75                  80

Gly Gln Gln Phe Tyr Trp Pro Val Met Asn His Arg Asn Lys Phe Met
                85                  90                  95

Ala Ile Leu Gln His His Arg
                100
```

<210> SEQ ID NO 4
<211> LENGTH: 103
<212> TYPE: PRT
<213> ORGANISM: Ebola virus

<400> SEQUENCE: 4

```
Gly Ala Met Ala Gln Ser Lys Ser Met Gln Lys Leu Glu Glu Thr Tyr
1               5                   10                  15

His His Leu Leu Arg Thr Gln Gly Pro Phe Glu Ala Ile Asn Tyr Tyr
                20                  25                  30

His Met Met Lys Asp Glu Pro Val Ile Phe Ser Thr Asp Asp Gly Lys
                35                  40                  45

Glu Tyr Thr Tyr Pro Asp Ser Leu Glu Glu Ala Tyr Pro Pro Trp Leu
            50                  55                  60

Thr Glu Lys Glu Arg Leu Asp Lys Glu Asn Arg Tyr Ile Tyr Ile Asn
65                  70                  75                  80

Asn Gln Gln Phe Phe Trp Pro Val Met Ser Pro Arg Asp Lys Phe Leu
                85                  90                  95

Ala Ile Leu Gln His His Gln
                100
```

<210> SEQ ID NO 5
<211> LENGTH: 101
<212> TYPE: PRT
<213> ORGANISM: Ebola virus

<400> SEQUENCE: 5

Met Ala Asn Thr Gln Ser Glu His Ser Phe Glu Met Tyr Arg His
1               5                   10                  15

Ile Leu Arg Ser Gln Gly Pro Phe Asp Ala Val Leu Tyr Tyr His Met
            20                  25                  30

Met Lys Asp Glu Pro Val Val Phe Ser Thr Ser Asp Gly Lys Glu Tyr
        35                  40                  45

Thr Tyr Pro Asp Ser Leu Glu Glu Tyr Pro Pro Trp Leu Thr Glu
    50                  55                  60

Lys Glu Ala Met Asn Glu Glu Asn Arg Phe Val Thr Leu Asp Gly Gln
65                  70                  75                  80

Gln Phe Tyr Trp Pro Val Met Asn His Lys Asn Lys Phe Met Ala Ile
                85                  90                  95

Leu Gln His His Gln
            100

<210> SEQ ID NO 6
<211> LENGTH: 6
<212> TYPE: PRT
<213> ORGANISM: Homo sapiens

<400> SEQUENCE: 6

Ser Tyr Ser Trp Gly Met
1               5

<210> SEQ ID NO 7
<211> LENGTH: 6
<212> TYPE: PRT
<213> ORGANISM: Homo sapiens

<400> SEQUENCE: 7

Ile Ser Ser Tyr Ser Ile
1               5

<210> SEQ ID NO 8
<211> LENGTH: 10
<212> TYPE: PRT
<213> ORGANISM: Homo sapiens

<400> SEQUENCE: 8

Tyr Ile Ser Ser Tyr Ser Gly Tyr Thr Tyr
1               5                   10

<210> SEQ ID NO 9
<211> LENGTH: 7
<212> TYPE: PRT
<213> ORGANISM: Homo sapiens

<400> SEQUENCE: 9

Leu Ser Tyr Pro Leu Leu Ile
1               5

<210> SEQ ID NO 10
<211> LENGTH: 6
<212> TYPE: PRT
<213> ORGANISM: Homo sapiens

```
<400> SEQUENCE: 10

Tyr Ser Tyr Phe Gly Phe
1               5

<210> SEQ ID NO 11
<211> LENGTH: 5
<212> TYPE: PRT
<213> ORGANISM: Homo sapiens

<400> SEQUENCE: 11

Tyr Tyr Ser Ser Ile
1               5

<210> SEQ ID NO 12
<211> LENGTH: 10
<212> TYPE: PRT
<213> ORGANISM: Homo sapiens

<400> SEQUENCE: 12

Ser Ile Ser Ser Ser Ser Gly Tyr Thr Tyr
1               5                   10

<210> SEQ ID NO 13
<211> LENGTH: 8
<212> TYPE: PRT
<213> ORGANISM: Homo sapiens

<400> SEQUENCE: 13

Leu Tyr Trp Tyr Ser Ser Pro Ile
1               5

<210> SEQ ID NO 14
<211> LENGTH: 12
<212> TYPE: PRT
<213> ORGANISM: Homo sapiens

<400> SEQUENCE: 14

Asp Trp Lys Tyr Thr Ile Phe Ser Gly Val Gly Met
1               5                   10

<210> SEQ ID NO 15
<211> LENGTH: 10
<212> TYPE: PRT
<213> ORGANISM: Homo sapiens

<400> SEQUENCE: 15

Ser Ile Tyr Pro Tyr Tyr Gly Ser Thr Ser
1               5                   10

<210> SEQ ID NO 16
<211> LENGTH: 6
<212> TYPE: PRT
<213> ORGANISM: Homo sapiens

<400> SEQUENCE: 16

Ser Trp Tyr Pro Pro Val
1               5

<210> SEQ ID NO 17
<211> LENGTH: 13
<212> TYPE: PRT
<213> ORGANISM: Homo sapiens

<400> SEQUENCE: 17
```

Glu Tyr Lys Tyr Tyr Tyr Met Trp Gly Thr Ser Gly Ile
1               5                   10

<210> SEQ ID NO 18
<211> LENGTH: 6
<212> TYPE: PRT
<213> ORGANISM: Homo sapiens

<400> SEQUENCE: 18

Phe Ser Tyr Ser Ser Ile
1               5

<210> SEQ ID NO 19
<211> LENGTH: 10
<212> TYPE: PRT
<213> ORGANISM: Homo sapiens

<400> SEQUENCE: 19

Ser Ile Ser Ser Ser Tyr Gly Ser Thr Tyr
1               5                   10

<210> SEQ ID NO 20
<211> LENGTH: 6
<212> TYPE: PRT
<213> ORGANISM: Homo sapiens

<400> SEQUENCE: 20

Ser Trp Tyr Tyr Pro Ile
1               5

<210> SEQ ID NO 21
<211> LENGTH: 12
<212> TYPE: PRT
<213> ORGANISM: Homo sapiens

<400> SEQUENCE: 21

Gly Lys Gly Gly Met Tyr Trp Tyr Ser Ser Ala Ile
1               5                   10

<210> SEQ ID NO 22
<211> LENGTH: 6
<212> TYPE: PRT
<213> ORGANISM: Homo sapiens

<400> SEQUENCE: 22

Val Tyr Ser Ser Ser Ile
1               5

<210> SEQ ID NO 23
<211> LENGTH: 10
<212> TYPE: PRT
<213> ORGANISM: Homo sapiens

<400> SEQUENCE: 23

Ser Ile Tyr Ser Ser Tyr Gly Tyr Thr Ser
1               5                   10

<210> SEQ ID NO 24
<211> LENGTH: 6
<212> TYPE: PRT
<213> ORGANISM: Homo sapiens

<400> SEQUENCE: 24

Phe Trp Tyr Phe Pro Val
1               5

<210> SEQ ID NO 25
<211> LENGTH: 14
<212> TYPE: PRT
<213> ORGANISM: Homo sapiens

<400> SEQUENCE: 25

Gly Arg Trp Gly Tyr Tyr Asp Phe Tyr Val Pro Arg Gly Phe
1               5                   10

<210> SEQ ID NO 26
<211> LENGTH: 6
<212> TYPE: PRT
<213> ORGANISM: Homo sapiens

<400> SEQUENCE: 26

Val Ser Tyr Ser Ser Ile
1               5

<210> SEQ ID NO 27
<211> LENGTH: 10
<212> TYPE: PRT
<213> ORGANISM: Homo sapiens

<400> SEQUENCE: 27

Ser Ile Tyr Ser Ser Tyr Gly Ser Thr Tyr
1               5                   10

<210> SEQ ID NO 28
<211> LENGTH: 6
<212> TYPE: PRT
<213> ORGANISM: Homo sapiens

<400> SEQUENCE: 28

Ser Trp Tyr Asn Pro Leu
1               5

<210> SEQ ID NO 29
<211> LENGTH: 13
<212> TYPE: PRT
<213> ORGANISM: Homo sapiens

<400> SEQUENCE: 29

Leu Asp Tyr Ala Tyr Pro Trp Trp Phe Asn Asn Ala Met
1               5                   10

<210> SEQ ID NO 30
<211> LENGTH: 10
<212> TYPE: PRT
<213> ORGANISM: Homo sapiens

<400> SEQUENCE: 30

Tyr Ile Tyr Pro Tyr Ser Gly Ser Thr Ser
1               5                   10

<210> SEQ ID NO 31
<211> LENGTH: 6
<212> TYPE: PRT
<213> ORGANISM: Homo sapiens

<400> SEQUENCE: 31

Tyr Trp Ser Phe Pro Val
1               5

<210> SEQ ID NO 32
<211> LENGTH: 12
<212> TYPE: PRT
<213> ORGANISM: Homo sapiens

<400> SEQUENCE: 32

Pro Pro Tyr Lys Trp Ser Lys Ser Tyr Tyr Gly Met
1               5                   10

<210> SEQ ID NO 33
<211> LENGTH: 6
<212> TYPE: PRT
<213> ORGANISM: Homo sapiens

<400> SEQUENCE: 33

Val Tyr Tyr Tyr Ser Ile
1               5

<210> SEQ ID NO 34
<211> LENGTH: 10
<212> TYPE: PRT
<213> ORGANISM: Homo sapiens

<400> SEQUENCE: 34

Ser Ile Ser Ser Ser Ser Gly Ser Thr Ser
1               5                   10

<210> SEQ ID NO 35
<211> LENGTH: 6
<212> TYPE: PRT
<213> ORGANISM: Homo sapiens

<400> SEQUENCE: 35

Ser Ser Ser Ser Leu Ile
1               5

<210> SEQ ID NO 36
<211> LENGTH: 11
<212> TYPE: PRT
<213> ORGANISM: Homo sapiens

<400> SEQUENCE: 36

Gln Ser Thr Gly Tyr Trp Trp Ser Trp Gly Ile
1               5                   10

<210> SEQ ID NO 37
<211> LENGTH: 6
<212> TYPE: PRT
<213> ORGANISM: Homo sapiens

<400> SEQUENCE: 37

Ser Met Met Tyr Pro Ile
1               5

<210> SEQ ID NO 38
<211> LENGTH: 12
<212> TYPE: PRT
<213> ORGANISM: Homo sapiens

<400> SEQUENCE: 38

Ser Arg Met Trp Ser Gln Tyr Tyr Tyr Gly Met
1               5                   10

<210> SEQ ID NO 39

```
<211> LENGTH: 6
<212> TYPE: PRT
<213> ORGANISM: Homo sapiens

<400> SEQUENCE: 39

Ile Ser Ser Ser Ser Ile
1               5

<210> SEQ ID NO 40
<211> LENGTH: 10
<212> TYPE: PRT
<213> ORGANISM: Homo sapiens

<400> SEQUENCE: 40

Ser Ile Tyr Ser Tyr Tyr Gly Tyr Thr Ser
1               5                   10

<210> SEQ ID NO 41
<211> LENGTH: 6
<212> TYPE: PRT
<213> ORGANISM: Homo sapiens

<400> SEQUENCE: 41

Ser Trp Gly Ser Leu Leu
1               5

<210> SEQ ID NO 42
<211> LENGTH: 13
<212> TYPE: PRT
<213> ORGANISM: Homo sapiens

<400> SEQUENCE: 42

Ser Arg Ser Tyr Gly Trp Tyr Tyr Pro Ser Gln Ala Met
1               5                   10

<210> SEQ ID NO 43
<211> LENGTH: 6
<212> TYPE: PRT
<213> ORGANISM: Homo sapiens

<400> SEQUENCE: 43

Ile Ser Tyr Ser Ser Ile
1               5

<210> SEQ ID NO 44
<211> LENGTH: 10
<212> TYPE: PRT
<213> ORGANISM: Homo sapiens

<400> SEQUENCE: 44

Tyr Ile Ser Pro Tyr Tyr Gly Ser Thr Ser
1               5                   10

<210> SEQ ID NO 45
<211> LENGTH: 6
<212> TYPE: PRT
<213> ORGANISM: Homo sapiens

<400> SEQUENCE: 45

Val Trp Trp Trp Pro Ile
1               5

<210> SEQ ID NO 46
<211> LENGTH: 12
<212> TYPE: PRT
```

<213> ORGANISM: Homo sapiens

<400> SEQUENCE: 46

Ser Tyr Pro Trp Phe Tyr Lys Tyr Trp Phe Ala Ile
1               5                   10

<210> SEQ ID NO 47
<211> LENGTH: 10
<212> TYPE: PRT
<213> ORGANISM: Homo sapiens

<400> SEQUENCE: 47

Ser Ile Ser Ser Tyr Tyr Gly Ser Thr Tyr
1               5                   10

<210> SEQ ID NO 48
<211> LENGTH: 6
<212> TYPE: PRT
<213> ORGANISM: Homo sapiens

<400> SEQUENCE: 48

Tyr Trp Gly Ser Leu Ile
1               5

<210> SEQ ID NO 49
<211> LENGTH: 13
<212> TYPE: PRT
<213> ORGANISM: Homo sapiens

<400> SEQUENCE: 49

Thr His Tyr Trp His Phe Gly His Pro Tyr Tyr Gly Phe
1               5                   10

<210> SEQ ID NO 50
<211> LENGTH: 6
<212> TYPE: PRT
<213> ORGANISM: Homo sapiens

<400> SEQUENCE: 50

Ile Tyr Ser Ser Ser Ile
1               5

<210> SEQ ID NO 51
<211> LENGTH: 10
<212> TYPE: PRT
<213> ORGANISM: Homo sapiens

<400> SEQUENCE: 51

Ser Ile Ser Pro Tyr Tyr Gly Tyr Thr Ser
1               5                   10

<210> SEQ ID NO 52
<211> LENGTH: 6
<212> TYPE: PRT
<213> ORGANISM: Homo sapiens

<400> SEQUENCE: 52

Thr Tyr Tyr Tyr Pro Phe
1               5

<210> SEQ ID NO 53
<211> LENGTH: 13
<212> TYPE: PRT
<213> ORGANISM: Homo sapiens

```
<400> SEQUENCE: 53

Trp His Tyr Met Trp Thr Trp Leu Ser Pro Phe Gly Met
1               5                   10

<210> SEQ ID NO 54
<211> LENGTH: 6
<212> TYPE: PRT
<213> ORGANISM: Homo sapiens

<400> SEQUENCE: 54

Phe Tyr Ser Ser Ser Ile
1               5

<210> SEQ ID NO 55
<211> LENGTH: 6
<212> TYPE: PRT
<213> ORGANISM: Homo sapiens

<400> SEQUENCE: 55

Ser Tyr Trp Ser Pro Ile
1               5

<210> SEQ ID NO 56
<211> LENGTH: 13
<212> TYPE: PRT
<213> ORGANISM: Homo sapiens

<400> SEQUENCE: 56

Ser Arg Gly Ser Trp Ser Thr Pro Ile Pro Trp Gly Ile
1               5                   10

<210> SEQ ID NO 57
<211> LENGTH: 6
<212> TYPE: PRT
<213> ORGANISM: Homo sapiens

<400> SEQUENCE: 57

Phe Ser Ser Ser Ser Ile
1               5

<210> SEQ ID NO 58
<211> LENGTH: 6
<212> TYPE: PRT
<213> ORGANISM: Homo sapiens

<400> SEQUENCE: 58

Gln Phe Tyr Leu Pro Ile
1               5

<210> SEQ ID NO 59
<211> LENGTH: 12
<212> TYPE: PRT
<213> ORGANISM: Homo sapiens

<400> SEQUENCE: 59

Pro Val Trp Tyr Tyr Tyr Tyr His Gly Met Ala Met
1               5                   10

<210> SEQ ID NO 60
<211> LENGTH: 10
<212> TYPE: PRT
<213> ORGANISM: Homo sapiens

<400> SEQUENCE: 60
```

Ser Ile Ser Ser Tyr Ser Gly Tyr Thr Ser
1               5                   10

<210> SEQ ID NO 61
<211> LENGTH: 7
<212> TYPE: PRT
<213> ORGANISM: Homo sapiens

<400> SEQUENCE: 61

Tyr Tyr Phe Gly Ser Leu Val
1               5

<210> SEQ ID NO 62
<211> LENGTH: 12
<212> TYPE: PRT
<213> ORGANISM: Homo sapiens

<400> SEQUENCE: 62

Trp Ser Trp Arg Gly Glu Phe Trp Glu Ser Gly Leu
1               5                   10

<210> SEQ ID NO 63
<211> LENGTH: 6
<212> TYPE: PRT
<213> ORGANISM: Homo sapiens

<400> SEQUENCE: 63

Val Ser Ser Tyr Ser Ile
1               5

<210> SEQ ID NO 64
<211> LENGTH: 10
<212> TYPE: PRT
<213> ORGANISM: Homo sapiens

<400> SEQUENCE: 64

Ser Ile Ser Ser Tyr Ser Gly Ser Thr Ser
1               5                   10

<210> SEQ ID NO 65
<211> LENGTH: 8
<212> TYPE: PRT
<213> ORGANISM: Homo sapiens

<400> SEQUENCE: 65

Ser Val Gly Tyr Gly Ser Leu Ile
1               5

<210> SEQ ID NO 66
<211> LENGTH: 12
<212> TYPE: PRT
<213> ORGANISM: Homo sapiens

<400> SEQUENCE: 66

Ser Phe Pro Trp Gly Phe Thr Lys Gly Tyr Ala Leu
1               5                   10

<210> SEQ ID NO 67
<211> LENGTH: 10
<212> TYPE: PRT
<213> ORGANISM: Homo sapiens

<400> SEQUENCE: 67

Tyr Ile Ser Ser Tyr Tyr Gly Tyr Thr Ser
1               5                   10

<210> SEQ ID NO 68
<211> LENGTH: 6
<212> TYPE: PRT
<213> ORGANISM: Homo sapiens

<400> SEQUENCE: 68

Tyr Tyr Met Ser Leu Ile
1               5

<210> SEQ ID NO 69
<211> LENGTH: 12
<212> TYPE: PRT
<213> ORGANISM: Homo sapiens

<400> SEQUENCE: 69

Glu Ser Gly Tyr Trp Trp Gly Gly Pro Tyr Ala Leu
1               5                   10

<210> SEQ ID NO 70
<211> LENGTH: 6
<212> TYPE: PRT
<213> ORGANISM: Homo sapiens

<400> SEQUENCE: 70

Phe Tyr Ser Ser Tyr Ile
1               5

<210> SEQ ID NO 71
<211> LENGTH: 10
<212> TYPE: PRT
<213> ORGANISM: Homo sapiens

<400> SEQUENCE: 71

Tyr Ile Tyr Ser Ser Ser Gly Tyr Thr Tyr
1               5                   10

<210> SEQ ID NO 72
<211> LENGTH: 6
<212> TYPE: PRT
<213> ORGANISM: Homo sapiens

<400> SEQUENCE: 72

Ser Tyr Met Gln Leu Val
1               5

<210> SEQ ID NO 73
<211> LENGTH: 13
<212> TYPE: PRT
<213> ORGANISM: Homo sapiens

<400> SEQUENCE: 73

Ser Tyr His Tyr Tyr Trp Val Ser Phe Trp Ser Gly Met
1               5                   10

<210> SEQ ID NO 74
<211> LENGTH: 10
<212> TYPE: PRT
<213> ORGANISM: Homo sapiens

<400> SEQUENCE: 74

Ser Ile Tyr Pro Tyr Ser Gly Ser Thr Ser
1               5                   10

```
<210> SEQ ID NO 75
<211> LENGTH: 6
<212> TYPE: PRT
<213> ORGANISM: Homo sapiens

<400> SEQUENCE: 75

Asp Trp Ser Tyr Pro Ile
1               5

<210> SEQ ID NO 76
<211> LENGTH: 12
<212> TYPE: PRT
<213> ORGANISM: Homo sapiens

<400> SEQUENCE: 76

Glu Ser Lys Tyr Trp Tyr Trp Leu Tyr Tyr Ala Ile
1               5                   10

<210> SEQ ID NO 77
<211> LENGTH: 14
<212> TYPE: PRT
<213> ORGANISM: Homo sapiens

<400> SEQUENCE: 77

Ser Pro Gly Tyr Tyr Met Trp Asp Trp Trp His Gly Phe
1               5                   10

<210> SEQ ID NO 78
<211> LENGTH: 6
<212> TYPE: PRT
<213> ORGANISM: Homo sapiens

<400> SEQUENCE: 78

Tyr Tyr Phe Lys Pro Ile
1               5

<210> SEQ ID NO 79
<211> LENGTH: 14
<212> TYPE: PRT
<213> ORGANISM: Homo sapiens

<400> SEQUENCE: 79

Ser Tyr Pro Gly Tyr Ser Trp Trp Ser Tyr Phe Ala Leu
1               5                   10

<210> SEQ ID NO 80
<211> LENGTH: 10
<212> TYPE: PRT
<213> ORGANISM: Homo sapiens

<400> SEQUENCE: 80

Ser Ile Ser Pro Tyr Tyr Gly Ser Thr Ser
1               5                   10

<210> SEQ ID NO 81
<211> LENGTH: 6
<212> TYPE: PRT
<213> ORGANISM: Homo sapiens

<400> SEQUENCE: 81

Tyr Tyr Trp Ser Leu Phe
1               5

<210> SEQ ID NO 82
<211> LENGTH: 13
```

```
<212> TYPE: PRT
<213> ORGANISM: Homo sapiens

<400> SEQUENCE: 82

Tyr Phe Leu Met Pro Trp Arg Phe Gly His Tyr Gly Met
1               5                   10

<210> SEQ ID NO 83
<211> LENGTH: 10
<212> TYPE: PRT
<213> ORGANISM: Homo sapiens

<400> SEQUENCE: 83

Ser Ile Tyr Ser Tyr Ser Gly Ser Thr Ser
1               5                   10

<210> SEQ ID NO 84
<211> LENGTH: 6
<212> TYPE: PRT
<213> ORGANISM: Homo sapiens

<400> SEQUENCE: 84

Ser Trp Trp Tyr Pro Ile
1               5

<210> SEQ ID NO 85
<211> LENGTH: 12
<212> TYPE: PRT
<213> ORGANISM: Homo sapiens

<400> SEQUENCE: 85

Ser Tyr Pro Trp Gly Tyr Ser Tyr Gly Phe Ala Leu
1               5                   10

<210> SEQ ID NO 86
<211> LENGTH: 10
<212> TYPE: PRT
<213> ORGANISM: Homo sapiens

<400> SEQUENCE: 86

Ser Ile Ser Ser Tyr Tyr Gly Tyr Thr Tyr
1               5                   10

<210> SEQ ID NO 87
<211> LENGTH: 6
<212> TYPE: PRT
<213> ORGANISM: Homo sapiens

<400> SEQUENCE: 87

Tyr Arg Gly Ser Leu Ile
1               5

<210> SEQ ID NO 88
<211> LENGTH: 13
<212> TYPE: PRT
<213> ORGANISM: Homo sapiens

<400> SEQUENCE: 88

Ser Tyr Ala Tyr Gly Gln Trp Gly Pro Arg Pro Ala Ile
1               5                   10

<210> SEQ ID NO 89
<211> LENGTH: 10
<212> TYPE: PRT
<213> ORGANISM: Homo sapiens
```

```
<400> SEQUENCE: 89

Ser Ile Ser Pro Tyr Tyr Gly Ser Thr Tyr
1               5                   10

<210> SEQ ID NO 90
<211> LENGTH: 8
<212> TYPE: PRT
<213> ORGANISM: Homo sapiens

<400> SEQUENCE: 90

Ser Tyr Trp Ser Ser Tyr Leu Ile
1               5

<210> SEQ ID NO 91
<211> LENGTH: 13
<212> TYPE: PRT
<213> ORGANISM: Homo sapiens

<400> SEQUENCE: 91

Glu Ser Tyr Leu Pro Val Trp Trp Ile Phe Tyr Gly Phe
1               5                   10

<210> SEQ ID NO 92
<211> LENGTH: 6
<212> TYPE: PRT
<213> ORGANISM: Homo sapiens

<400> SEQUENCE: 92

Val Ser Tyr Ser Tyr Ile
1               5

<210> SEQ ID NO 93
<211> LENGTH: 6
<212> TYPE: PRT
<213> ORGANISM: Homo sapiens

<400> SEQUENCE: 93

Ser Tyr Ser Tyr Pro Ile
1               5

<210> SEQ ID NO 94
<211> LENGTH: 14
<212> TYPE: PRT
<213> ORGANISM: Homo sapiens

<400> SEQUENCE: 94

Glu Tyr Asp Gly Tyr Tyr Tyr Ala Ala Gly Tyr Gly Ile
1               5                   10

<210> SEQ ID NO 95
<211> LENGTH: 6
<212> TYPE: PRT
<213> ORGANISM: Homo sapiens

<400> SEQUENCE: 95

Phe Ser Tyr Ser Tyr Ile
1               5

<210> SEQ ID NO 96
<211> LENGTH: 10
<212> TYPE: PRT
<213> ORGANISM: Homo sapiens

<400> SEQUENCE: 96
```

```
Ser Ile Tyr Ser Tyr Ser Gly Tyr Thr Ser
1               5                   10

<210> SEQ ID NO 97
<211> LENGTH: 7
<212> TYPE: PRT
<213> ORGANISM: Homo sapiens

<400> SEQUENCE: 97

Tyr Tyr Ser Trp Tyr Leu Ile
1               5

<210> SEQ ID NO 98
<211> LENGTH: 12
<212> TYPE: PRT
<213> ORGANISM: Homo sapiens

<400> SEQUENCE: 98

Gln Trp Trp Gln Tyr Gln Gly Phe Gln Gln Ala Ile
1               5                   10

<210> SEQ ID NO 99
<211> LENGTH: 14
<212> TYPE: PRT
<213> ORGANISM: Homo sapiens

<400> SEQUENCE: 99

Asn Gln Trp Asp Pro Ile Tyr Ser Tyr Gly Gly Phe Ala Leu
1               5                   10

<210> SEQ ID NO 100
<211> LENGTH: 10
<212> TYPE: PRT
<213> ORGANISM: Homo sapiens

<400> SEQUENCE: 100

Ser Ile Ser Ser Ser Tyr Ser Tyr Thr Ser
1               5                   10

<210> SEQ ID NO 101
<211> LENGTH: 7
<212> TYPE: PRT
<213> ORGANISM: Homo sapiens

<400> SEQUENCE: 101

Ser Val Ser Gly Tyr Leu Ile
1               5

<210> SEQ ID NO 102
<211> LENGTH: 14
<212> TYPE: PRT
<213> ORGANISM: Homo sapiens

<400> SEQUENCE: 102

Ser Phe Pro Tyr Tyr Gln Thr Tyr Gly Trp Tyr Phe Ala Leu
1               5                   10

<210> SEQ ID NO 103
<211> LENGTH: 6
<212> TYPE: PRT
<213> ORGANISM: Homo sapiens

<400> SEQUENCE: 103

Val Gly Tyr Gln Pro Ile
```

```
1               5
```

<210> SEQ ID NO 104
<211> LENGTH: 13
<212> TYPE: PRT
<213> ORGANISM: Homo sapiens

<400> SEQUENCE: 104

```
Trp Ser Tyr Asp Gln Ser Met Ser Tyr Lys Ser Gly Met
1               5                   10
```

<210> SEQ ID NO 105
<211> LENGTH: 6
<212> TYPE: PRT
<213> ORGANISM: Homo sapiens

<400> SEQUENCE: 105

```
Val Tyr Tyr Tyr Tyr Ile
1               5
```

<210> SEQ ID NO 106
<211> LENGTH: 6
<212> TYPE: PRT
<213> ORGANISM: Homo sapiens

<400> SEQUENCE: 106

```
Tyr Ser Tyr Ser Leu Val
1               5
```

<210> SEQ ID NO 107
<211> LENGTH: 12
<212> TYPE: PRT
<213> ORGANISM: Homo sapiens

<400> SEQUENCE: 107

```
Trp Trp Asp Ser Trp Tyr Gly Gly Ser Thr Ala Ile
1               5                   10
```

<210> SEQ ID NO 108
<211> LENGTH: 10
<212> TYPE: PRT
<213> ORGANISM: Homo sapiens

<400> SEQUENCE: 108

```
Tyr Ile Ser Ser Ser Tyr Gly Tyr Thr Ser
1               5                   10
```

<210> SEQ ID NO 109
<211> LENGTH: 6
<212> TYPE: PRT
<213> ORGANISM: Homo sapiens

<400> SEQUENCE: 109

```
Tyr Trp Tyr Gln Pro Ile
1               5
```

<210> SEQ ID NO 110
<211> LENGTH: 13
<212> TYPE: PRT
<213> ORGANISM: Homo sapiens

<400> SEQUENCE: 110

```
Ser Tyr Thr Ser Ser Tyr Ser Ser Lys Tyr His Gly Met
1               5                   10
```

<210> SEQ ID NO 111
<211> LENGTH: 6
<212> TYPE: PRT
<213> ORGANISM: Homo sapiens

<400> SEQUENCE: 111

Ser Trp Tyr Pro Pro Leu
1               5

<210> SEQ ID NO 112
<211> LENGTH: 13
<212> TYPE: PRT
<213> ORGANISM: Homo sapiens

<400> SEQUENCE: 112

Gly Tyr Gly Ser Arg Trp Trp Tyr Ser Gly Arg Gly Met
1               5                   10

<210> SEQ ID NO 113
<211> LENGTH: 6
<212> TYPE: PRT
<213> ORGANISM: Homo sapiens

<400> SEQUENCE: 113

Val Ser Ser Ser Tyr Ile
1               5

<210> SEQ ID NO 114
<211> LENGTH: 10
<212> TYPE: PRT
<213> ORGANISM: Homo sapiens

<400> SEQUENCE: 114

Ser Ile Tyr Ser Tyr Ser Gly Tyr Thr Tyr
1               5                   10

<210> SEQ ID NO 115
<211> LENGTH: 8
<212> TYPE: PRT
<213> ORGANISM: Homo sapiens

<400> SEQUENCE: 115

Ala Ser Tyr His Gln Gly Pro Leu
1               5

<210> SEQ ID NO 116
<211> LENGTH: 12
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid

<400> SEQUENCE: 116

Ser Tyr Gly Phe Tyr Tyr Xaa Ala Arg Tyr Gly Leu
1               5                   10

<210> SEQ ID NO 117
<211> LENGTH: 7
<212> TYPE: PRT
<213> ORGANISM: Homo sapiens

<400> SEQUENCE: 117

Ser Ser Gly His Gln Leu Val

<210> SEQ ID NO 118
<211> LENGTH: 12
<212> TYPE: PRT
<213> ORGANISM: Homo sapiens

<400> SEQUENCE: 118

Tyr Glu Arg Ser Tyr Trp Gly Lys Gly Trp Ala Met
1               5                   10

<210> SEQ ID NO 119
<211> LENGTH: 10
<212> TYPE: PRT
<213> ORGANISM: Homo sapiens

<400> SEQUENCE: 119

Ser Ile Ser Ser Ser Tyr Gly Tyr Thr Tyr
1               5                   10

<210> SEQ ID NO 120
<211> LENGTH: 6
<212> TYPE: PRT
<213> ORGANISM: Homo sapiens

<400> SEQUENCE: 120

Ser Trp Ser Ser Leu Val
1               5

<210> SEQ ID NO 121
<211> LENGTH: 16
<212> TYPE: PRT
<213> ORGANISM: Homo sapiens

<400> SEQUENCE: 121

Tyr Trp Trp Tyr Ala Trp Pro Glu Asp Trp Tyr Phe Ala Gln Ala Met
1               5                   10                  15

<210> SEQ ID NO 122
<211> LENGTH: 12
<212> TYPE: PRT
<213> ORGANISM: Homo sapiens

<400> SEQUENCE: 122

Gly Tyr Lys Val Tyr Tyr Ser Tyr Ser Ser Gly Ile
1               5                   10

<210> SEQ ID NO 123
<211> LENGTH: 6
<212> TYPE: PRT
<213> ORGANISM: Homo sapiens

<400> SEQUENCE: 123

Ile Tyr Tyr Tyr Ser Ile
1               5

<210> SEQ ID NO 124
<211> LENGTH: 10
<212> TYPE: PRT
<213> ORGANISM: Homo sapiens

<400> SEQUENCE: 124

Ser Ile Ser Ser Ser Ser Gly Ser Thr Tyr
1               5                   10

```
<210> SEQ ID NO 125
<211> LENGTH: 6
<212> TYPE: PRT
<213> ORGANISM: Homo sapiens

<400> SEQUENCE: 125

Ile Gly Trp Tyr Pro Ile
1               5

<210> SEQ ID NO 126
<211> LENGTH: 12
<212> TYPE: PRT
<213> ORGANISM: Homo sapiens

<400> SEQUENCE: 126

His Thr Trp Thr Tyr Gln Gly Phe Phe Tyr Ala Phe
1               5                   10

<210> SEQ ID NO 127
<211> LENGTH: 6
<212> TYPE: PRT
<213> ORGANISM: Homo sapiens

<400> SEQUENCE: 127

Leu Ser Ser Ser Ser Ile
1               5

<210> SEQ ID NO 128
<211> LENGTH: 10
<212> TYPE: PRT
<213> ORGANISM: Homo sapiens

<400> SEQUENCE: 128

Tyr Ile Tyr Pro Ser Ser Gly Ser Thr Ser
1               5                   10

<210> SEQ ID NO 129
<211> LENGTH: 6
<212> TYPE: PRT
<213> ORGANISM: Homo sapiens

<400> SEQUENCE: 129

Gly Gly Tyr Ala Leu Ile
1               5

<210> SEQ ID NO 130
<211> LENGTH: 6
<212> TYPE: PRT
<213> ORGANISM: Homo sapiens

<400> SEQUENCE: 130

His Tyr Trp Phe Ala Met
1               5

<210> SEQ ID NO 131
<211> LENGTH: 10
<212> TYPE: PRT
<213> ORGANISM: Homo sapiens

<400> SEQUENCE: 131

Ser Ile Tyr Pro Ser Ser Gly Tyr Thr Tyr
1               5                   10

<210> SEQ ID NO 132
```

```
<211> LENGTH: 7
<212> TYPE: PRT
<213> ORGANISM: Homo sapiens

<400> SEQUENCE: 132

Tyr Gly Tyr Ser Ser Leu Leu
1               5

<210> SEQ ID NO 133
<211> LENGTH: 12
<212> TYPE: PRT
<213> ORGANISM: Homo sapiens

<400> SEQUENCE: 133

Tyr Leu Trp Thr Gly Ser Trp Gly Tyr Gly Ala Ile
1               5                   10

<210> SEQ ID NO 134
<211> LENGTH: 10
<212> TYPE: PRT
<213> ORGANISM: Homo sapiens

<400> SEQUENCE: 134

Tyr Ile Ser Pro Tyr Ser Gly Tyr Thr Ser
1               5                   10

<210> SEQ ID NO 135
<211> LENGTH: 7
<212> TYPE: PRT
<213> ORGANISM: Homo sapiens

<400> SEQUENCE: 135

Ser Leu Trp Arg Trp Pro Ile
1               5

<210> SEQ ID NO 136
<211> LENGTH: 12
<212> TYPE: PRT
<213> ORGANISM: Homo sapiens

<400> SEQUENCE: 136

Ser Gly Trp Tyr Tyr Gly Phe Gly Tyr Tyr Ala Met
1               5                   10

<210> SEQ ID NO 137
<211> LENGTH: 6
<212> TYPE: PRT
<213> ORGANISM: Homo sapiens

<400> SEQUENCE: 137

Val Ser Ser Ser Ser Ile
1               5

<210> SEQ ID NO 138
<211> LENGTH: 8
<212> TYPE: PRT
<213> ORGANISM: Homo sapiens

<400> SEQUENCE: 138

Gln Tyr Phe Tyr Gln Ser Leu Ile
1               5

<210> SEQ ID NO 139
<211> LENGTH: 13
<212> TYPE: PRT
```

```
<213> ORGANISM: Homo sapiens

<400> SEQUENCE: 139

Tyr Thr Tyr Tyr Phe Ser Asp His Gly Pro Gly Ala Phe
1               5                   10

<210> SEQ ID NO 140
<211> LENGTH: 10
<212> TYPE: PRT
<213> ORGANISM: Homo sapiens

<400> SEQUENCE: 140

Tyr Ile Ser Ser Tyr Ser Gly Tyr Thr Ser
1               5                   10

<210> SEQ ID NO 141
<211> LENGTH: 8
<212> TYPE: PRT
<213> ORGANISM: Homo sapiens

<400> SEQUENCE: 141

Tyr Ser Phe Trp Ser Ser Leu Ile
1               5

<210> SEQ ID NO 142
<211> LENGTH: 12
<212> TYPE: PRT
<213> ORGANISM: Homo sapiens

<400> SEQUENCE: 142

Pro Ser Met Trp Tyr Tyr Tyr Trp Gly Ser Ala Ile
1               5                   10

<210> SEQ ID NO 143
<211> LENGTH: 10
<212> TYPE: PRT
<213> ORGANISM: Homo sapiens

<400> SEQUENCE: 143

Ser Ile Ser Pro Ser Tyr Gly Tyr Thr Ser
1               5                   10

<210> SEQ ID NO 144
<211> LENGTH: 6
<212> TYPE: PRT
<213> ORGANISM: Homo sapiens

<400> SEQUENCE: 144

Ser Ser Tyr Ser Pro Ile
1               5

<210> SEQ ID NO 145
<211> LENGTH: 14
<212> TYPE: PRT
<213> ORGANISM: Homo sapiens

<400> SEQUENCE: 145

Ser Tyr Trp Tyr His Val Gly Ser Trp His Tyr Thr Gly Met
1               5                   10

<210> SEQ ID NO 146
<211> LENGTH: 12
<212> TYPE: PRT
<213> ORGANISM: Homo sapiens
```

```
<400> SEQUENCE: 146

Asp Tyr Tyr His Gly Tyr Asn Trp Gly Gly Phe
1               5                   10

<210> SEQ ID NO 147
<211> LENGTH: 6
<212> TYPE: PRT
<213> ORGANISM: Homo sapiens

<400> SEQUENCE: 147

Ser Phe Tyr Glu Pro Ile
1               5

<210> SEQ ID NO 148
<211> LENGTH: 7
<212> TYPE: PRT
<213> ORGANISM: Homo sapiens

<400> SEQUENCE: 148

Met Gly Val Tyr Tyr Ala Phe
1               5

<210> SEQ ID NO 149
<211> LENGTH: 6
<212> TYPE: PRT
<213> ORGANISM: Homo sapiens

<400> SEQUENCE: 149

Trp Val Tyr His Pro Ile
1               5

<210> SEQ ID NO 150
<211> LENGTH: 12
<212> TYPE: PRT
<213> ORGANISM: Homo sapiens

<400> SEQUENCE: 150

Ser Gln Phe Glu Tyr Ser Gly Val Tyr Gly Gly Leu
1               5                   10

<210> SEQ ID NO 151
<211> LENGTH: 10
<212> TYPE: PRT
<213> ORGANISM: Homo sapiens

<400> SEQUENCE: 151

Tyr Ile Ser Ser Ser Ser Gly Tyr Thr Tyr
1               5                   10

<210> SEQ ID NO 152
<211> LENGTH: 7
<212> TYPE: PRT
<213> ORGANISM: Homo sapiens

<400> SEQUENCE: 152

Ser Lys Tyr Ser Gln Pro Ile
1               5

<210> SEQ ID NO 153
<211> LENGTH: 12
<212> TYPE: PRT
<213> ORGANISM: Homo sapiens

<400> SEQUENCE: 153
```

```
Trp Thr Phe Pro Lys Gly Ser Gln Trp Ser Ala Leu
1               5                   10
```

<210> SEQ ID NO 154
<211> LENGTH: 6
<212> TYPE: PRT
<213> ORGANISM: Homo sapiens

<400> SEQUENCE: 154

```
Glu Tyr Ser Tyr Pro Val
1               5
```

<210> SEQ ID NO 155
<211> LENGTH: 6
<212> TYPE: PRT
<213> ORGANISM: Homo sapiens

<400> SEQUENCE: 155

```
Ile His Trp Trp Ala Met
1               5
```

<210> SEQ ID NO 156
<211> LENGTH: 6
<212> TYPE: PRT
<213> ORGANISM: Homo sapiens

<400> SEQUENCE: 156

```
Thr Trp Tyr Pro Leu Ile
1               5
```

<210> SEQ ID NO 157
<211> LENGTH: 15
<212> TYPE: PRT
<213> ORGANISM: Homo sapiens

<400> SEQUENCE: 157

```
Tyr Ser Ser Trp Trp Pro Tyr Ser Tyr Asp Ser Tyr Trp Ala Leu
1               5                   10                  15
```

<210> SEQ ID NO 158
<211> LENGTH: 6
<212> TYPE: PRT
<213> ORGANISM: Homo sapiens

<400> SEQUENCE: 158

```
Ala Arg Trp Gly Leu Val
1               5
```

<210> SEQ ID NO 159
<211> LENGTH: 13
<212> TYPE: PRT
<213> ORGANISM: Homo sapiens

<400> SEQUENCE: 159

```
Pro Ser Trp Trp Met Arg Arg Tyr Ser Tyr Trp Gly Leu
1               5                   10
```

<210> SEQ ID NO 160
<211> LENGTH: 6
<212> TYPE: PRT
<213> ORGANISM: Homo sapiens

<400> SEQUENCE: 160

```
Tyr Leu Tyr Gly Leu Ile
1               5
```

```
<210> SEQ ID NO 161
<211> LENGTH: 13
<212> TYPE: PRT
<213> ORGANISM: Homo sapiens

<400> SEQUENCE: 161

Met Asn Ser Lys Gly Glu Tyr Gln Lys Val Ser Gly Leu
1               5                   10

<210> SEQ ID NO 162
<211> LENGTH: 7
<212> TYPE: PRT
<213> ORGANISM: Homo sapiens

<400> SEQUENCE: 162

Thr Trp Ser Tyr Gln Pro Val
1               5

<210> SEQ ID NO 163
<211> LENGTH: 14
<212> TYPE: PRT
<213> ORGANISM: Homo sapiens

<400> SEQUENCE: 163

Tyr Thr Tyr Tyr Ser Asp Gln Trp Tyr Lys Leu Asn Ala Leu
1               5                   10

<210> SEQ ID NO 164
<211> LENGTH: 6
<212> TYPE: PRT
<213> ORGANISM: Homo sapiens

<400> SEQUENCE: 164

Ile Ser Ser Ser Tyr Ile
1               5

<210> SEQ ID NO 165
<211> LENGTH: 10
<212> TYPE: PRT
<213> ORGANISM: Homo sapiens

<400> SEQUENCE: 165

Ser Ile Ser Ser Tyr Ser Gly Ser Thr Tyr
1               5                   10

<210> SEQ ID NO 166
<211> LENGTH: 6
<212> TYPE: PRT
<213> ORGANISM: Homo sapiens

<400> SEQUENCE: 166

Ser Asn Trp Gln Leu Leu
1               5

<210> SEQ ID NO 167
<211> LENGTH: 14
<212> TYPE: PRT
<213> ORGANISM: Homo sapiens

<400> SEQUENCE: 167

Trp Tyr His Pro Phe Gln Val Arg Ala Trp Asn Trp Ala Met
1               5                   10
```

```
<210> SEQ ID NO 168
<211> LENGTH: 10
<212> TYPE: PRT
<213> ORGANISM: Homo sapiens

<400> SEQUENCE: 168

Tyr Ile Tyr Pro Tyr Tyr Gly Ser Thr Ser
1               5                   10

<210> SEQ ID NO 169
<211> LENGTH: 8
<212> TYPE: PRT
<213> ORGANISM: Homo sapiens

<400> SEQUENCE: 169

Ser Tyr Tyr Gly Ser Tyr Leu Ile
1               5

<210> SEQ ID NO 170
<211> LENGTH: 12
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 170

Ser Tyr Xaa Phe Xaa Tyr Xaa Ala Xaa Tyr Xaa Leu
1               5                   10

<210> SEQ ID NO 171
<211> LENGTH: 10
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 171

Ser Ile Xaa Ser Tyr Xaa Gly Tyr Thr Ser
1               5                   10

<210> SEQ ID NO 172
<211> LENGTH: 7
<212> TYPE: PRT
<213> ORGANISM: Homo sapiens
<220> FEATURE:
<221> NAME/KEY: misc_feature
<222> LOCATION: (2)..(2)
```

<223> OTHER INFORMATION: Xaa can be any naturally occurring amino acid

<400> SEQUENCE: 172

Ser Xaa Gly His Gln Leu Val
1               5

<210> SEQ ID NO 173
<211> LENGTH: 6
<212> TYPE: PRT
<213> ORGANISM: Homo sapiens

<400> SEQUENCE: 173

Asp Gln Trp Tyr Gly Met
1               5

<210> SEQ ID NO 174
<211> LENGTH: 10
<212> TYPE: PRT
<213> ORGANISM: Homo sapiens

<400> SEQUENCE: 174

Tyr Ile Tyr Ser Tyr Ser Gly Tyr Thr Ser
1               5                   10

<210> SEQ ID NO 175
<211> LENGTH: 6
<212> TYPE: PRT
<213> ORGANISM: Homo sapiens

<400> SEQUENCE: 175

Lys Tyr Ser Arg Leu Ile
1               5

<210> SEQ ID NO 176
<211> LENGTH: 6
<212> TYPE: PRT
<213> ORGANISM: Homo sapiens

<400> SEQUENCE: 176

Gly Arg Tyr Trp Ala Met
1               5

<210> SEQ ID NO 177
<211> LENGTH: 10
<212> TYPE: PRT
<213> ORGANISM: Homo sapiens

<400> SEQUENCE: 177

Tyr Ile Tyr Pro Ser Ser Gly Tyr Thr Tyr
1               5                   10

<210> SEQ ID NO 178
<211> LENGTH: 6
<212> TYPE: PRT
<213> ORGANISM: Homo sapiens

<400> SEQUENCE: 178

Pro His Tyr Gly Leu Ile
1               5

<210> SEQ ID NO 179
<211> LENGTH: 6
<212> TYPE: PRT
<213> ORGANISM: Homo sapiens

```
<400> SEQUENCE: 179

Trp Arg Gly Gly Gly Leu
1               5

<210> SEQ ID NO 180
<211> LENGTH: 7
<212> TYPE: PRT
<213> ORGANISM: Homo sapiens

<400> SEQUENCE: 180

Gly Tyr Tyr His Asn Leu Ile
1               5

<210> SEQ ID NO 181
<211> LENGTH: 10
<212> TYPE: PRT
<213> ORGANISM: Homo sapiens

<400> SEQUENCE: 181

Tyr Met Lys Ser Phe Trp Tyr Ala Gly Met
1               5                   10

<210> SEQ ID NO 182
<211> LENGTH: 10
<212> TYPE: PRT
<213> ORGANISM: Homo sapiens

<400> SEQUENCE: 182

Ser Ile Tyr Pro Ser Tyr Gly Ser Thr Tyr
1               5                   10

<210> SEQ ID NO 183
<211> LENGTH: 6
<212> TYPE: PRT
<213> ORGANISM: Homo sapiens

<400> SEQUENCE: 183

Gly Tyr Ser Ser Leu Val
1               5

<210> SEQ ID NO 184
<211> LENGTH: 12
<212> TYPE: PRT
<213> ORGANISM: Homo sapiens

<400> SEQUENCE: 184

Gly Phe Trp Arg Tyr Trp Met Trp Arg Phe Gly Leu
1               5                   10

<210> SEQ ID NO 185
<211> LENGTH: 10
<212> TYPE: PRT
<213> ORGANISM: Homo sapiens

<400> SEQUENCE: 185

Tyr Ile Tyr Ser Ser Tyr Gly Ser Thr Ser
1               5                   10

<210> SEQ ID NO 186
<211> LENGTH: 6
<212> TYPE: PRT
<213> ORGANISM: Homo sapiens

<400> SEQUENCE: 186
```

Ser Tyr Tyr Arg Pro Ile
1               5

<210> SEQ ID NO 187
<211> LENGTH: 12
<212> TYPE: PRT
<213> ORGANISM: Homo sapiens

<400> SEQUENCE: 187

Gly Ser Asp Tyr Tyr Gly Gln Trp Gly Tyr Ala Ile
1               5                   10

<210> SEQ ID NO 188
<211> LENGTH: 10
<212> TYPE: PRT
<213> ORGANISM: Homo sapiens

<400> SEQUENCE: 188

Tyr Ile Ser Ser Tyr Tyr Gly Ser Thr Tyr
1               5                   10

<210> SEQ ID NO 189
<211> LENGTH: 6
<212> TYPE: PRT
<213> ORGANISM: Homo sapiens

<400> SEQUENCE: 189

Tyr Gln Gly Ser Leu Ile
1               5

<210> SEQ ID NO 190
<211> LENGTH: 12
<212> TYPE: PRT
<213> ORGANISM: Homo sapiens

<400> SEQUENCE: 190

Gly Tyr Gly Tyr Tyr Ser Tyr Lys Tyr Gly Leu
1               5                   10

<210> SEQ ID NO 191
<211> LENGTH: 10
<212> TYPE: PRT
<213> ORGANISM: Homo sapiens

<400> SEQUENCE: 191

Ser Ile Ser Pro Ser Tyr Gly Ser Thr Tyr
1               5                   10

<210> SEQ ID NO 192
<211> LENGTH: 6
<212> TYPE: PRT
<213> ORGANISM: Homo sapiens

<400> SEQUENCE: 192

Ser Tyr Val Lys Pro Leu
1               5

<210> SEQ ID NO 193
<211> LENGTH: 12
<212> TYPE: PRT
<213> ORGANISM: Homo sapiens

<400> SEQUENCE: 193

Asn Ala Tyr Tyr Asn Tyr Ser Gly His Ala Leu
1               5                   10

```
<210> SEQ ID NO 194
<211> LENGTH: 6
<212> TYPE: PRT
<213> ORGANISM: Homo sapiens

<400> SEQUENCE: 194

Leu Ser Tyr Ser Ser Ile
1               5

<210> SEQ ID NO 195
<211> LENGTH: 6
<212> TYPE: PRT
<213> ORGANISM: Homo sapiens

<400> SEQUENCE: 195

Gly Ser Gly Ser Leu Phe
1               5

<210> SEQ ID NO 196
<211> LENGTH: 12
<212> TYPE: PRT
<213> ORGANISM: Homo sapiens

<400> SEQUENCE: 196

Trp Lys Met Ile Tyr Tyr Tyr His Tyr Val Gly Met
1               5                   10

<210> SEQ ID NO 197
<211> LENGTH: 10
<212> TYPE: PRT
<213> ORGANISM: Homo sapiens

<400> SEQUENCE: 197

Ser Ile Tyr Pro Tyr Tyr Gly Tyr Thr Ser
1               5                   10

<210> SEQ ID NO 198
<211> LENGTH: 8
<212> TYPE: PRT
<213> ORGANISM: Homo sapiens

<400> SEQUENCE: 198

Tyr Trp Ile Met Ser Ser Pro Phe
1               5

<210> SEQ ID NO 199
<211> LENGTH: 13
<212> TYPE: PRT
<213> ORGANISM: Homo sapiens

<400> SEQUENCE: 199

Tyr Ser Gly Gln Tyr Tyr Tyr Arg Tyr Ser Tyr Ala Leu
1               5                   10

<210> SEQ ID NO 200
<211> LENGTH: 13
<212> TYPE: PRT
<213> ORGANISM: Homo sapiens

<400> SEQUENCE: 200

Asp Tyr Tyr Tyr Tyr Phe Gly Trp Tyr Ser Asn Ala Leu
1               5                   10
```

<210> SEQ ID NO 201
<211> LENGTH: 13
<212> TYPE: PRT
<213> ORGANISM: Homo sapiens

<400> SEQUENCE: 201

Asp Tyr Tyr Tyr Tyr Phe Gly Trp Tyr Ser Asn Ala Leu
1               5                   10

<210> SEQ ID NO 202
<211> LENGTH: 7
<212> TYPE: PRT
<213> ORGANISM: Homo sapiens

<400> SEQUENCE: 202

Ile Tyr Tyr Tyr Gly Leu Ile
1               5

<210> SEQ ID NO 203
<211> LENGTH: 14
<212> TYPE: PRT
<213> ORGANISM: Homo sapiens

<400> SEQUENCE: 203

Lys Gly Gln Tyr Ser Pro Pro Tyr Trp His His Arg Ala Met
1               5                   10

<210> SEQ ID NO 204
<211> LENGTH: 14
<212> TYPE: PRT
<213> ORGANISM: Homo sapiens

<400> SEQUENCE: 204

Ser Leu Ser Ser Ser Tyr Tyr Ser Asn Trp Tyr Trp Gly Leu
1               5                   10

<210> SEQ ID NO 205
<211> LENGTH: 10
<212> TYPE: PRT
<213> ORGANISM: Homo sapiens

<400> SEQUENCE: 205

Tyr Ile Tyr Ser Ser Ser Gly Tyr Thr Ser
1               5                   10

<210> SEQ ID NO 206
<211> LENGTH: 6
<212> TYPE: PRT
<213> ORGANISM: Homo sapiens

<400> SEQUENCE: 206

Asn Tyr Gly Gly Leu Ile
1               5

<210> SEQ ID NO 207
<211> LENGTH: 14
<212> TYPE: PRT
<213> ORGANISM: Homo sapiens

<400> SEQUENCE: 207

Ser Tyr Pro Tyr Pro Met Tyr Tyr Ile Ser Lys Pro Ala Ile
1               5                   10

<210> SEQ ID NO 208
<211> LENGTH: 10

```
<212> TYPE: PRT
<213> ORGANISM: Homo sapiens

<400> SEQUENCE: 208

Tyr Ile Ser Ser Tyr Tyr Gly Ser Thr Ser
1               5                   10

<210> SEQ ID NO 209
<211> LENGTH: 6
<212> TYPE: PRT
<213> ORGANISM: Homo sapiens

<400> SEQUENCE: 209

Tyr Gln Gly Ser Leu Ile
1               5

<210> SEQ ID NO 210
<211> LENGTH: 236
<212> TYPE: PRT
<213> ORGANISM: Homo sapiens

<400> SEQUENCE: 210

Glu Ile Ser Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Asn Val
            20                  25                  30

Tyr Tyr Tyr Tyr Ile His Trp Val Arg Gln Ala Pro Gly Lys Gly Leu
        35                  40                  45

Glu Trp Val Ala Ser Ile Ser Pro Tyr Tyr Gly Tyr Thr Ser Ser Tyr
    50                  55                  60

Ala Asp Ser Val Lys Gly Arg Phe Thr Ile Ser Ala Asp Thr Ser Lys
65                  70                  75                  80

Asn Thr Ala Tyr Leu Gln Met Asn Ser Leu Arg Ala Glu Asp Thr Ala
                85                  90                  95

Val Tyr Tyr Cys Ala Arg Trp Ser Tyr Asp Gln Ser Met Ser Tyr Lys
            100                 105                 110

Ser Gly Met Asp Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr
225                 230                 235

<210> SEQ ID NO 211
<211> LENGTH: 215
<212> TYPE: PRT
<213> ORGANISM: Homo sapiens

<400> SEQUENCE: 211
```

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser Ser
            20                  25                  30

Ala Val Ala Trp Tyr Gln Gln Lys Pro Gly Lys Ala Pro Lys Leu Leu
        35                  40                  45

Ile Tyr Ser Ala Ser Ser Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Ser Tyr Ser Leu
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Ser Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 212
<211> LENGTH: 236
<212> TYPE: PRT
<213> ORGANISM: Homo sapiens

<400> SEQUENCE: 212

Glu Ile Ser Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Asn Ile
            20                  25                  30

Ser Tyr Ser Ser Ile His Trp Val Arg Gln Ala Pro Gly Lys Gly Leu
        35                  40                  45

Glu Trp Val Ala Ser Ile Tyr Ser Tyr Ser Gly Tyr Thr Ser Tyr Ala
    50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ala Arg Ser Tyr Trp Tyr His Val Gly Ser Trp His Tyr
            100                 105                 110

Thr Gly Met Asp Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr

```
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
                180                 185                 190
Leu Ser Ser Val Val Thr Val Pro Ser Ser Leu Gly Thr Gln Thr
                195                 200                 205
Tyr Ile Cys Asn Val Asn His Lys Pro Ser Asn Thr Lys Val Asp Lys
                210                 215                 220
Lys Val Glu Pro Lys Ser Cys Asp Lys Thr His Thr
225                 230                 235

<210> SEQ ID NO 213
<211> LENGTH: 215
<212> TYPE: PRT
<213> ORGANISM: Homo sapiens

<400> SEQUENCE: 213

Ser Asp Ile Gln Met Thr Gln Ser Pro Ser Ser Leu Ser Ala Ser Val
1               5                   10                  15
Gly Asp Arg Val Thr Ile Thr Cys Arg Ala Ser Gln Ser Val Ser Ser
                20                  25                  30
Ala Val Ala Trp Tyr Gln Gln Lys Pro Gly Lys Ala Pro Lys Leu Leu
            35                  40                  45
Ile Tyr Ser Ala Ser Ser Leu Tyr Ser Gly Val Pro Ser Arg Phe Ser
        50                  55                  60
Gly Ser Arg Ser Gly Thr Asp Phe Thr Leu Thr Ile Ser Ser Leu Gln
65                  70                  75                  80
Pro Glu Asp Phe Ala Thr Tyr Tyr Cys Gln Gln Ser Ser Ser Ser Leu
                85                  90                  95
Ile Thr Phe Gly Gln Gly Thr Lys Val Glu Ile Lys Arg Thr Val Ala
                100                 105                 110
Ala Pro Ser Val Phe Ile Phe Pro Pro Ser Asp Ser Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
Tyr Ala Cys Glu Val Thr His Gln Gly Leu Ser Ser Pro Val Thr Lys
            195                 200                 205
Ser Phe Asn Arg Gly Glu Cys
        210                 215

<210> SEQ ID NO 214
<211> LENGTH: 236
<212> TYPE: PRT
<213> ORGANISM: Artificial Sequence
<220> FEATURE:
<223> OTHER INFORMATION: synthetic Fab fragment sequence
<220> FEATURE:
<221> NAME/KEY: MISC_FEATURE
<222> LOCATION: (32)..(37)
<223> OTHER INFORMATION: Each Xaa located at postiions 32 through 37 can
      be any amino acid
```

```
<220> FEATURE:
<221> NAME/KEY: MISC_FEATURE
<222> LOCATION: (53)..(62)
<223> OTHER INFORMATION: Each Xaa located at positions 53 through 62 can
      be any amino acid
<220> FEATURE:
<221> NAME/KEY: MISC_FEATURE
<222> LOCATION: (102)..(115)
<223> OTHER INFORMATION: Each Xaa located at positions 102 through 115
      is any amino acid

<400> SEQUENCE: 214

Glu Ile Ser Glu Val Gln Leu Val Glu Ser Gly Gly Leu Val Gln
1               5                   10                  15

Pro Gly Gly Ser Leu Arg Leu Ser Cys Ala Ala Ser Gly Phe Asn Xaa
            20                  25                  30

Xaa Xaa Xaa Xaa Xaa His Trp Val Arg Gln Ala Pro Gly Lys Gly Leu
        35                  40                  45

Glu Trp Val Ala Xaa Xaa Xaa Xaa Xaa Xaa Xaa Xaa Xaa Tyr Ala
    50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ala Arg Xaa Xaa Xaa Xaa Xaa Xaa Xaa Xaa Xaa Xaa
            100                 105                 110

Xaa Xaa Xaa Asp Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Gln Thr
    195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr
225                 230                 235

<210> SEQ ID NO 215
<211> LENGTH: 210
<212> TYPE: PRT
<213> ORGANISM: Artificial Sequence
<220> FEATURE:
<223> OTHER INFORMATION: Synthetic Fab fragment sequence
<220> FEATURE:
<221> NAME/KEY: MISC_FEATURE
<222> LOCATION: (92)..(92)
<223> OTHER INFORMATION: Xaa at position 92 is a random sequence of 6
      amino aicds

<400> SEQUENCE: 215

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser Ser
            20                  25                  30
```

```
Ala Val Ala Trp Tyr Gln Gln Lys Pro Gly Lys Ala Pro Lys Leu Leu
             35                  40                  45

Ile Tyr Ser Ala Ser Ser Leu Tyr Ser Gly Val Pro Ser Arg Phe Ser
 50                  55                  60

Gly Ser Arg Ser Gly Thr Asp Phe Thr Leu Thr Ile Ser Ser Leu Gln
 65                  70                  75                  80

Pro Glu Asp Phe Ala Thr Tyr Tyr Cys Gln Gln Xaa Thr Phe Gly Gln
                 85                  90                  95

Gly Thr Lys Val Glu Ile Lys Arg Thr Val Ala Ala Pro Ser Val Phe
                100                 105                 110

Ile Phe Pro Pro Ser Asp Ser Gln Leu Lys Ser Gly Thr Ala Ser Val
            115                 120                 125

Val Cys Leu Leu Asn Asn Phe Tyr Pro Arg Glu Ala Lys Val Gln Trp
130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210

<210> SEQ ID NO 216
<211> LENGTH: 97
<212> TYPE: PRT
<213> ORGANISM: Lloviu virus

<400> SEQUENCE: 216

Asp Asn Ser Glu Ser Asp Leu Ile Asp Gln Met Tyr Gln His Ile Phe
 1               5                  10                  15

Glu Thr Glu Gly Ala Tyr Ala Ala Ile Asn Tyr Tyr Lys Thr Thr
                20                  25                  30

Gly Arg Pro Val Thr Phe Thr Ser Asn Asn His Asp Tyr Thr Phe
             35                  40                  45

Pro Gln Asp Ile Glu Gly Leu Phe Pro Pro Trp Glu Gly Lys Glu Asn
            50                  55                  60

Gln Lys Val Ala Glu Ile Leu Thr Asn Ser Leu His Glu Thr Gly Gln
 65                  70                  75                  80

Glu Trp Ala Asp Met Ser Ala Lys Glu Arg Tyr Leu Phe Leu Ile Asn
                 85                  90                  95

Asn

<210> SEQ ID NO 217
<211> LENGTH: 95
<212> TYPE: PRT
<213> ORGANISM: Marburg virus

<400> SEQUENCE: 217

Ser Ser Pro Ser Ala Pro Gln Glu Asp Thr Arg Ala Arg Glu Ala Tyr
 1               5                  10                  15

Glu Leu Ser Pro Asp Phe Thr Asn Tyr Glu Asp Asn Gln Gln Asn Trp
                20                  25                  30

Pro Gln Arg Val Val Thr Lys Lys Gly Arg Thr Phe Leu Tyr Pro Asn
```

```
                35                    40                   45
Asp Leu Leu Gln Thr Asn Pro Pro Glu Ser Leu Ile Thr Ala Leu Val
        50                    55                  60

Glu Glu Tyr Gln Asn Pro Val Ser Ala Lys Glu Leu Gln Ala Asp Trp
65                   70                   75                  80

Pro Asp Met Ser Phe Asp Glu Arg Arg His Val Ala Met Asn Leu
                85                   90                  95
```

RECOMBINANT ANTIBODIES THAT RECOGNIZE THE C-TERMINAL DOMAINS OF EBOLA VIRUS NUCLEOPROTEIN

CROSS-REFERENCE TO RELATED APPLICATIONS

This application is a national stage entry under 35 USC § 371(b) of PCT/US2015/056017, filed on Oct. 16, 2015, which claims priority under 35 U.S.C. § 119 of U.S. Provisional Patent Application Ser. No. 62/065,392 filed Oct. 17, 2014, the entirety of both of which are incorporated herein by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 50,965 byte ASCII (Text) file named "263647SeqList_ST25.txt" created on Jan. 24, 2018.

FIELD OF THE PRESENT APPLICATION

The present disclosure relates to compositions and methods of utilizing the boundaries of the N-terminal and C-terminal domains of the Nucleoprotein from Ebola virus as highly stable recombinant protein antigens to generate antibodies for diagnosis and treatment of Ebola virus infection.

BACKGROUND

Viral hemorrhagic fevers (VHFs) constitute a group of severe illnesses in which the vascular system is damaged with accompanying internal bleeding, while regulatory functions of the body are critically impaired. Several distinct families of viruses cause VHF, with varying disease severity. The most dangerous VHF, associated with a mortality as high as 90%, is caused by the filoviruses (Filoviridae), such as Marburg virus (MARV) and Ebola virus (EBOV). Although outbreaks of Ebola hemorrhagic fever, first identified in 1976, are sporadic and endemic to Africa, EBOV constitutes a grave global potential health threat.

Five strains of EBOV have been identified to date. These include four African strains, including the Tai Forest (also known as Ivory Coast), Sudan, Zaire, and Bundibugyo, as well as the Reston strain from the Philippines. There is only one known MARV strain that is related to the EBOV strains. In addition, the distantly related Lloviu virus (LLOV) is found in insectivorous bats in Spain. Reston EBOV and Lloviu virus do not appear to be pathogenic in humans. In contrast, the Sudan, Ivory Coast, Bundibugyo and Zaire EBOV strains, as well as the MARV strain, have been associated with human VHF outbreaks.

Fatality rates for the EBOV viruses may range from about 20% to about 90%. For example, the EBOV ranges from about 40% for the Sudan and Bundibugyo strains to about 90% for the Zaire strain. The rate for the Tai Forest strain is not yet known owing to its rarity.

The highly pathogenic Marburg and Ebola viruses (MARV and EBOV) were discovered in 1967 and 1976, respectively. Although both cause deadly hemorrhagic fever with 20-90% mortality, until recently they caused only sporadic outbreaks confined to Central Africa. The endemic nature of these outbreaks provided limited incentive for development of effective vaccines, therapeutics and diagnostics.

The situation changed dramatically in 2014, when the world was confronted with the first widespread Ebola epidemic. This was the most challenging EBOV outbreak ever reported by the World Health Organization affecting people in Guinea and Liberia, with possible cases in Sierra Leone, Mali, and Ghana. There were also isolated cases identified in Spain, United States, United Kingdom and Italy. This was a specter of a worldwide epidemic.

Although the African outbreak has been mostly contained, as of July 2015 more than 27,000 suspected, probable and confirmed cases have been reported, with more than 11,000 documented deaths (CDC website). These figures most likely underestimate the real spread of the epidemic. The outbreak is still ongoing in Guinea and Sierra Leone, and a new case was diagnosed in Liberia even after the World Health Organization declared it free of the disease.

Owing to its pathogenicity, high mortality, and human-to-human transmission, EBOV and MARV are considered to be potential bioweapons and are classified as a Category A bioterrorism agent. Importantly, there are no approved vaccines or antiviral agents against EBOV, while existing therapies for infected individuals have minimal effects. The unprecedented severity of the 2014/2015 EBOV fever outbreak underscores the clear and present danger posed by the virus.

Considerable effort and resources have now been invested in the fight against EBOV, and rapid progress is being made towards development and approval of therapeutic antibodies, vaccines, and diagnostic tools. Of special note is the preparation of the recombinant ZMAPP therapeutic antibodies, which were shown to reverse the Ebola fever in non-human primates. These antibodies are currently undergoing clinical trials launched by the NIH in a partnership with the Liberian government. Further, there is considerable hope that an effective vaccine may soon be available: an rVSV-vectored vaccine expressing the Zaire EBOV surface glycoprotein has undergone an interim randomized trial with very promising results.

Nevertheless, much remains to be done. Currently, there are no small molecule drugs targeting the EBOV or MARV viruses, and more importantly, there are no inexpensive, reliable point-of-care diagnostics. Since it is unrealistic to expect that the whole population of Central and West Africa will be vaccinated any time soon, it is imperative that cheap and reliable diagnostic tools are developed. In particular, tools are necessary so that whenever a potentially infected individual is identified, we can quickly confirm the presence of EBOV or, even better, identify the viral strain. For example, there is intense interest in the molecular mechanisms of infectivity, replication, assembly, and pathogenesis of EBOV in humans, with the long-term objective of identifying suitable targets for drug discovery and the development of effective diagnostic tools.

A target of EBOV diagnostic and therapeutic research is the EBOV ssRNA genome. The EBOV ssRNA genome encodes seven proteins, most of which have multiple functions. Two of the EBOV proteins are the glycoprotein (GP) and the matrix protein, VP40, which are essential components of the viral envelope that surrounds the nucleocapsid. The nucleocapsid includes a viral negative-sense ssRNA complexed with five additional proteins, such as the Nucleoprotein or Nucleoprotein (NP), the VP24, VP30 and VP35 structural proteins, and the viral polymerase (L).

Nucleoproteins (NP) are found in all members of the order Mononegavirales, which groups together a number of important viruses that are highly pathogenic to humans, animals and plants, including Filoviridae, measles, mumps and rabies viruses, avian bornavirus, and many others. The ssRNA in these viruses is packaged into a helical complex that includes multiple copies of NP. The architectures of the resulting NP-ssRNA complexes differ among the Mononegavirales families. Insights into the structure-function relationships underlying the physiological role of NPs from Mononegavirales have been made possible owing to crystallographic studies of the proteins from rabies virus and bornavirus.

For example, Cryo-EM and tomography allowed for the reconstruction of the EBOV nucleocapsid at about 14 Angstrom (Å) to about 19 Å resolution. Recent intensive efforts have resulted in structural characterization, often using crystallography, of the five EBOV proteins, GP, VP40, VP24, VP30, and VP35. Proteins L and NP have so far eluded structural characterization. The NP plays a critical role in virus replication and maturation, and is the most abundant viral protein in infected cells and the viral nucleocapsid.

Interestingly, the Filoviridae members appear to have unusual NPs characterized by a longer polypeptide chain than those of other Mononegavirales, with two distinct functional modules, and the N-terminal domain exhibiting the canonical ssRNA-packaging function. Recent data suggest that the C-terminal domain, with an amino-acid sequence that shows no homology to any other protein, may serve as a unique hub for protein-protein interactions in the nucleocapsid that are distinct from any other Mononegavirales. Moreover, recent data show that the C-terminal fragment of the EBOV NP is a major antigenic determinant, raising the possibility that it could be effective in virus detection and diagnostics.

Rapid diagnostics make it possible to confirm or discard cases at points of treatment, reduce danger of infections in non-EBOV-positive patients, guide triage and clinical care. Until recently, the only approved diagnostic tool for EBOV detection was a PCR test which takes 2-6 hours, was contingent on access to proper instrumentation, and costs approximately $100 per assay. The World Health Organization (WHO) recently called for a test suited for use in peripheral health clinics with no access to laboratory infrastructure, taking no more than two steps with results no later than in 30 minutes, and with biosafety requirements limited to the use of personal protective equipment. Ideally, such inexpensive tests should selectively recognize EBOV antigens with high sensitivity specific in bodily fluids. Such diagnostic tests should also provide rapid, direct readout in a manner similar to fertility tests based in general terms on ELISA technology. Prototypes of such kits, made by the European companies Vedalab and Senova, are currently being tested in West Africa.

On Mar. 16, 2015 the ReEBOV test produced by Corgenix Medical Corp. became the first test to be approved for EBOV diagnosis, albeit in an emergency situation. A field validation study of the ReEBOV test was recently published. The ReEBOV test is a chromatographic immunoassay designed for qualitative detection of VP40, one of the seven viral proteins which are synthesized in the infected cells in addition to the glycoprotein (GP), nucleoprotein (NP), the L-polymerase, VP24, VP30 and VP35.

The ReEBOV assay uses affinity purified, polyclonal antibody obtained from goats immunized with a recombinant VP40 antigen. Whole blood or plasma from individuals suspected of EBOV infection is used in the test that is conducted as a dipstick immunoassay. If present in the sample, the EBOV VP40 antigen forms complexes with the anti-EBOV VP40 antibody conjugated to gold nanoparticles. This step generates a pink to red signal and provides a visual positive readout.

In an immunoassay, the detection antibody is responsible for the sensitivity, specificity, and/or selectivity of the assay. The full production cycle of polyclonal antibodies from goats, which are used when large amounts of antiserum is required, is approximately eighty (80) days. However, polyclonal IgG antibodies cannot be produced by cell lines and must be produced each time in the animal. The amounts of antibodies and their specificity and selectivity cannot be predicted or modified in a rational way. Polyclonal antibodies are also relatively unstable.

For example, ReEBOV kits should be kept at 4° C. to keep the antibody stable, and thus, requires a cold transport chain. Antibody production, storage, and transport costs are a significant portion of the cost associated with any diagnostic kit, including the ReEBOV kits. Nonetheless, the results of a recent Lancet published validation study and an independent WHO study differ significantly, but both studies suggest a significant level of false positive readouts are obtained by the ReEBOV kits.

Described herein is an innovative approach which uses proven technology to overcome virtually all of the limitations that stem from the use of natural polyclonal antibodies in diagnostic, therapeutic, or research kits. The present disclosure describes replacement of polyclonal antibodies with recombinant, synthetic Fragment antigen-binding proteins (Fabs) generated using a phage display system. This technology offers numerous advantages over the canonical production of polyclonal antibodies. In particular, the present disclosure describes the elucidation and manipulation of the molecular architecture of the EBOV Nucleoprotein as a significant advancement in the efforts to aid the development of recombinant Fab antibodies directed to bind to the EBOV NP antigen. The antibodies described herein provide a key mechanism to begin to effectively treat the EBOV epidemic in West Africa and other effected parts of the world.

SUMMARY OF THE INVENTION

The present disclosure provides for an antibody that specifically binds to the Nucleoprotein of Ebola virus, or a binding fragment thereof, wherein said antibody comprises, consists of, or consists essentially of complementarity determining region (CDR) sequences selected from one of the following sets: a) SEQ ID NO: 57, SEQ ID NO: 34, SEQ ID NO: 121, and SEQ ID NO: 35; b) SEQ ID NO: 127, SEQ ID NO: 128, SEQ ID NO: 126, and SEQ ID NO: 129; c) SEQ ID NO: 63, SEQ ID NO: 131, SEQ ID NO: 130, and SEQ ID NO: 132; d) SEQ ID NO: 43, SEQ ID NO: 96, SEQ ID NO: 145, and SEQ ID NO: 35; e) SEQ ID NO: 95, SEQ ID NO: 96, SEQ ID NO: 94, and SEQ ID NO: 97; and f) SEQ ID NO: 105, SEQ ID NO: 51, SEQ ID NO: 104, and SEQ ID NO: 106. In one embodiment, the antibody, consists of, or consists essentially of complementarity determining region (CDR) sequences selected from one of the following sets: a) SEQ ID NO: 105, SEQ ID NO: 51, SEQ ID NO: 104, and SEQ ID NO: 106; and b) SEQ ID NO: 43, SEQ ID NO: 96, SEQ ID NO: 145, and SEQ ID NO: 35. Any antibody of the present disclosure may be labeled with a detectable moiety.

The antibody of the present disclosure may be a monoclonal antibody, a chimeric antibody, a fragment binding protein (Fab), or a recombinant antibody. A recombinant antibody of the present disclosure may also have a variant Fc domain. The antibody may bind to the C-terminal domain of the Nucleoprotein of an Ebola virus strain selected from the group consisting of Tai Forest, Sudan, Bundibugyo, Reston, and Zaire. In one embodiment, the antibody may also bind to an amino acid sequence selected from the group consisting of SEQ ID NO: 1, SEQ ID NO: 2, SEQ ID NO: 3, SEQ ID NO: 4, and SEQ ID NO: 5.

In one embodiment the antibody of the present disclosure comprises, consists of, or consists essentially of a heavy chain sequence of SEQ ID NO: 210 and a light chain of SEQ ID NO: 211 or comprises, consists of, or consists essentially of a heavy chain of SEQ ID NO: 212 and a light chain of SEQ ID NO: 213. In an additional embodiment, the antibody may be a Fab fragment consisting of a heavy chain sequence of SEQ ID NO: 210 and a light chain of SEQ ID NO: 211. In a further embodiment, the antibody may be a Fab fragment consisting of a heavy chain sequence of SEQ ID NO: 212 and a light chain of SEQ ID NO: 213. The antibody may specifically bind to the Nucleoprotein of Ebola virus, or a binding fragment thereof, wherein the complementarity determining regions comprise one or more amino acid sequences selected from the group consisting of SEQ ID NO: 105, SEQ ID NO: 51, SEQ ID NO: 104, SEQ ID NO: 106, SEQ ID NO: 35, SEQ ID NO: 145, SEQ ID NO: 96, and SEQ ID NO: 43.

The present disclosure also provides an antibody that binds to a recombinantly expressed Ebola virus Nucleoprotein domain selected from the group consisting of SEQ ID NO: 1, SEQ ID NO: 2, SEQ ID NO: 3, SEQ ID NO: 4 and SEQ ID NO: 5, wherein the CDRs of said antibody bind to noncontiguous regions of said protein domain. The antibody of the present disclosure may also be isolated using a phage display library.

Further embodiments of the present disclosure include a diagnostic kit comprising the antibody described herein and reagents for detecting the binding of the antibody to its target antigen. Additionally, an embodiment of the present disclosure comprises a pharmaceutical composition comprising the antibody of the present disclosure, and a pharmaceutically acceptable carrier, excipient, or diluent. IN another embodiment a method of treating an infection in a patient is provided comprising administering of a composition comprising the antibody of the present disclosure to the patient. In a further embodiment, a method of detecting a viral protein in a biological sample is provided, wherein the method comprises 1) reacting the biological sample with the antibody of the present disclosure, and 2) detecting the Nucleoprotein of a viral cell in the biological sample. In another embodiment, a test strip for detecting Ebola virus is provided, wherein said test strip comprises a solid support; and an antibody of the present disclosure, optionally wherein said antibody is immobilized on the surface of the solid support.

BRIEF DESCRIPTION OF THE DRAWINGS

A brief description of the drawings is provided as follows.

FIG. 9A is a sequence representation of the location of CDR peptide sequences on the heavy chain amino acid sequence of Fab 20.

FIG. 9B is a sequence representation of the location of CDR peptide sequences on the light chain amino acid sequence of Fab 20.

FIG. 10A is a sequence representation of the location of CDR peptide sequences on the heavy chain amino acid sequence of Fab 6.

FIG. 10B is a sequence representation of the location of CDR peptide sequences on the light chain amino acid sequence of Fab 6.

DETAILED DESCRIPTION

Definitions

Figure 1:
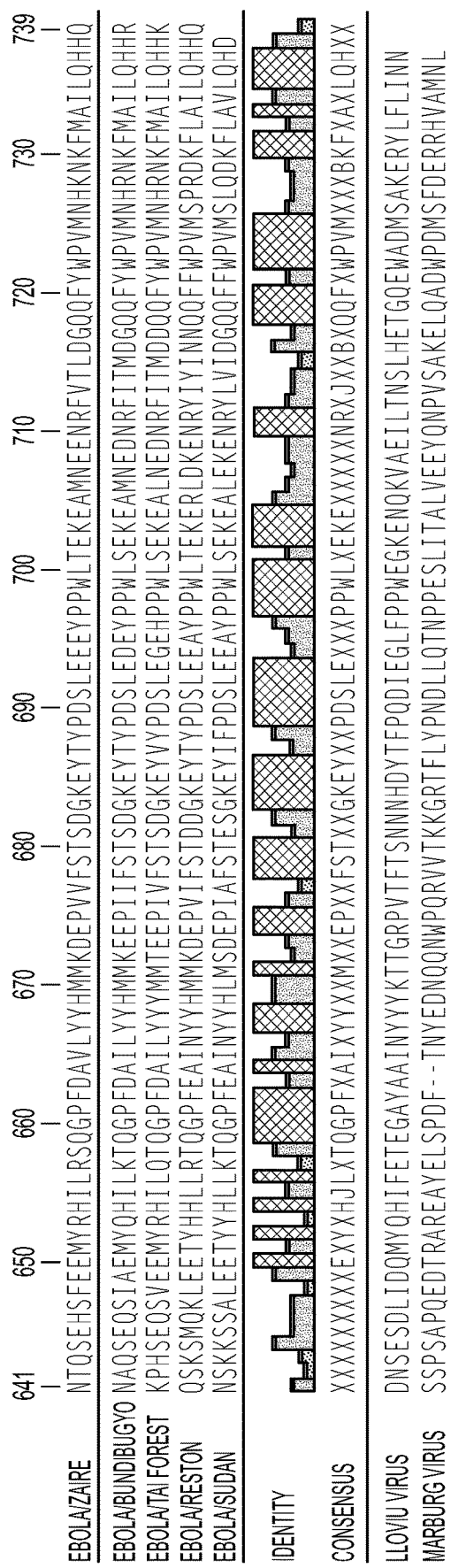
FIG. 1 is a graphical schematic showing the amino acid conservation in the NP$^{Ct}$ domain among Filoviridae. Eboal/Zaire: SEQ ID NO: 5; Eboal/Bundibugo: SEQ ID NO: 3; Eboal/Tai Forest: SEQ ID NO: 1; Eboal/Reston: SEQ ID NO: 4; Eboal/Sudan: SEQ ID NO: 2; Lloviu virus: SEQ ID NO: 216; Marburg virus: SEQ ID NO: 217.

The disclosures of each and every patent, patent application, and publication cited herein are hereby incorporated herein by reference in their entirety. In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

As used herein, the term "adjuvant" refers to a substance that elicits an enhanced immune response when used in combination with a specific antigen.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

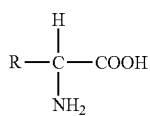

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an amino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies may be intact immunoglobulins derived from natural sources or from recombinant sources and may be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

The term "antibody" refers to polyclonal and monoclonal antibodies and derivatives thereof (including chimeric, synthesized, humanized and human antibodies), including an entire immunoglobulin or antibody or any functional fragment of an immunoglobulin molecule which binds to the target antigen and or combinations thereof. Examples of such functional entities include complete antibody molecules, antibody fragments, such as $F_v$, single chain $F_v$, complementarity determining regions (CDRs), $V_L$ (light chain variable region), $V_H$ (heavy chain variable region), Fab, F(ab')$_2$ and any combination of those or any other functional portion of an immunoglobulin peptide capable of binding to target antigen.

Antibodies exist, e.g., as intact immunoglobulins or as a number of well characterized fragments produced by digestion with various peptidases. Thus, for example, pepsin digests an antibody below the disulfide linkages in the hinge region to produce F(ab')$_2$ a dimer of Fab which itself is a light chain joined to $V_H$—$C_{H1}$ by a disulfide bond. The F(ab')$_2$ may be reduced under mild conditions to break the disulfide linkage in the hinge region, thereby converting the F(ab')$_2$ dimer into an Fab$_1$ monomer. The Fab$_1$ monomer is essentially an Fab with part of the hinge region. While various antibody fragments are defined in terms of the digestion of an intact antibody, one of ordinary skill in the art will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

The term "single chain antibody" refers to an antibody wherein the genetic information encoding the functional fragments of the antibody is located in a single contiguous length of DNA. For a thorough description of single chain antibodies.

The term "humanized" refers to an antibody wherein the constant regions have at least about 80% or greater homology to human immunoglobulin. Additionally, some of the nonhuman, such as murine, variable region amino acid residues may be modified to contain amino acid residues of human origin.

Humanized antibodies have been referred to as "reshaped" antibodies. Manipulation of the complementarity-determining regions (CDR) is a way of achieving humanized antibodies as described in Jones, et al., Nature 321:522 (1988), Riechmann, et al., Nature 332:323 (1988), and Winter & Milstein, Nature 349:293 (1991).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen may be derived from organisms, subunits of proteins/antigens, killed or inactivated whole cells or lysates.

"Antimicrobial" as used herein, includes antibacterial, antifungal, and antiviral agents.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, sputum, mucus, phlegm, tissues, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. One of skill in the art will understand the type of sample needed.

A "biomarker" or "marker" is a specific biochemical in the body which has a particular molecular feature that makes it useful for measuring the progress of disease or the effects of treatment, or for measuring a process of interest.

The term "cancer", as used herein, is defined as proliferation of cells whose unique trait (loss of normal controls) results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to a molecule of interest.

The term "cell surface protein" means a protein found where at least part of the protein is exposed at the outer aspect of the cell membrane. Examples include growth factor receptors.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp As used herein, a "derivative" refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, in one embodiment, the term "diagnosis" refers to detecting aberrant ALCAM expression due to cancers expressing ALCAM. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, may be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" component is a component in a form in which it exhibits a property by which it is characterized. For example, a functional enzyme is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences may be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is also incorporated into the NBLAST and XBLAST programs of Altschul, et al. (1990, J. Mol. Biol. 215:403-410), and may be accessed, for example at the National Center for Biotechnology Information (NCBI) world wide web site having the universal resource locator using the BLAST tool at the NCBI website. BLAST nucleotide searches may be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches may be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST may be utilized as described in Altschul et al. (1997, Nucleic Acids Res. 25:3389-3402). Alternatively, PSI-Blast or PHI-Blast may be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) may be used.

The percent identity between two sequences may be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

As used herein, an "instructional material" includes a publication, a recording, a diagram, or any other medium of expression which may be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated protein" refers to an amino acid sequence peptide, segment, or fragment which has been separated from sequences which flank it in a naturally occurring state, such as the amino acid sequences adjacent to the fragment in a genome in which it naturally occurs. The term also applies to proteins which have been substantially purified from other components which naturally accompany the protein, e.g., RNA or DNA which naturally accompany it in the cell. The term therefore includes, for example, a recombinant protein which is incorporated into a vector, into an autonomously replicating plasmid or virus, or into the genome of a prokaryote or eukaryote, or which exists as a separate molecule (e.g., as a synthetic, recombinant, chimeric, etc. protein) independent of other sequences. It also includes a recombinant protein which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that may be used to determine specific immunoreactivity of the antibodies of the present disclosure.

As used herein, the term "linkage" refers to a connection between two groups. The connection may be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

The term "measuring the level of expression" or "determining the level of expression" as used herein refers to any measure or assay which may be used to correlate the results of the assay with the level of expression of a gene or protein of interest. Such assays include measuring the level of mRNA, protein levels, etc. and may be performed by assays such as northern and western blot analyses, binding assays, immunoblots, etc. The level of expression can include rates of expression and may be measured in terms of the actual amount of an mRNA or protein present. Such assays are coupled with processes or systems to store and process information and to help quantify levels, signals, etc. and to digitize the information for use in comparing levels.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides or to peptides shorter than the full length native or mature protein.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative may be combined and which, following the combination, may be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" mean a non-naturally occurring peptide or polypeptide. Synthetic peptides or polypeptides may be synthesized, for example, using an automated polypeptide synthesizer. Various solid phase peptide synthesis methods are known to those of skill in the art.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers may be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups of the present application.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. A "significant detectable level" is an amount of contaminate that would be visible in the presented data and would need to be addressed/explained during analysis of the forensic evidence.

"Recombinant protein or "recombinant polypeptide" refers to a protein or polypeptide having sequences that are not naturally joined together. An amplified or assembled recombinant polypeptide or protein may be included in a suitable vector, and the vector may be used to transform a suitable host cell. A recombinant polypeptide or protein may serve a non-coding function (e.g., promoter, origin of replication, ribosome-binding site, etc.) as well. A "recombinant polypeptide" is one which is produced upon expression of a recombinant polynucleotide.

The term "regulate" refers to either stimulating or inhibiting a function or activity of interest.

A "sample," as used herein, refers preferably to a biological sample from a subject for which an assay or other use is needed, including, but not limited to, normal tissue samples, diseased tissue samples, sputum, mucus, phlegm, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. A sample can also be any other source of material obtained from a subject who contains cells, tissues, or fluid of interest. A sample can also be obtained from cell or tissue culture.

As used herein, the term "secondary antibody" refers to an antibody that binds to the constant region of another antibody (the primary antibody).

As used herein, the term "solid support" relates to a solvent insoluble substrate that is capable of forming linkages (preferably covalent bonds) with various compounds. The support may be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it may be a known standard agent or compound which is administered and used for comparing results when administering a test compound, or it may be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity may be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

The phrase "suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

The term to "treat," as used herein, means reducing the frequency with which symptoms are experienced by a patient or subject or administering an agent or compound to reduce the frequency with which symptoms are experienced.

The phrase "undesirable degradation," as used herein encompasses any type of enzymatic, chemical or biochemical breakdown of the compound at its termini which is likely to affect the function of the compound, such as sequential degradation of the compound at a terminal end thereof.

By the term "vaccine," as used herein, is meant a composition which when inoculated into a subject has the effect of stimulating an immune response in the subject, which serves to fully or partially protect the subject against a condition, disease or its symptoms. In one aspect, the condition is cancer. The term vaccine encompasses prophylactic as well as therapeutic vaccines. A combination vaccine is one which combines two or more vaccines, or two or more compounds or agents.

A "variant", as described herein, refers to a segment of DNA that differs from the reference DNA. A "marker" or a "polymorphic marker", as defined herein, is a variant. Alleles that differ from the reference are referred to as "variant" alleles.

A "vector" is a composition of matter which comprises an isolated nucleic acid and which may be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression may be supplied by the host cell or in an in vitro expression system. Expression vectors include all those known in the art, such as cosmids, plasmids (e.g., naked or contained in liposomes) and viruses that incorporate the recombinant polynucleotide.

Peptide Preparation, Modification, and Purification

The proteins and peptides of the present invention may be readily prepared by standard, well-established chemical or biological techniques, such as Solid-Phase Peptide Synthesis (SPPS) as described by Stewart et al. in *Solid Phase Peptide Synthesis,* 2nd Edition, 1984, Pierce Chemical Company, Rockford, Ill. and as described by Bodanszky and Bodanszky in *The Practice of Peptide Synthesis,* 1984, Springer-Verlag, New York. It will be appreciated that the proteins or peptides of the present disclosure may incorporate amino acid residues which are modified without affecting protein functional activity. For example, the N- and C-termini may be derivatized to include blocking groups, which are chemical substituents suitable to protect and/or stabilize the N- and C-termini from undesirable degradation. Blocking groups include protecting groups conventionally used in the art of peptide chemistry which will not adversely affect the in vivo activities of the protein or peptide.

For example, a suitably protected amino acid residue may be attached through its carboxyl group to a derivatized, insoluble polymeric support, such as cross-linked polystyrene or polyamide resin. Stepwise synthesis of the oligopeptide is carried out by the removal of the N-protecting group from the initial amino acid, and coupled thereto with the carboxyl end of the next amino acid in the sequence of the desired peptide. This next amino acid should also be suitably protected. The carboxyl of the incoming amino acid may be activated to react with the N-terminus of the support-bound amino acid by formation into a reactive group, such as formation into a carbodiimide, a symmetric acid anhydride, or an "active ester" group, such as a hydroxybenzotriazole or a pentafluorophenly ester.

Exemplary SPPS methods include, but are not limited to, 1) a method that utilizes tert-butyloxycarbonyl (BOC) as the α-amino protecting group and 2) a method which utilizes 9-fluorenylmethyloxycarbonyl (FMOC) to protect the α-amino of the amino acid residues. Both the BOC and FMOC protein biosynthesis methods are known to those of ordinary skill in the art. Incorporation of N- and/or C-blocking groups can also be achieved using protocols conventional to SPPS methods.

For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide.

Similarly, incorporation of an N-methylamine blocking group at the C-terminus is achieved using N-methylaminoethyl-derivatized DVB, resin, which upon HF treatment releases a peptide bearing an N-methylamidated C-terminus.

Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, may be used for this purpose, with cleavage from the support being effected by TFA in dicholoromethane. Esterification of the suitably activated carboxyl function e.g.

with DCC, can then proceed by addition of the desired alcohol, followed by deprotection and isolation of the esterified peptide product.

Incorporation of N-terminal blocking groups may be achieved while the synthesized peptide is still attached to the resin, for instance by treatment with a suitable anhydride and nitrile. To incorporate an acetyl blocking group at the N-terminus, for instance, the resin-coupled peptide may be treated with 20% acetic anhydride in acetonitrile. The N-blocked peptide product can then be cleaved from the resin, deprotected and subsequently isolated.

Suitable N-terminal blocking groups may be introduced to the protein by alkylation or acylation of the N-terminus. Examples of suitable N-terminal blocking groups include, but are not limited to, $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside.

Suitable C-terminal blocking groups, in which the carboxyl group of the C-terminus is either incorporated or not, includes esters, ketones, or amides. Ester or ketone-forming alkyl groups particularly include lower alkyl groups such as methyl, ethyl, and propyl, and amide-forming amino group, such as primary amines (—$NH_2$). Additional C-terminal blocking groups include, but are not limited to, mono- and di-alkylamino groups, such as methylamino, ethylamino, dimethylamino, diethylamino, methylethylamino, and the like. Decarboxylated amino acid analogues, such as agmatine, are also useful C-terminal blocking groups and may be either coupled to the C-terminal residue of the peptide or used in place of it. Further, it will be appreciated that the free amino and carboxyl groups at the N- or C-termini may be removed altogether from the protein or peptide to yield desamino and decarboxylated forms thereof without effect on peptide activity.

Addition of salts to the protein and peptides of the present disclosure is an additional embodiment of the present invention. The salt may be added to the protein or peptide by any means known in the art, but particularly by acid. Thus, a peptide in accordance with the present invention may be treated with an inorganic acid, such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like. Thus, a salt of the peptide is suitable for use in the invention, particularly a water soluble salt.

The present invention also provides for analogs and/or derivatives of the proteins and peptides described herein. Analogs and derivatives may differ from naturally occurring proteins or peptides by conservative amino acid sequence differences, by modifications which do not affect protein sequence, or by both. For example, conservative amino acid changes may be made, which although they alter the primary amino acid sequence of the protein or peptide, do not alter the normal function of the peptide or protein. To that end, about ten or more conservative amino acid changes typically have no effect on protein or peptide function or activity.

Modifications which do not normally alter primary sequence include in vivo or in vitro chemical derivatization of polypeptides, such as acetylation or carboxylation. Modifications of present disclosure include glycosylation, such as those changes made by modifying the glycosylation patterns of a polypeptide during its synthesis and processing. Alternatively, the polypeptide may be synthesized in further processing steps; such as by exposing the polypeptide to enzymes which affect glycosylation, including, but not limited to, mammalian glycosylating or deglycosylating enzymes. Modifications also include sequences which have phosphorylated amino acid residues, such as phosphotyrosine, phosphoserine, or phosphothreonine.

Further modifications of the present disclosure include, but are not limited to, polypeptides which have been modified using ordinary molecular biological techniques so as to improve their resistance to proteolytic degradation, to optimize solubility properties, or to render them more suitable as a therapeutic agent. Analogs of such polypeptides include those containing residues other than naturally occurring L-amino acids, such as D-amino acids or non-naturally occurring or non-standard synthetic amino acids. All protein or peptide fragments of the present disclosure may be synthetically synthesized so as to be non-naturally occurring. The peptides of the invention are not limited to products of any of the specific exemplary processes listed herein.

Other peptide modifications can also be incorporated without adversely affecting the protein activity. These modifications may include, but are not limited to, substitution of one or more of the amino acids in the natural L-isomeric form with amino acids in the D-isomeric form. Thus, the peptide may include one or more D-amino acid resides, or may comprise amino acids which are all in the D-isomer form. Retro-inverso forms of peptides in accordance with the present invention are also contemplated. For example, inverted peptides in which all amino acids are substituted with D-amino acid forms are encompassed by the present disclosure.

As previously described, modifications or optimizations of peptide ligands of the present invention are within the scope of the application. Modified or optimized proteins and peptides are included within the definition of peptide binding ligand. Specifically, a peptide sequence identified may be modified to optimize its potency, pharmacokinetic behavior, stability and/or other biological, physical and chemical properties.

To ensure that the protein or peptide obtained from either chemical or biological synthesis techniques are the desired protein or peptide, analysis of the peptide composition should be conducted. For example, amino acid composition analysis may be conducted using high resolution mass spectrometry to determine the molecular weight of the peptide. Alternatively or additionally, the amino acid content of the peptide may be confirmed by hydrolyzing the peptide in aqueous acid, and then separating, identifying, and quantifying the amino acid components of the mixture using high-pressure liquid chromatography (HPLC) or an amino acid analyzer. Protein sequenators, instruments that sequentially degrade the peptide and identify the amino acids and their order, may also be used to definitely characterize the sequence of the peptide.

Prior to its use, the protein or peptide may be purified to remove contaminants. An immunological, enzymatic, or other type of assay may be used to monitor and/or confirm protein purification at each stage in the procedure. In this regard, it will be appreciated that the protein or peptide fragment may be purified to meet the standards set out by the appropriate regulatory agencies. Protein purification methods are well known in the art, and are described, for example in Deutscher et al. (ed., 1990, *Guide to Protein Purification*, Harcourt Brace Jovanovich, San Diego).

Any one of a number of conventional purification procedures may be used to attain the required level of purity including, for example, reversed-phase HPLC using an alkylated silica columns, such as $C_4$-, $C_8$-, or $C_{18}$-silica columns. Alternatively, a gradient mobile phase of increasing organic content may be used to achieve protein purification. For example, acetonitrile in an aqueous buffer usually containing a small amount of trifluoroacetic acid may be used to purify proteins. Ion-exchange chromatography may also be used to separate and/or purify proteins and peptides based on their charge.

Amino Acid Substitutions

In certain embodiments, the disclosed compositions and methods may involve preparing proteins or peptides with one or more substituted amino acid residues. In various embodiments, the structural, physical and/or therapeutic characteristics of the peptide sequences described herein may be optimized by replacing one or more amino acid residues. The skilled artisan will be aware that, in general, amino acid substitutions in a parent or initial peptide typically involve the replacement of an amino acid with another amino acid of relatively similar properties (i.e., conservative amino acid substitutions). The properties of the various amino acids and effect of amino acid substitution on protein structure, function, and activity has been the subject of extensive study and knowledge in the art. The compositions and methods of the present disclosure may include the following isosteric and/or conservative amino acid changes in a parent polypeptide sequence with the expectation that the resulting polypeptides would have a similar or improved property profile as described above:

Substitution of Alkyl-Substituted Hydrophobic Amino Acids

A substitution of alkyl-substituted hydrophobic amino acids comprises, consists essentially of, or consist of alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of Aromatic-Substituted Hydrophobic Amino Acids

A substitution of aromatic-substituted hydrophobic amino acids comprises, consists essentially of, or consist of phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3'-, or 4'-methyl-2, 3 or 4-biphenylalanine, and 2- or 3-pyridylalanine.

Substitution of Amino Acids Containing Basic Functions

A substitution of amino acids containing basic functions comprises, consists essentially of, or consist of arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of Acidic Amino Acids

A substitution of acidic amino acids comprises, consists essentially of, or consist of aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of Side Chain Amide Residues

A substitution of side chain amide residues comprises, consists essentially of, or consists of asparagine, glutamine, and alkyl or aromatic substituted derivatives of asparagine or glutamine.

Substitution of Hydroxyl Containing Amino Acid

A substitution of hydroxyl containing amino acid comprises, consists essentially of, or consist of serine, threonine, homoserine, 2,3-diaminopropionic acid, and alkyl or aromatic substituted derivatives of serine or threonine. It is also understood that the amino acids within each of the categories listed above may be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). While any amino acid with any range of hydropathic indices may be used, in making conservative amino acid substitutions of the present invention, the use of amino acids whose hydropathic indices ranging from about 2 to about −2 is preferred, within from about 1 to about −2 are more preferred, and within from about 0.5 to about −0.5 are even more preferred.

Amino acid substitutions may also take into account the hydrophilicity of the amino acid residue. Hydrophilicity values in the present disclosure have been assigned to amino acid residues as follows: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). While any amino acid with any range of hydrophilic indices may be used, amino acid substitutions employing replacement of amino acids with other amino acids of similar hydrophilicity is preferred.

Other considerations of substituting amino acids in the proteins and peptides of the present disclosure include the size of the amino acid side chain. For example, it would generally not be preferred to replace an amino acid with a compact side chain, such as glycine or serine, with an amino acid with a bulky side chain, such as tryptophan or tyrosine.

The effect of various amino acid residues on protein secondary structure is also a consideration. Through empirical study, the effect of different amino acid residues on the tendency of protein domains to adopt an alpha-helical, beta-sheet, or reverse turn secondary structure has been determined and is known in the art. Based on such considerations and extensive empirical study, tables of conservative amino acid substitutions have been constructed and are known in the art, such as arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. Conservative substitutions for interior residues would include, but are not limited to: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). Conservative substitutions for solvent-exposed or hydrophilic residues would include, but are not limited to: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various computational matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues. Methods of substituting any amino acid for any other amino acid in an encoded peptide sequence are known by the skilled artisan, for example by the technique of site-directed mutagenesis or by synthesis and assembly of oligonucleotides encoding an amino acid substitution and splicing into an expression vector construct.

Compositions of the Present Disclosure

The identification and characterization of the boundaries of the globular N-terminal and C-terminal domains in Ebola virus (EBOV) Nucleoprotein, also called the Nucleoprotein (NP), the overexpression of these protein domains in *Escherichia coli* (*E. coli*), and the structural determination of two crystal forms of the C-terminal domain spanning specific amino acid residues are described herein. The proteins and peptide fragments of the present invention are useful to generate antibodies directed against the protein or peptide sequence to elicit an immune response in a subject, such as a human or a veterinary animal patient.

For example, in one embodiment of the present disclosure, the protein and peptide fragments described herein may be targeted to bind to antibodies. In one embodiment the present disclosure is directed to an antibody that has been isolated from a synthetic library of antibodies, wherein the antibody specifically binds to an Ebola virus protein C-terminal domain of the Nucleoprotein. More particularly, the antibody binds to one or more of recombinantly expressed sequences selected from the group consisting of SEQ ID NO: 1, SEQ ID NO: 2, SEQ ID NO: 3, SEQ ID NO: 4, and SEQ ID NO: 5. In one embodiment the antibody binds to the recombinantly expressed sequence of SEQ ID NO: 5. In one embodiment the protein is expressed using a prokaryotic host cell such as *E coli*. In accordance with one embodiment, the synthetic antibody binds to a recombinantly expressed Ebola virus Nucleoprotein domain selected from the group consisting of SEQ ID NO: 1, SEQ ID NO: 2, SEQ ID NO: 3, SEQ ID NO: 4 and SEQ ID NO: 5, wherein the CDRs of said antibody bind to noncontiguous regions of said protein domain. In accordance with one embodiment the antibody is a Fab fragment isolated from an antibody expression library, optionally a phage display library. The method of isolating said antibodies comprises the steps of expressing the recombinant protein domain and recovering the expressed protein; contacting the expressed protein, under conditions that allow for secondary and tertiary structure formation of the expressed protein domain, with antibodies from the antibody expression library; identifying antibodies that specifically bind to the folded protein domains; and isolating the identified antibodies.

The antibodies of the present disclosure may be used as therapeutic, diagnostic, prognostic, or research tools. For example, the antibodies may be comprised in a therapeutic or pharmaceutical composition, as well as a diagnostic, prognostic, or research assay kit. In one embodiment a kit is provided comprising one or more Ebola virus Nucleoprotein domain binding antibodies as disclosed herein for use in detecting the presence of Ebola virus in a biological sample.

The kit of the present disclosure may also comprise the protein, peptide, or antibody compositions of the invention for ex vivo use. The kit of the present disclosure may comprise the protein, peptide, or antibody compositions of the present invention being administered to a cell or a tissue of a subject ex vivo. In some embodiments, the kit may also comprise a therapeutic compound or pharmaceutical composition as described herein.

In another embodiment, the kit comprises a solvent suitable for dissolving or suspending the composition of the invention prior to administering the compound to the subject. Preferably, the solvent is sterile. Finally, the kit may comprise instructional material that may describe how to effectively administer the protein, peptide, or antibody compositions of the present invention to a subject in order to effectively diagnose, prognose, or research a disease, disorder, or infection, particularly Ebola virus.

In additional embodiments, the kit may comprise the protein, peptide, or antibody compositions of the present invention in metal or plastic foil, a blister pack, a dispenser device, or a test strip. The protein, peptide, or antibody compositions of the present invention may also be comprised in an applicator, tubes, and/or buffers. The kit may also comprise instructions for administration.

The various reagent components of the kits may be present in separate containers, or some or all of them may be pre-combined into a reagent mixture in a single container, as desired. The dispenser device or applicator may also be accommodated by a notice associated with the kit container in a form prescribed by a governmental agency regulating the manufacture, use or sale of pharmaceuticals. Typically, the notice would indicate approval by the federal agency of the form of the compositions or human or veterinary administration. Such notice, for example, may be of labeling approved by the U.S. Food and Drug Administration for prescription drugs or of an approved product insert. Accordingly, compositions of the present invention may be presented in a pack or dispenser device, such as an FDA approved kit, which may contain one or more unit dosage forms containing the therapeutic compound as described herein.

In an illustrative embodiment, the protein or peptide target of the antibody of the present disclosure is the protein of the Ebola virus Nucleoprotein. In another embodiment, the protein or peptide target is a C-terminal domain of the Ebola virus, in particular, the C-terminus of the Ebola virus nucleoprotein. Thus, the present disclosure provides therapeutics and pharmaceutical compositions, in addition to diagnostic, prognostic, and research assay kits comprising antibodies that are directed to the Ebola virus proteins and peptide fragments described herein.

In one specific embodiment, an inhibitor of Ebola virus nucleoprotein levels or activity is an antibody directed against the nucleoprotein or a peptide fragment disclosed therein. In particular, antibodies having therapeutic applications may involve blocking or inhibiting the Nucleoprotein (NP) of the Ebola virus. In one aspect of the present disclosure, an antibody of the invention includes, but is not limited to, a monoclonal antibody, a polyclonal antibody, a single chain antibody, a synthetic antibody, a humanized antibody, a recombinant antibody, and a chimeric antibody, and biologically active peptide fragments and homologs thereof. In one particular embodiment, the antibody is a monoclonal antibody.

The antibodies disclosed herein can be expressed as one or more recombinant antibodies comprising a variant Fc region, wherein the variant Fc region comprises at least one amino acid modification relative to the corresponding native Fc region. In one embodiment the Fc region comprises a mutation of the naturally occurring amino acid residue at position 329 and at least one further mutation of at least one amino acid selected from the group comprising amino acid residues at position 228, 233, 234, 235, 236, 237, 297, 318, 320, 322 and 331 to a different residue, wherein the residues in the Fc region are numbered according to the EU index of Kabat.

The altering of the amino acid residues results in an altering of the effector function of the Fc region compared to the non-modified (wild-type) Fc region. In one embodiment, the human Fc region is a human Fc region of the human IgG1 isotype or of the human IgG4 isotype.

In one embodiment, the at least one further mutation of at least one amino acid in the Fc-region is S228P, E233P, L234A, L235A, L235E, N297A, N297D, and/or P331S. In another embodiment, the human IgG1 isotype comprises a mutation in the Fc region selected from L234A and L235A. In a further embodiment, the human IgG4 isotype comprises a mutation in the Fc region selected from S228P and L235E.

In yet another embodiment, the antibody of the present disclosure comprises, consists of, or consists essentially of a Fragment antigen binding protein (Fab). In another embodiment, the Fab is a peptide or protein fragment of the Ebola virus. In a further embodiment, the Fab is a peptide or protein fragment located in the Ebola virus Nucleoprotein. In a yet further embodiment, the Fab is a peptide or protein fragment located in the C-terminal or N-terminal domain of the Ebola virus Nucleoprotein. In particular, the Fab is a peptide or protein fragment located in the C-terminal domain of the Ebola virus Nucleoprotein. Illustrative embodiments of the Fab proteins of the present disclosure comprise Fab 6 and Fab 20.

In an additional embodiment of the antibody of the present disclosure, Fab 6 or Fab 20 may comprise an amino acid sequence on the light protein chain and/or the heavy protein chain. In an illustrative embodiment, the Fab 20 heavy chain and light chain amino acids of the present disclosure comprise SEQ ID NO: 212 and SEQ ID NO: 213, respectively. An illustrative embodiment of the Fab 6 heavy chain and light chain amino acids of the present disclosure comprise SEQ ID NO: 210 and SEQ ID NO: 211, respectively.

In yet an additional embodiment, the Fabs of the present disclosure may comprise, consist of, or consist essentially of one or more complementarity determining regions (CDRs). More specifically, a Fab of the present disclosure may comprise at least one CDR. For example, Fab 6 and Fab 20 each comprise at least a single CDR of the present disclosure. In other embodiments, the Fab may comprise a plurality of CDRs. For example, Fab SEQ ID NOS: 210 and 212 each comprise three CDRs.

The CDRs of the present disclosure comprise, consist of, or consist essentially of about 3 to about 20 amino acids, and may be used to derive synthetic or recombinant antibodies, such as Fabs. More specifically, the Fabs of the present disclosure may have CDRs comprise, consist of, or consist essentially of from about 3 to about 18, from about 4 to about 16, from about 5 to about 15, from about 6 to about 14 amino acids. Table 1 describes the CDRs encompassed by the present disclosure, including all of SEQ ID NO: 6 to SEQ ID NO: 209.

Illustrative embodiments of the CDRS of the present disclosure include, but are not limited to the following: 1) ISYSSI (SEQ ID NO: 43), 2) SIYSYSGYTS (SEQ ID NO: 96), 3) SYWYHVGSWHYTGM (SEQ ID NO: 145), 4) SSSSLI (SEQ ID NO: 35), 5) VYYYYI (SEQ ID NO: 105), 6) SISPYYGYTS (SEQ ID NO: 51), 7) WSYDQSM-SYKSGM (SEQ ID NO: 104), AND 8) YSYSLV (SEQ ID NO: 106). In accordance with one embodiment an antibody or Fab is provided comprising a heavy chain sequence of (SEQ ID NO: 214)
EISEVQLVESGGGLVQPGGSLRLSCAASGFNX$_1$HWVRQAPGKGLEWVAX$_2$

YADSVKGRFTISADTSKNTAYLQMNSLRAEDTAVYYCARX$_3$DYWGQGTL

VTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTK

VDKKVEPKSCDKTHT and a light chain sequence of (SEQ ID NO: 215)
SDIQMTQSPSSLSASVGDRVTITCRASQSVSSAVAWYQQKPGKAPKWYSA

SSLYSGVPSRFSGSRSGTDFTLTISSLQPEDFATYYCQQX$_4$TFGQGTKVE

IKRTVAAPSVFIFPPSDSQLKSGTASVVCLLNNFYPREAKVQWKVDNALQ

SGNSQESVTEQDSKDSTYSLSSTLTLSKADYEKHKVYACEVTHQGLSSPV

TKSFNRGEC wherein X$_1$ is a HCR1 peptide selected from Table 1; X$_2$ is a HCR2 peptide selected from Table 1; X$_3$ is a HCR3 peptide selected from Table 1 and X$_4$ is a LCR1 peptide selected from Table 1. In one embodiment $X_1$ is a peptide selected from the group consisting of SEQ ID NO: 57, SEQ ID NO: 127, SEQ ID NO: 63, SEQ ID NO: 43, SEQ ID NO: 95, and SEQ ID NO: 105; $X_2$ is a peptide selected from the group consisting of SEQ ID NO: 34, SEQ ID NO: 128, SEQ ID NO: 131, SEQ ID NO: 96, SEQ ID NO: 96, and SEQ ID NO: 51; $X_3$ is a peptide selected from the group consisting of SEQ ID NO: 121, SEQ ID NO: 126, SEQ ID NO: 130, SEQ ID NO: 145, SEQ ID NO: 94 and SEQ ID NO: 104; and $X_4$ is a peptide selected from the group consisting of SEQ ID NO: 35, SEQ ID NO: 129, SEQ ID NO: 132, SEQ ID NO: 35, SEQ ID NO: 97, and SEQ ID NO: 106. In one embodiment $X_1$, $X_2$, $X_3$, and $X_4$, are selected from one of the following sets, respectively:

a) SEQ ID NO: 57, SEQ ID NO: 34, SEQ ID NO: 121, and SEQ ID NO: 35;

b) SEQ ID NO: 127, SEQ ID NO: 128, SEQ ID NO: 126, and SEQ ID NO: 129;

c) SEQ ID NO: 63, SEQ ID NO: 131, SEQ ID NO: 130, and SEQ ID NO: 132;

d) SEQ ID NO: 43, SEQ ID NO: 96, SEQ ID NO: 145, and SEQ ID NO: 35;

e) SEQ ID NO: 95, SEQ ID NO: 96, SEQ ID NO: 94, and SEQ ID NO: 97; and f) SEQ ID NO: 105, SEQ ID NO: 51, SEQ ID NO: 104, and SEQ ID NO: 106. More specifically, an embodiment of the antibody of the present disclosure comprises, consists of, or consists essentially of a heavy chain sequence of: EISEVQLVESGGGLVQPGGSLRLSCAASGFNX$_1$HW VRQAPGKGLEWVAX$_2$YADSVKGR FTISADTS KNTAYLQMNSLRAEDTAVYYCARX$_3$DYWGQGTLV TVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NOS: 214), and a light chain sequence of: SDIQMTQSPSSLSASVGDRVTITCRASQSVSSAVAWYQQKPGKAPKLLIYSASSLYSGV PSRFSGSRSGT DFTLTISSLQPEDFATYYCQQX$_4$TFGQGTKVEIKRTV AAPSVFIFPPSDSQ LKSGTASVVCLLNNFYPREAKVQWKVDNALQSGNSQESVTEQDSKDSTYSLSST LTLS KADYEKHKVYACEVTHQGLSSPVTKSFNRGEC (SEQ ID NOS: 215), wherein $X_1$ is SEQ ID NO: 43, $X_2$ is SEQ ID NO: 96, $X_3$ is selected from the group consisting of SEQ ID NO: 145, and $X_4$ is SEQ ID NO: 35, or $X_1$ is SEQ ID NO: 105, $X_2$ is SEQ ID NO: 51, $X_3$ is selected from the group consisting of SEQ ID NO: 104, and $X_4$ is SEQ ID NO: 106. In one embodiment an antibody is provided comprising a heavy chain sequence of SEQ ID NO: 212 or 210 and comprising a light chain sequence of SEQ ID NO: 211 or 213.

In one aspect, an antibody of the invention may be administered to a subject at a dosage from about 0.01 mg/kg to about 100 mg/kg, about 0.1 mg/kg to about 75 mg/kg, about 0.5 mg/kg to about 50 mg/kg, about 1.0 mg/kg to about 25 mg/kg, about 2.0 mg/kg to about 20 mg/kg, about 3.0 mg/kg to about 15 mg/kg, about 4.0 mg/kg to about 10 mg/kg, or about 5.0 mg/kg to about 7.5 mg/kg. The present invention further encompasses the administration of unit doses, which may be, for example, 1, 5, 10, 20, 25, 30, 35, 40, 45, 50, 55, 60, 65, 70, 75, 80, 85, 90, 95, 100, 125, 150, 200, 500, 1,000, or 5,000 mg. Numerical ranges recited herein by endpoints include all numbers and fractions subsumed within that range (e.g., 1 to 5 includes 1, 1.5, 2, 2.75, 3, 3.90, 4, and 5). All numbers and fractions thereof are presumed to be modified by the term "about."

TABLE 1

Complementarity Determining Region (CDR) Peptide Sequences of the Fab Protein Amino Acid Sequences

| CDR # | Heavy Chain CDR Region 1 (HC1) Amino Acids | SEQ ID NO: | CDR # | HC2 Amino Acids | SEQ ID NO: | CDR # | HC3 Amino Acids | SEQ ID NO: | CDR # | Light Chain CDR Region 3 (LC3) Amino Acids | Shows affinity to: E. Zaire NP | E. Marburg PA | E. Bundibugyo NP | E. Reston NP | E. Tai Forest NP | E. Sudan NP |

TABLE 1-continued

Complementarity Determining Region (CDR) Peptide Sequences of the Fab Protein Amino Acid Sequences

| CDR # | SEQ IN NO: | Heavy Chain CDR 1 (HC1) Amino Acids | CDR # | SEQ IN NO: | HC2 Amino Acids | CDR # | SEQ IN NO: | HC3 Amino Acids | CDR # | SEQ IN NO: | Light Chain CDR 3 (LC3) Amino Acids | Shows affinity to: | | | | | |
|---|---|---|---|---|---|---|---|---|---|---|---|---|---|---|---|---|---|
| | | | | | | | | | | | | E. Zaire NP | Marburg PA | E. Bundibugyo NP | E. Reston NP | E. Tai Forest NP | E. Sudan NP |
| 21 | 57 | FSSSSI | 92 | 34 | SISSSSGSTS | 163 | 76 | ESKYWYWLYYAI | 234 | 35 | SSSSLI | X | | | | | |
| 22 | 70 | FYSYSI | 93 | 8 | YISSSYGYTY | 164 | 77 | SPGYYMWDWWHGF | 235 | 78 | YYFKPI | X | | | | | |
| 23 | 26 | VSYSSI | 94 | 80 | SISPYYGSTS | 165 | 79 | SYPGYSWSSYFAL | 236 | 81 | YYWSLF | X | | | | | |
| 24 | 27 | FSYSSI | 95 | 83 | SIYSYSGSTS | 166 | 82 | YFLMPWRPGHYGM | 237 | 84 | SWWYPI | X | | | | | |
| 25 | 26 | VSYSSI | 96 | 86 | SISSSYGYTY | 167 | 85 | SYPWGYSYGFAL | 238 | 87 | YRGSLI | X | | | | | |
| 26 | 27 | FSYSSI | 97 | 89 | SISPYYGSTY | 168 | 88 | SYAYGQWGPRPAI | 239 | 90 | SYWSSSYLI | X | | | | | |
| 27 | 92 | VSYSYI | 98 | 8 | YIYSYGYTY | 169 | 91 | ESYLPVWWIFYGF | 240 | 93 | SYSYPI | X | | | | | |
| 28 | 95 | FSYSYI | 99 | 96 | SIYSYSGYTS | 170 | 94 | EYDGYYYYAAGYGI | 241 | 97 | YYSWYLl | X | | X | | X | |
| 29 | 57 | FSSSSI | 100 | 34 | SISSSSGSTS | 171 | 98 | QWWQYQGFQQAI | 242 | 35 | SSSSLI | X | | | | | |
| 30 | 58 | VYYSSI | 101 | 100 | SISSSYSYTS | 172 | 99 | NQWDPIYSYGGFAL | 243 | 36 | SVSGYLI | X | | X | | | |
| 31 | 43 | ISYSSI | 102 | 44 | YISPYYGSTS | 173 | 102 | SFPYYQTYGWYFAL | 244 | 103 | VGYCLPI | X | | | | | |
| 32 | 105 | VYYYYI | 103 | 51 | SISPYYGSTS | 174 | 104 | WSYDQSMSYKSGM | 245 | 106 | YSYSLV | X | | X | | X | |
| 33 | 39 | ISSSSI | 104 | 108 | YIYSSYGYTS | 175 | 107 | WWDSWYGGSTAI | 246 | 109 | YWYQPI | X | | | | | |
| 34 | 40 | IYYYSI | 105 | 96 | SIYSYSGYTS | 176 | 110 | SYTSSYSKYHGM | 247 | 111 | SWYPPL | X | | | | | |
| 35 | 113 | VSSSYI | 106 | 114 | SIYSYSGYTY | 177 | 112 | GYGSRWWYSGRGM | 248 | 115 | ASYHQGPL | | X | | | | |
| 36 | 26 | VSYSSI | 107 | 96 | SIYSYSGYTS | 178 | 116 | SYGFYYXARYGL | 249 | 117 | SSGHQLV | | X | | | | |
| 37 | 22 | VYSSSI | 108 | 119 | SISSSYGYTY | 179 | 118 | YERSYWGKGWAM | 250 | 120 | SWSSLV | | X | | | | |
| 38 | 57 | FSSSSI | 109 | 34 | SISSSSGSTS | 180 | 121 | YWWYAWPEDWYFAQAM | 251 | 35 | SSSSLI | X | | X | | X | |
| 39 | 123 | IYYYSI | 110 | 124 | SISSSGSTY | 181 | 122 | GYKVYYSYSSGI | 252 | 125 | IGWYPI | | | X | | | |
| 40 | 127 | LSSSSI | 111 | 128 | YIYPSSGSTS | 182 | 126 | HTWTYQGFFYAF | 253 | 129 | GGYALI | X | | X | | X | X |

TABLE 1-continued

Complementarity Determining Region (CDR) Peptide Sequences of the Fab Protein Amino Acid Sequences

| CDR # | SEQ IN NO: | Heavy Chain CDR 1 (HC1) Amino Acids | CDR # | SEQ IN NO: | HC2 Amino Acids | CDR # | SEQ IN NO: | HC3 Amino Acids | CDR # | SEQ IN NO: | Light Chain CDR Region 3 (LC3) Amino Acids | Shows affinity to: |||||||
|---|---|---|---|---|---|---|---|---|---|---|---|---|---|---|---|---|---|
| | | | | | | | | | | | | E. Zaire NP | Marburg PA | E. Bundibugyo NP | E. Reston NP | E. Tai Forest NP | E. Sudan NP |

TABLE 1-continued

Complementarity Determining Region (CDR) Peptide Sequences of the Fab Protein Amino Acid Sequences

| CDR # | SEQ IN NO: | Heavy Chain CDR 1(HC1) Amino Acids | CDR # | SEQ IN NO: | HC2 Amino Acids | CDR # | SEQ IN NO: | HC3 Amino Acids | CDR # | SEQ IN NO: | Light Chain CDR 3 (LC3) Amino Acids | Shows affinity to: | | | | | |
|---|---|---|---|---|---|---|---|---|---|---|---|---|---|---|---|---|---|
| | | | | | | | | | | | | E. Zaire NP | E. Marburg PA | E. Bundibugyo NP | E. Reston NP | E. Tai Forest NP | E. Sudan NP |
| 62 | 26 | VSYSSI | 133 | 185 | YIYSSYGSTS | 204 | 184 | GFWRYWMVRFGL | 275 | 186 | SYYRPI | X | | | | | |
| 63 | 27 | VYYSSI | 134 | 188 | YISSYYGSTY | 205 | 187 | GSDYYGQWGYAI | 276 | 189 | YQGSLI | X | | | | | |
| 64 | 22 | VYSSSI | 135 | 191 | SISPSYGSTY | 206 | 190 | GYGYYYSYKYGL | 277 | 192 | SVVKPL | X | | | | | |
| 65 | 194 | LSYSSI | 136 | 40 | SLYSYYGYTS | 207 | 193 | NAYNYYSGHAL | 278 | 195 | GSGSLF | X | | | | | |
| 66 | 57 | FSSSSI | 137 | 197 | SIYPYYGYTS | 208 | 196 | WKMIYYYHYVGM | 279 | 198 | YWIMSSPF | X | | | | | |
| 67 | 58 | VYYSSI | 138 | 60 | SISSYSGYTS | 209 | 199 | YSGQYYYRYSYAL | 280 | 200 | AWWSPF | X | | | | | |
| 68 | 59 | LYYSSI | 139 | 40 | SIYSYYGYTS | 210 | 201 | DYYYYFGWYSNAL | 281 | 202 | IYYYGLI | X | | | | | |
| 69 | 57 | FSSSSI | 140 | 34 | SISSSSGSTS | 211 | 203 | KGQYSPPYWHHRAM | 282 | 35 | SSSSLI | X | | | | | |
| 70 | 26 | VSYSSI | 141 | 205 | YIYSSSGYRS | 212 | 204 | SLSSSYYSNWYWGL | 283 | 206 | NYGGLI | X | | | | | |
| 71 | 26 | VSYSSI | 142 | 208 | YISSYYGSTS | 213 | 207 | SYYPMYYISKPAI | 284 | 209 | YQGSLI | X | | | | | |

In another embodiment, the crystal protein structure provided herein may be a target epitope for an antibody of the present invention, which may be comprised in a therapeutic or pharmaceutical composition, as well as a diagnostic, prognostic, or research assay kits. The crystal protein structure described herein comprises, consists of, and consists essentially of the Fabs and CDRs as described herein, notably, the specific Fabs and CDRs SEQ ID NOS described above. The Fabs and CDRs described herein may not be contiguous or juxtaposed on the primary (linear), secondary, or tertiary protein structures. Thus, one or more specific antibody binding epitopes on the Nucleoprotein may not be side-by-side in the various protein isomers. Based on the protein crystal structure, rational design of chemical compounds and antibody therapeutics and pharmaceuticals was used to target the Nucleoprotein using drug design techniques, including, but not limited to computer-based drug design methods.

Structure-based drug design may be used to target a protein or peptide fragment as well as the analogous proteins or peptides in other strains of Ebola, including for example, Sudan, Reston, Tai Forest, Bundibugyo, and Marburg viral strains. The present disclosure provides proteins, fragments, and plasmid preparations comprising amino acid sequences encoding the Ebola virus proteins and peptides, as well as analogous proteins and peptides from each of the viral strains previously described. For example, an embodiment of the Tai Forest NP$^{Ct}$ of the present disclosure may comprise, consist of, or consist essentially of the following LB1405 sequence:

(SEQ ID NO: 1)
GAMAKPHSEQSEEMYRHILQTQGPFDAILYYMMTEEPIVFSTDGKEYV

YPDSLEGEHPPWLSEKEALNEDNRFITMDDQQFYWPVMNHRNKFMAILQH

HK.

An embodiment of the Sudan NP$^{Ct}$ of the present disclosure may comprise, consist of, or consist essentially of the following LB1404 sequence:

(SEQ ID NO: 2)
GAMANSKKSSALEETYYHLLKTQGPFEAINYYHLMSDEPIAFSTESGKEY

IFPDSLEEAYPPWLSEKEALEKENRYLVIDGQQFLWPVMSLRDKFLAVLQ

HD.

An embodiment of the Bundibugyo NP$^{Ct}$ of the present disclosure may comprise, consist of, or consist essentially of the following LB1403 sequence:

(SEQ ID NO: 3)
GAMANAQSEQSIAEMYQHILKTQGPFDAILYYHMMKEEPIIFSTSDGKEY

TYPDSLEDEYPPWLSEKEAMNEDNRFITMDGQQFYWPVMNHRNKFMAILQ

HHR.

An embodiment of the Reston NP$^{Ct}$ of the present disclosure may comprise, consist of, or consist essentially of the following LB1402 sequence:

(SEQ ID NO: 5)
GAMAQSKSMQKLEETYHHLLRTQGPFEAINYYHMMKDEPVIFSTDDGKEY

TYPDSLEEAYPPWLTEKERLDKENRYIYINNQQFFWPVMSPRDKFLAILQ

HHQ.

An embodiment of the Zaire NP$^{Ct}$ of the present disclosure may comprise, consist of, or consist essentially of the following LB1305 sequence:

(SEQ ID NO: 5)
MANTQSEHSFEEMYRHILRSQGPFDAVLYYHMMKDEPVVFSTSDGKEYTYP

DSLEEEYPPWLTEKEAMNEENRFVTLDGQQFYWPVMNHKNKFMAILQHHQ.

The protein and peptide fragments disclosed herein, as well as the analogous fragments made and described herein, are also useful as vaccines or to elicit an immune response in a subject. The peptide vaccine of the present disclosure is likely to increase the therapeutic effect of this and other combination therapies. The present application further discloses vaccine compositions comprising immunogenic peptides.

In one embodiment, the present invention provides a set of peptides, to be used together as a cocktail or individually as a component of a vaccine (e.g., immunogen) to prevent or to treat human Ebola infection. The therapeutic cocktail may include the nucleocapsid fragment from one or more Ebola viral strains. When administered, the cocktail or combination of peptides elicit an immunogenic response in the subject. In one embodiment the composition comprises a recombinantly expressed peptide consisting of SEQ ID NO: 1, SEQ ID NO: 2, SEQ ID NO: 3, SEQ ID NO: 4, SEQ ID NO: 5 or a recombinantly expressed peptide that differs from SEQ ID NO: 1, SEQ ID NO: 2, SEQ ID NO: 3, SEQ ID NO: 4, SEQ ID NO: 5 by 1, 2 or 3 amino acid substitutions, optionally in combination with an adjuvant.

The therapeutic or vaccine composition of the present disclosure may also include an adjuvant or a pharmaceutically acceptable carrier. In one aspect, at least two peptides are included in the composition. Any combination of the peptides may be used. In one aspect, the immunogenic therapeutic or vaccine comprises six isolated viral peptides. In another aspect, it includes seven isolated viral peptides. Various aspects and embodiments of the invention are described in further detail below.

Another embodiment of the present disclosure is directed to the preparation and use of a pharmaceutical composition. The therapeutic or compound of the present disclosure comprises a compound useful for the treatment of diseases, disorders, or infections, such as the Ebola virus infection disclosed herein. In the present pharmaceutical or therapeutic composition, an antibody may be the compound or active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art. An illustrative embodiment of the present disclosure may comprise at least one active peptide, one or more acceptable carriers, and optionally other peptides or therapeutic agents.

For in vivo applications, the peptides of the present invention may comprise a pharmaceutically acceptable salt. Suitable acids which are capable of forming such salts with the compounds of the present invention include inorganic acids, such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

Pharmaceutically acceptable carriers include physiologically tolerable or acceptable diluents, excipients, solvents or adjuvants. The compositions are preferably sterile and non-pyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isosteararyl alcohols, polyoxyethylene sorbitol and sorbitan esters, microcrystalline cellulose, aluminum methahydroxide, bentonite, kaolin, agar-agar and tragacanth, or mixtures of these substances, and the like.

The pharmaceutical compositions may also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g. 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) may be used. The compositions may be prepared in conventional forms, either as liquid solutions or suspensions, solid forms suitable for solution or suspension in liquid prior to injection, or as emulsions. Pharmaceutical compositions according to the present invention may be prepared in a manner fully within the skill of the art.

The peptides of the invention, pharmaceutically acceptable salts thereof, or pharmaceutical compositions comprising these compounds may be administered so that the compounds may have a physiological effect. For example, in one embodiment of the present disclosure, a protein or peptide of the invention, or a combination thereof, may be administered to a subject by a route selected from, including, but not limited to, intravenously, intrathecally, locally, intramuscularly, topically, orally, intra-arterially, etc. Administration may also occur enterally or parenterally; for example orally, rectally, intracisternally, intravaginally, intraperitoneally, locally (e.g., with powders, ointments or drops), or as a buccal or nasal spray or aerosol. Parenteral administration is preferred. Particularly preferred parenteral administration methods include intravascular administration (e.g. intravenous bolus injection, intravenous infusion, intra-arterial bolus injection, intra-arterial infusion and catheter instillation into the vasculature), peri- and intra-target tissue injection (e.g. peri-tumoral and intra-tumoral injection), subcutaneous injection or deposition including subcutaneous infusion (such as by osmotic pumps), intramuscular injection, and direct application to the target area, for example by a catheter or other placement device. Controlled- or sustained-release formulations of a pharmaceutical composition of the invention may be made using conventional technology The pharmaceutical compositions useful for practicing the invention may be administered to deliver a dose of between 1 ng/kg/day and 100 mg/kg/day.

Where the administration of the peptide is by injection or direct application, the injection or direct application may be in a single dose or in multiple doses. A pharmaceutical composition of the invention may also be prepared, packaged, and/or sold in bulk, such as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. However, where the administration of the compound is by infusion, the infusion may be a single sustained dose over a prolonged period of time or multiple infusions.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Methods of Administering Pharmaceutical Compositions

In addition to ex vivo administration of the present compositions, the present disclosure also describes in vivo methods of treating a subject. The methods described herein comprise, consist of, and consist essentially of administering a pharmaceutical or therapeutic composition of the present disclosure comprising at least one compound of the present invention to a subject. In particular, the methods of the present disclosure are directed to administering the protein, peptide fragments, and/or antibody described herein to a subject for treatment of a disease, disorder, or an infection. More specifically, the compositions and methods of the present disclosure are directed to a method of treating Ebola virus by administering the compositions of the present disclosure to a subject. Compounds identified by the methods of the invention may be administered with known compounds or in combination with other medications as well. In accordance with one embodiment a method of treating an Ebola infection in a patient is provided wherein the method comprising administering a composition comprising an Ebola Nucleoprotein antibody as disclosed herein to the patient.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Typically, dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. In one aspect, the dosage of the compound will vary from about 1 mg to about 10 g per kilogram of body weight of the animal. In another aspect, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Suitable preparations of the pharmaceutical compositions described herein include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

In addition to the active ingredient, a pharmaceutical composition of the invention may further comprise one or more additional pharmaceutically active or inactive components or agents. Particularly contemplated additional agents include anti-emetics and scavengers, such as cyanide and cyanate scavengers. Other additional ingredients may include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other additional ingredients that may be included in the pharmaceutical compositions of the invention are known in the art and described, for example in Genaro, ed., 1985, *Remington's Pharmaceutical Sciences*, Mack Publishing Co., Easton, Pa.

In other embodiments, therapeutic agents and pharmaceutical compositions of the present disclosure, include, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the multimeric peptide ligand complexes described herein. Drugs useful in the invention may, for example, possess a pharmaceutical property selected from the group consisting of antimitotic, antikinase, alkylating, antimetabolite, antibiotic, alkaloid, anti-angiogenic, pro-apoptotic agents, and combinations thereof. Techniques for detecting and measuring these agents are provided in the art or described herein.

Other embodiments of the invention will be apparent to those skilled in the art based on the disclosure and embodiments of the invention described herein. It is intended that the specification and examples be considered as exemplary only, with a true scope and spirit of the invention being indicated by the following claims. While some representative experiments have been performed in test animals, similar results are expected in humans. The exact parameters to be used for injections in humans may be easily determined by a person skilled in the art. Other techniques known in the art may be used in the practice of the present invention.

The invention is now described with reference to the following Examples. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

While this invention has been disclosed with reference to specific embodiments, it is apparent that other embodiments and variations of this invention may be devised by others skilled in the art without departing from the true spirit and scope of the invention.

Example 1: Materials and Methods

A. In Silico Sequence Analyses

Secondary-structure and tertiary-structure predictions, as well as disorder predictions, were carried out using the Jpred (Cole et al., 2008; Cuff et al., 1998), Phyre2 (Kelley & Sternberg, 2009), EMBOSS (Rice et al., 2000), GlobPlot (Linding et al., 2003) and DisMeta (Huang et al., 2014) servers. Amino-acid sequence conservation was analyzed using Geneious and ConSurf (Ashkenazy et al., 2010).

B. Preparation of Protein Samples

The open-reading frames from five Ebola virus strains (i.e., Zaire, Bundibugyo, Tai Forest, Sudan, and Reston) and Marburg virus were optimized for *E. coli* expression and, amplified by Polymerase Chain Reaction (PCR). PCR primers were designed for seamless recombinase-assisted cloning, which contained approximately 15-nucleotide complementary sequence to the flanking regions of the open vector, used according to the manufacturer's recommendations. PCR products were separated by 0.8% agarose electrophoresis in 0.5× Tris/Borate/EDTA (TBE) Buffer and gel-extracted using a gel extraction kit protocol from Qiagen.

Purified inserts were cloned into the modified pSNAP-tag (T7)-2 vector and digested either by NdeI or SmaI restriction enzymes or into pHFT2 vector, after a double digest with BamH1 and XhoI using InFusion HD Cloning Kit. The reaction mix contained 1 μL of vector insert at a concentration ranging from about 30 ng/μL-100 ng/μL, 0.8 μL InFusion 5× enzyme mixture, and 2.2 μL of an open vector at a concentration ranging from about 7 ng/μL to about 10 ng/μL. Samples were incubated for 15 minutes at 50° C., followed by 5 minutes incubation on ice. After that, 20 μL of chemically component BL21 Gold (DE3) cells was added, and the mixtures were incubated on ice for about an additional 45 minutes.

Heat shock was performed by 45 seconds at 42° C. Cells were cooled on ice for 2 minutes and recovered with 200 μL of SOC medium for 1 hour. Next, each sample was plated on ampicillin at a concentration of about 0.1 mg/mL on a LB agar plate and incubated overnight at 37° C. The next day, a single cell colony was picked from the plate and used to inoculate 5 mL of 2×YT medium supplemented with about 0.1 mg/mL ampicillin. The inoculated plate was grown overnight at 37° C. with shaking at about 250 rpm.

Each pre-culture was used to inoculate 1 L of 2×YT medium containing about 0.1 mg/mL ampicillin, and grown at 37° C., optionally with shaking at about 220 rpm until $OD_{600}$ of about 0.8. The cells were then induced with 0.5 mM isopropyl β-D-1-thiogalactopyranoside (IPTG) cultured for 16 hour at 18° C., and harvested at 9,000×g for 13 minutes. The cell pellets were frozen and kept at −20° C. until use.

During use, one or more cell pellets were thawed and resuspended in 30 ml of Sonication Buffer placed in a IKA T-25 Ultra Turrax homogenizer, and lysed using a Branson Sonifier 450 at settings of 3×1 min pulses with 5 min breaks. The homogenate was further purified by centrifugation at 55,000×g for about 50 minutes. The clear supernatant was incubated in a batch with 1 ml of cobalt TALON Metal Affinity Resin for 45 minutes at 4° C. The resin was packed into a 10 ml column and the flowthrough fraction was collected. The resin was washed with 6 mL of washing Buffer. The protein was eluted by gravity flow with 1 mL of Elution buffer per fraction. Protein concentration was calculated based on the sample optical density at $A_{280}$ and its extinction coefficient. The purity and identity of the protein were evaluated by SDS-PAGE and MALDI-TOF Mass Spectrophotometry. The protein preparations were aliquoted and stored at −80° C.

C. SDS-PAGE Electrophoresis

Proteins were denatured by mixing (1:1 v/v) with 2×SDS-loading buffer (Bio-Rad) containing 0.7M β-mercaptoethanol and heating for 2 minutes at 96° C. Heated samples were loaded into the wells of a Mini-PROTEAN® TGX™ Precast Gel (Bio-Rad, 4-20%) placed in a Mini-PROTEAN® Tetra Cell (Bio-Rad) filled with SDS-PAGE running buffer, and run at 180 V until the dye front reached the bottom of the gel. The gel was removed, rinsed with water and stained with Coomassie Brilliant Blue solution for 30 seconds in a microwave and 20 min at room temperature (e.g., about 21° C.-23° C.), and then destained in the Destaining Solution overnight. Gel pictures were taken using ChemiDoc™ MP System and analyzed in the Image Lab 4.0 software (Bio-Rad).

D. Preparation of Recombinant Proteins

Complimentary DNA (cDNA) constructs coding for the peptide fragments comprising, consisting of, or consisting essentially of amino acid residues 1-412 and 641-739 of the Zaire Ebola virus (EBOV) Nucleoprotein (NP) were synthesized commercially (GENEWIZ) and synthetically using optimized codon frequencies for *E. coli*. The constructs were cloned into a His6-MBP-Parallel 1 vector (Sheffield et al., 1999). Consequently, the proteins were expressed as fusion proteins with MBP and purified using affinity chromatography. BL21-CodonPlus (DE3)-RIPL *E. coli* cells (Stratagene) were used for expression. Cells were grown in different types of media (see below) supplemented with 100 μg ml-1 ampicillin and 34 μg ml-1 chloramphenicol and were induced with 0.5 mM IPTG. All purification steps were carried out at 4° C. Protein concentrations were determined spectrophotometrically based on calculated molar absorption coefficients at 280 nm.

E. Expression and Purification of Recombinant EBOV Nucleoprotein N-Terminal Domain ($NP^{Nt}$) Protein N-terminal Nucleoprotein ($NP^{Nt}$) was expressed in Terrific Broth. Induction was carried out at an OD600 of 2.0 and growth continued for 18 hours at 16° C. Cells were harvested by centrifugation at 3,500 rev min-1 for 30 min and frozen at −20° C. The pellet was were suspended in lysis buffer (50 mM Tris-HCl, 500 mM NaCl, 5 mM β-mercaptoethanol pH 8.0). Cells were disrupted by Dounce and high-pressure homogenizers, then sonicated, and centrifuged at 35,000 rev min-1 for 45 min. Clear supernatant was applied onto an amylose resin column (Qiagen). After 1 hour of incubation, the flowthrough was collected and the resin was washed with 500 ml lysis buffer. The fusion protein was eluted with 50 mM Tris-HCl, 500 mM NaCl, 5 mM β-mercaptoethanol, 10 mM maltose at pH 8.0.

The fusion protein was digested with Tobacco Etch Virus (rTEV) protease with concomitant dialysis against 4 L of a dialysis buffer (50 mM Tris-HCl, 500 mM NaCl, 5 mM 3-mercaptoethanol pH 8.0) overnight. The solution was passed through an Ni-NTA agarose gravity column (Qiagen) and the flowthrough fraction containing $NP^{Nt}$ was collected. Concentrated samples of $NP^{Nt}$ were subjected to size-exclusion chromatography using a Superdex 200 column connected to a GE Healthcare ÄKTA FPLC system, and were equilibrated with 50 mM Tris-HCl, 500 mM NaCl, 5 mM β-mercaptoethanol pH 8.0. Fractions containing $N^{PNt}$ were pooled and concentrated.

F. Expression and Purification of Recombinant of EBOV Nucleoprotein C-Terminal Domain ($NP^{Ct}$) Protein Protein expression, cell disruption, and centrifugation were carried out as described above for $NP^{Nt}$, except that 300 mM NaCl was used in the lysis buffer. The supernatant was applied onto a column containing 3 ml Ni-NTA agarose resin (Qiagen) and incubated with the resin mixture for 1 hour on a rocking platform. The fusion protein was eluted with a buffer consisting of 50 mM Tris-HCl, 300 mM NaCl, 5 mM β-mercaptoethanol, and 250 mM imidazole at pH 8.0. The eluted protein was digested with rTEV protease and dialyzed overnight against 4 L of solution containing 50 mM Tris-HCl, 300 mM NaCl, and 5 mM β-mercaptoethanol at pH 8.0.

Protein samples were passed slowly through an Ni-NTA agarose column and the flowthrough containing $NP^{Ct}$ was collected. Concentrated samples were subjected to size-exclusion chromatography on a Superdex 75 column connected to a GE Healthcare ÄKTA system, and equilibrated with 50 mM Tris-HCl, 150 mM NaCl, and 5 mM β-mercaptoethanol at pH 8.0. Fractions containing the protein were pooled and concentrated.

A fragment of cDNA corresponding to the N-terminally truncated $NP^{Ct}$ (i.e., amino acid residues of about 660 to about 739) was amplified by Pfu polymerase (Thermo Scientific), and cloned into NcoI and SalI restriction sites in the 6×His6-MBP-Parallel 1 vector. The protein was expressed and purified exactly as the full-length $NP^{Ct}$ described herein G. Preparation of SeMet-Labeled $NP^{Ct}$ SeMet-labeled protein was expressed in M9 minimal medium enriched with 40 μg ml-1 of every amino acid except methionine. The culture was grown at 37° C. until the OD600 reached 0.8. The temperature was changed to 25° C. and 50 mg each of leucine, isoleucine, valine, and tryptophan plus 100 mg each of threonine, lysine, phenylalanine, cysteine and selenomethionine were added per liter of medium. After induction, growth was continued for 17 hours. Labeled protein was purified exactly as described herein for unlabeled NP$^{Ct}$ H. Preparation of 15N-Labeled and 13C,15N-Labeled NP$^{Ct}$ 15N-labeled and 13C, 15N-labeled protein samples were obtained by growing transformed cells in M9 minimal medium enhanced by the addition of labeled BioExpress 1000 Cell Growth medium (Cambridge Isotope Laboratories, final concentration of 0.6%). Ammonium sulfate (15N, 99%, Cambridge Isotope Laboratories, 1 g 1-1) and D-glucose (13C, 99%, Cambridge Isotope Laboratories, 2 g 1-1) were used for the labeling. Protein expression was induced at an OD600 of 0.9-1.2 and the temperature was changed from 37° C. to 20° C. After 16 hours the cells were harvested, and the cell pellets were stored at −20° C.

Labeled proteins were purified in exactly the same manner for unlabeled NP$^{Ct}$, except that the buffer for size-exclusion chromatography comprised, consisted of, or consisted essentially of 40 mM HEPES, 150 mM NaCl, and 5 mM β-mercaptoethanol at pH 7.5. For assignment experiments, a sample of 400 μM 15N-NPCt and 800 μM 13C, 15N-NPCt in 40 mM HEPES, 150 mM NaCl, 5 mM β-mercaptoethanol pH 7.5 buffer supplemented with 5% D2O was prepared.

I. Crystallization of EBOV NP$^{Ct}$

NP$^{Ct}$ concentrated to 7.4 mg ml-1 was used to set up screens using The JCSG+ Suite (Qiagen) and PEG/Ion HT (Hampton Research) with a Mosquito robot (TTP Labtech). For each crystallization condition, 1:1, 1:2, and 2:1 ratios of precipitant to protein solution were used. Crystals appeared in solutions consisting of 0.2 M magnesium formate, 20% PEG 3350 (the JCSG+ Suite) and 0.2 M calcium acetate hydrate, 20% PEG 3350 (PEG/Ion HT). Optimization of crystallization conditions with different concentrations of precipitants was carried out manually (e.g., by the hanging-drop vapor-diffusion method) or automatically (e.g., by the sitting-drop vapor-diffusion method). Single crystals suitable for X-ray experiments were then grown by the sitting-drop vapor-diffusion method using a 1:1 ratio of a reservoir solution (comprising 50 mM magnesium formate and 19.3% PEG 3350), as well as a protein solution with a protein concentration of 12.5 mg ml-1. The final conditions found were 300 mM magnesium formate and 19.3% PEG 3350.

J. Data Collection and Structure Characterization and Determination

Crystals were cryoprotected under a range of conditions and then screened for diffraction quality. The crystals of unlabeled NP$^{Ct}$ used for final data collection were transferred in a stepwise manner into 20%, 30%, and finally 40% PEG 3350. The SeMet-labeled proteins that gave the best diffraction were soaked in fresh well solution and then in a solution comprising 200 mM magnesium formate, 25% PEG 3350, and 30% glycerol. All crystals were flash-cooled by immersion into liquid nitrogen. X-ray data were collected at 100 K on the SER-CAT beamlines (Southeast Regional Collaborative Access Team) at the Advanced Photon Source, Argonne National Laboratory, Chicago, USA. Data were indexed, integrated, and scaled with HKL-2000 (Otwinowski & Minor, 1997). See Table 2 for details of data processing.

In the case of SeMet-labeled trigonal crystals, phase estimates were obtained by the SAD method using data collection at the absorption peak of λ=0.97907 Å (see Table 2). The Se substructure was determined using SHELXD (Schneider & Sheldrick, 2002) and phases were calculated using SHELXE (Sheldrick, 2002). A large part of the model was automatically built with ARP/w ARP (Langer et al., 2008) and further improved manually with Coot (Emsley & Cowtan, 2004). Rfree was monitored by setting aside about 5% of the reflections as a test set. Restrained positional and isotropic atomic displacement parameter (ADP) refinement was performed with PHENIX (Adams et al., 2010).

The structure of the orthorhombic form (unlabeled NP$^{Ct}$) was solved using the model from the trigonal form and the molecular-replacement method as implemented in PHENIX (Adams et al., 2010). The atomic model of the orthorhombic structure was refined in a manner identical to the trigonal form (see Table 2). Structural figures were prepared using PyMOL K. Nuclear Magnetic Resonance (NMR) Studies A Varian VNMRS 600 MHz spectrometer equipped with a cryoprobe was used to obtain two-dimensional H—N and H—C Heteronuclear Single Quantum Coherence (HSQC) spectroscopy and three-dimensional HNCO, HN(CA)CO, CBCA(CO)NH and HNCACB spectra at 25° C. NMRPipe (Delaglio et al., 1995) was used to process the spectral data. NMRView (Johnson, 2004) and Sparky 3 (T. D. Goddard & D. G. Kneller, University of California, San Francisco, USA) were used for spectrum visualization and sequential assignment of backbone and C, 1H (except H), 13C, and 15N resonances.

L. Thermal Stability Assays

The melting temperature ($T_1$) of protein samples was determined by monitoring the fluorescence of SYPRO Orange dye (Life Technologies) in the presence of the protein as a function of temperature. All proteins used in the assays were dialyzed against 50 mM Tris-HCl, 250 mM NaCl, and 5 mM β-mercaptoethanol at pH 8.0. Assays were performed in 20 μl containing 20 ng protein and 10× the standard concentration of the dye. Fluorescence was recorded as a function of temperature from 20° C. to 90° C. using an Applied Biosystems StepOnePlus Real-Time PCR System (Life Technologies). This instrument uses wavelengths of 488 nm for excitation and 586 nm for emission.

Example 2: Identification of Folded Domains in Zaire EBOV NP

Nucleoproteins (NPs) of Filoviridae are significantly longer than those of other members of Mononegavirales with Zaire EBOV NP containing about 739 amino acids. There is evidence that this architecture is owing to the presence of two distinct modules, a C-terminal protein domain and a N-terminal protein domain.

Genomic characterization of the Ebola virus genome and the Nucleoprotein were assessed. The hydrophobic N-terminal domain comprises about 412 amino acids (residues 1-412), and is important for self-assembly, transcription, and replication. The hydrophilic C-terminal domain comprises about 150 amino acids (residues 641-739), and is required for full formation of the Nucleocapsid and for viral genome replication. The C-terminal domain is specifically involved in the incorporation of the nucleocapsid into the virion and interaction with VP40. Nevertheless, the precise boundaries of these functional units have not been identified, nor have they been shown to form stably folded domains.

Analysis of amino acid conservation among Filoviridae NPs yielded results consistent with the suggested two-domain architecture. Among all seven species, the N-terminal region is most conserved. In the C-terminal domain, about 100 amino acid residues also show some conservation. Protein conservation in the C-terminal region of the Nucleoprotein is increased when the MARV and LLOV sequences are excluded from analysis.

In silico secondary and tertiary protein structure predictions, as well as disorder predictions, determined that the fragments comprising amino acids 1-412 ($NP^{Nt}$) and 641-739 ($NP^{Ct}$) were likely to be globular modules. Polypeptides corresponding to those putative domains were expressed in $E.$ $coli$ in fusion with a His-MBP tag. Both $NP^{Nt}$ and $NP^{Ct}$ proteins of EBOV Zaire were overexpressed in $E.$ $coli$ in high yield and were purified as described in Materials and Methods of Example 1.

Circular-dichroism (CD) spectra indicated a significant content of secondary structure in each N- and C-terminal domain. Further, a thermal stability assay (TSA) showed that the midpoints of secondary structure unfolding transition occurred at temperatures of 54.9° C. and 56.9° C. for the $NP^{Nt}$ and $NP^{Ct}$ domains, respectively. The remainder of this disclosure focuses on the C-terminal domain ($NP^{Ct}$). The minimum for the negative derivative of the reporter fluorescence indicates the midpoint of the melting (denaturation) temperature of the protein sample.

Example 3: Determination of the Structure of Zaire EBOV $NP^{Ct}$

To assess whether recombinant $NP^{Ct}$ is fully folded or whether it contains any significant stretch of unstructured polypeptide chain, 15N-labeled protein samples were prepared and recorded on an HSQC spectrum. The spectrum was well dispersed and consistent with the protein being fully folded in solution. The two peaks with the highest $^{15}N$ ppm are Trp indole NH. Unassigned peaks in the low field $^{1}H$-$^{15}N$ region are due to side chains. Using this approach, the backbone (except H) amide and $^{13}C$ assignments for 93 out of 95 non-proline residues were determined.

The assigned chemical shifts were used in TALOS-N to define the secondary-structure elements. At this point, owing to the successful crystallization of $NP^{Ct}$, efforts to determine the full three-dimensional structure in solution by Nuclear Magnetic Resonance (NMR) were discontinued. Nevertheless, the availability of the assignments will allow future identification and characterization of interactions with binding partners.

Orthorhombic crystals of native $NP^{Ct}$ that diffracted beyond 1.8 Å resolution were obtained using PEG 3350 as a precipitant (see § 2). A SeMet-labeled sample yielded a trigonal crystal form that diffracted well to 2.0 Å resolution and allowed structure determination using SAD and subsequent refinement. The model includes amino acid residues 641-739, with the four N-terminal amino acids not being identifiable via electron density.

Further, the side chains of Glu645, His646, Glu649, Lys684, Glu695, Glu709, Lys728 and Gln739 are partly disordered so that some or all of their atoms are not visible in the electron density. Once the refinement of the trigonal form was completed, this structure was used to determine the orthorhombic crystal form by molecular replacement methodology. The resulting structure was refined in a fashion similar to that described above. Most of the side-chain disorder was also observed in the orthorhombic form. The crystallographic details are provided in Table 2.

Example 4: EBOV $NP^{Ct}$ Represents a Novel Fold

The secondary structure elements of the C-terminal domain of the EBOV NP, as determined by heteronuclear NMR in solution and crystallographic X-ray analysis. The atomic models derived from the two crystal forms produced by NMR and crystallography were very similar. In fact, the secondary and tertiary structures generated by each were virtually identical.

Importantly, the secondary structural elements agree particularly well with the NMR data.

TABLE 2

Crystallographic Data Collection

|  | SeMet $P3_12$ | $P2_12_12_1$ |
|---|---|---|
| Wavelength/beamline | 0.97907 (ID) | 1.0000 (BM) |
| Unit cell | a = 56.5Å, b = 56.5Å, c = 63.5Å | a = 36.6Å, b = 49.2Å, c = 53.8Å |
| Resolution (Å)* | 1.98(2.01-1.98) | 1.75(1.78-1.75) |
| No. of total reflections | 73492 | 63568 |
| No. of unique reflections | 8447 | 10026 |
| Redundancy | 8.7 | 6.3 |
| Completeness (%) | 97.2(76.3) | 97.7(82.2) |
| $R_{sym}$ (%) ** | 12.5(26.2) | 4.9(29.2) |
| I/σ(I) | 12.5(3.7) | 31.6(3.9) |
| Refinement statistics | 901 non-H atoms 100 solvent (oxygen) | 900 non-H atoms 95 solvent (oxygen) |
| Resolution limits(Å) | 26.7-1.98 | 29.4-1.75 |
| Reflections in working/test sets | 8,427/729 | 9,989/489 |
| $R_{cryst}$§/$R_{free}$ (%) | 18.4/22.9 | 18.5/22.5 |
| Bond(Å)/angle(°) r.m.s. deviation | 0.012/1.3 | 0.013/1.3 |
| Ramachandran Plot |  |  |
| Favored regions | 100% | 98.95% |
| Generously allowed regions | 0% | 1.05% |
| Disallowed regions | 0% | 0% |

*The numbers in parentheses describe the relevant value for the last resolution shell.
**$R_{sym} = \Sigma |I_i - \langle I \rangle|/\Sigma I$ where $I_i$ is the intensity of the ith observation and $\langle I \rangle$ is the mean intensity of the reflections.
§$R_{cryst} = \Sigma ||F_{obs}| - |F_{calc}||/\Sigma |F_{obs}|$, crystallographic R factor, and $R_{free} = \Sigma ||F_{obs}| - |F_{calc}||/\Sigma |F_{obs}|$ where all reflections belong to a test set of randomly selected data.
NOTE:
+/- reflections from the SeMet peak data set were scale together for the data set used in refinement.

At the N-terminus, NP$^{Ct}$ contains an antiparallel pair of α-helices (at amino acid residues 648-658 and 661-671) followed by two β-strands arranged in an antiparallel hairpin (at amino acid residues 676-680 and 683-688). A stretch of an irregular but structured polypeptide chain leads to a short α-helix (at amino acid residues 701-707) at the other extremity of the oblong molecule. Yet another β-hairpin (at amino acid residues 712-715 and 718-721) is followed by a C-terminal α-helix (at amino acid residues 727-738). The C-terminal α-helix also appears to be a critical element of the structure, as it runs through the center of the molecule, providing a scaffold around which most of the remainder of the molecule is folded.

A diagrammatic representation of the structure of the EBOV was prepared. Amino acid residues that belong to the αD helix make contact with the αB helix, with both β-hairpins, and with the coil structure connecting the two β-hairpins. Three hydrophobic residues within the αD helix (i.e., Phe731, Ala733 and Ile734) are completely buried within the structure. They form the small, densely packed hydrophobic core along with the equally occluded Tyr688, Leu692, Pro697 and Trp722 (see FIG. 5B). Importantly, all of these residues are highly conserved among the five EBOV strains (the only differences are in the Sudan subtype, with Y688F and I734V substitutions).

Detailed BLAST searches confirmed that the amino acid sequence of EBOV NP$^{Ct}$ is unique and has no homologues in any other proteins except for other strains of EBOV. A search of the Protein Data Bank using the refined NP$^{Ct}$ model with the DALI server (Holm et al., 2008) did not reveal any similarities between NP$^{Ct}$ and known tertiary folds. However, when the N-terminal pair of α-helices are removed, the program FATCAT (Ye & Godzik, 2004) detected weak similarity to a TGS domain (PDB entry 3hvz), which is one of the many representatives of the β-grasp superfamily.

Given the unusual antiparallel hairpin at the N-terminus of the domain, in which the αA helix makes no other contacts with the rest of the protein, tests were conducted to determine whether the αA helix should be considered to be an integral part of the domain. An N-terminally truncated protein comprising, consisting essentially of, or consisting of amino acid residues 660-739 was purified, and its denaturation temperature ($T_m$) was measured (data not shown). The thermal stability of this N-terminal amino acid variant had a $T_m$ of only 48.0° C., which was significantly lower than the 56.9° C. $T_m$ for the NP$^{Ct}$ protein. The conclusion was that the αA helix should be regarded as an integral part of the NP$^{Ct}$ domain.

Example 5: Comparison of the Two Crystal Forms of NP$^{Ct}$

As already mentioned, the atomic models derived from the two crystal forms of the NP$^{Ct}$ protein are very similar. The only significant difference is in the orientation of the αA helix (at amino acid residues 648-658) relative to the main module. A comparison of the structures of the N-terminal helical fragment in the two crystal forms of the NP$^{Ct}$ was performed.

In general terms, the N-terminal helix rotates as a rigid body by about 8.8° and undergoes a translation of about 1.7 Å. This conformational change, evidently owing to altered crystal packing, results in a substantial rearrangement of the interface between the αA and the αB helices. The αA helix makes no contact with the NP$^{Ct}$ domain, other than with the αB helix, and consequently the different orientation of the αA helix does not affect any other parts of the structure. The remainder of the NP$^{Ct}$ (amino acid residues 661-738) superposes in the two crystal forms with a main chain surface roughness in RMS (Rq) of about 0.55 Å.

The only other small, but significant, difference between the two structures is in the loop harboring amino acid residues 715-718. In one structure, the loop is shifted by about 2.0 Å compared with the loop structure, and this appears to be due to a close crystal-packing contact.

Example 6: Evolutionary Conservation of NP$^{Ct}$ Among Filoviridae

As previously described, the NP$^{Ct}$ domain is less stringently conserved among the five strains of EBOV than the NP$^{Nt}$ domain. FIG. 1 shows amino acid conservation in the NP$^{Ct}$ domain among Filoviridae. The Zaire strain amino acid sequence is shown at the top, and the sequences of the remaining four EBOV strains (Bundibugyo, Reston, Tai Forest, and Sudan) are shown below. Table 3 shows a pairwise amino acid identity levels within the NP$^{Ct}$ domain of the five EBOV strains.

TABLE 3

Pairwise EBOV Strain NP$^{Ct}$ Amino Acid Sequence Identity (%)

| EBOV Strain | Bundibugyo | Tai Forest | Reston | Sudan |
|---|---|---|---|---|
| Zaire | 82% | 79% | 65% | 60% |
| Sudan | 61% | 62% | 74% | |
| Reston | 65% | 64% | | |
| Tai Forest | 86% | | | |

A total of 47 amino acid residues are completely conserved among the five EBOV strains and constitute a consensus template (see FIG. 1). Within this group, a number of conserved amino acids are located in the small hydrophobic core of the protein structure. Pairwise comparisons of the NP$^{Ct}$ of the five EBOV strains reveal sequence identity levels ranging from about 60% to about 86% (see Table 3 and FIG. 1).

A graph of amino acid identity level within the Filoviridae family is also shown after the EBOV sequences in FIG. 1 with the highest bars denoting invariant/conserved amino acid residues. The EBOV amino acid consensus sequence is followed by the amino acid sequences of the Marburg and Lloviu viruses (see FIG. 1). Shaded residues indicate that the amino acid residue matches the same amino acid residue of the consensus sequence.

The LLOV and MARV viral strain NP$^{Ct}$ sequences deviate significantly from the EBOV consensus. The LLOV sequence shows about 25% identity to the Sudan and Reston EBOV strains and shares 16 residues with the EBOV NP$^{Ct}$ consensus sequence. The MARV NP$^{Ct}$ sequence, on the other hand, shows such low sequence similarity to the EBOV consensus sequence that BLAST did not even identify the relationship between the viral strains (see FIG. 1). In the alignment shown in FIG. 1, only 12 amino acids from the MARV sequence were conserved when compared to the EBOV consensus. Overall, only seven amino acids in the NP$^{Ct}$ are invariant or totally conserved among all the Filoviridae.

Example 7: Analysis of NP$^{Ct}$ Surfaces and Implications for Protein-Protein Interactions and Antigenicity Since the NP$^{Ct}$ domain is a potential hub for protein-protein interactions, the molecular surfaces were analyzed with reference to amino acid conservation, propensity to form interactions mediating crystal contacts, and electrostatic potential. These analyses are relevant to further characterize the established high antigenicity of the EBOV $NP^{Ct}$ domain.

Of the total 48 amino acids that were fully conserved among the five subtypes of EBOV strains, 36 had more than 15 $Å^2$ of exposed surface. The majority of conserved amino acids are scattered throughout the surface of the $NP^{Ct}$ structure (see FIGS. 9A and 9B). The most conserved patch is located in a concave depression between the N-terminal αA and αB helices and the ½ hairpin. This patch includes the following amino acid residues among others, Tyr652, Leu656, Tyr668, Glu674, Ser679, Glu685, and Leu725. It is highly possible that this is the site of one or more of the protein-protein interactions involving the EBOV NP.

The crystal structures of the two forms of $NP^{Ct}$ previously identified were also studied for protein-protein interactions. Intermolecular contacts in protein crystals are often mediated by surface patches that are physiologically relevant for protein-protein interactions. This is particularly true for those surface patches that mediate intermolecular contacts in different crystal forms of the same protein.

Surface patches involved in crystal contacts of the two EBOV $NP^{Ct}$ structures were assessed, and identified several distinct sets of intermolecular contacts that comprise contact patches involved in the two crystal forms. Two contact patches are involved in crystal contacts in both structure forms. Predictably, both contact patches are hydrophobic in nature. One of the contact patches comprises, consists essentially of, or consists of Phe712 and Tyr721, while the other comprises, consists essentially of, or consists of Ile655, Leu666 and Tyr667. Interestingly, the first four amino acids (i.e., Phe712, Tyr721, Ile655, and Leu666) are completely conserved in the Zaire, Bundibugyo, and Tai Forest EBOV strains, but not in the Sudan and Reston strains. Notably, the Sudan strain shows lower mortality upon infection and the Reston strain does not infect humans.

The electrostatic potential of the $NP^{Ct}$ protein structure was calculated in PYMOL and mapped onto the solvent-accessible structure surface. Ribbon diagrams are shown to confirm the orientation of the molecule. Select amino acids are labeled.

The pI of the Zaire EBOV $NP^{Ct}$ domain is estimated at about 4.9 and ranges among the other strains from about 4.6 in Sudan to about 5.5 in Reston. The low pI in Zaire EBOV strain is due to a preponderance of acidic amino acid residues. Six of the amino acid residues create a contiguous patch on the protein surface: Asp673, Glu674, Asp690, Glu693, Glu694 and Glu695. The first four of these amino acid residues are either completely conserved or are conserved as Glu/Asp acids in all five EBOV strains of EBOV. The Glu694 residue is replaced by a Gly in the Tai Forest substrain, whereas Glu695 is replaced by Ala in the Reston and Sudan strains.

Figure 2:
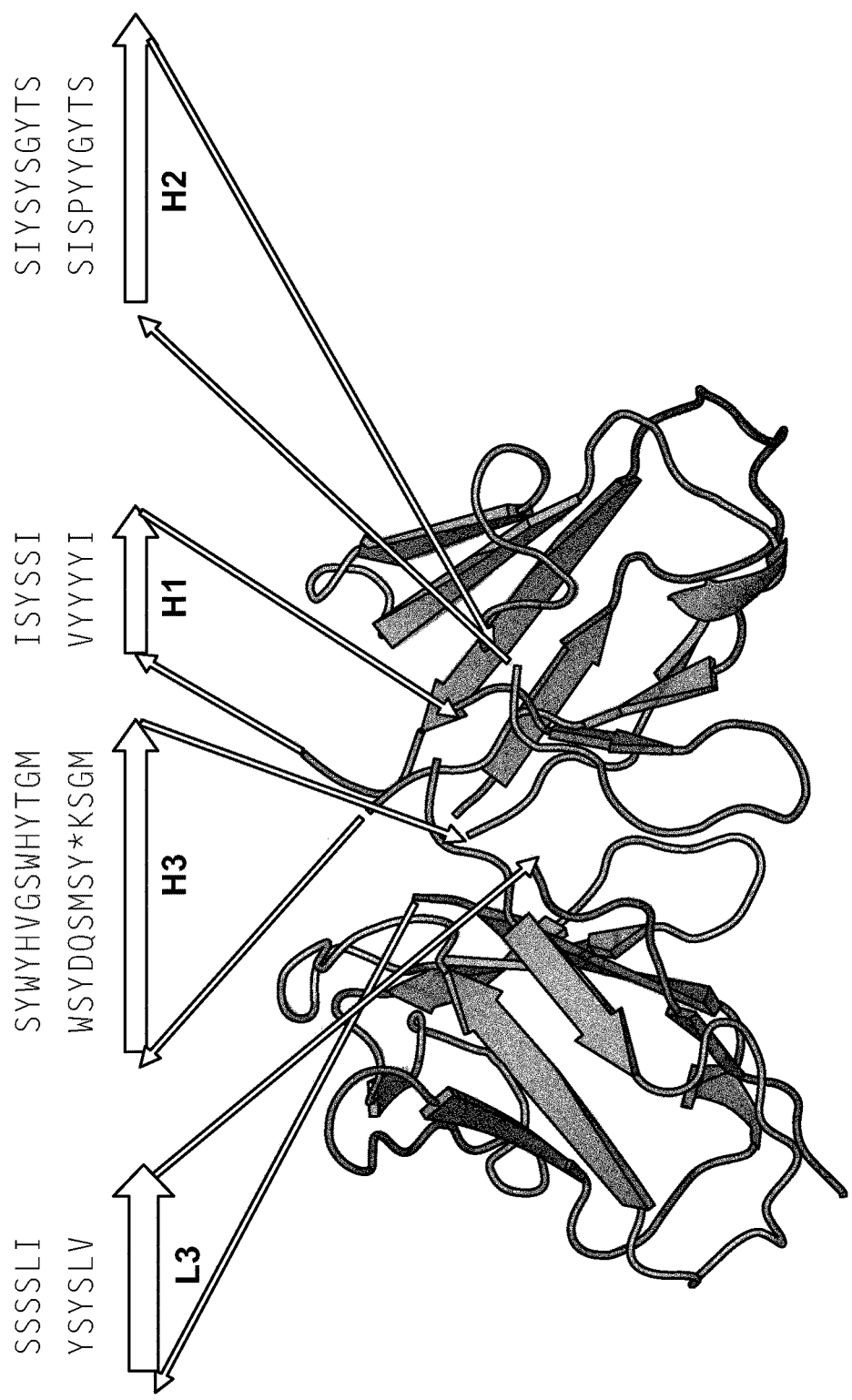
FIG. 2 is graphical representation of Fabs 6 and 20, including the amino acid sequence and corresponding location of the four complementarity determining regions on the tertiary structure: SSSLI (SEQ ID NO: 35), SYWYHVG-SWHYTGM (SEQ ID NO: 145), ISYSSI (SEQ ID NO: 43), SIYSYSGYTS (SEQ ID NO: 96) for FAB20, and YSYSLV (SEQ ID NO: 106), WSYDQSMSYKSGM (SEQ ID NO: 104), VYYYYI (SEQ ID NO: 105), and SISPYYGYTS (SEQ ID NO: 51), for FAB6.

Example 8: Using Phage Display to Generate and Purify Fragment Antigen Binding Proteins The Recombinant Antibody Network (RAN) is the largest producer of recombinant Fabs in the world. In fact, RAN has generated Fabs that were used as crystallization chaperones in numerous high-profile structural biology investigations for the determination of crystal structures of interest. Accordingly, recombinant C-terminal domains from all five strains of EBOV were provided to RAN to generate Fab using their automated phage display pipeline and the human herceptin template Based on the $NP^{Ct}$ domain from the Zaire EBOV, RAN generated two first generation Fabs denoted Fab6 and Fab20 (see FIG. 2). The Fabs were generated by screening for sequences in the four complementarity defining region (CDR) loops in the variable domain (see FIG. 2). Illustrative CDRs of Fab20 comprise, consist of, or consist essentially of SEQ ID NO: 35, SEQ ID NO: 145, SEQ ID NO: 43, and SEQ ID NO: 96. Illustrative CDRs of Fab6 comprise, consist of, or consist essentially of SEQ ID NO: 106, SEQ ID NO: 104, SEQ ID NO: 105, and SEQ ID NO: 51. FIG. 2 schematically shows the amino acid sequence of four CDRs and their location on the $NP^{Ct}$ crystal structure.

Figure 3:
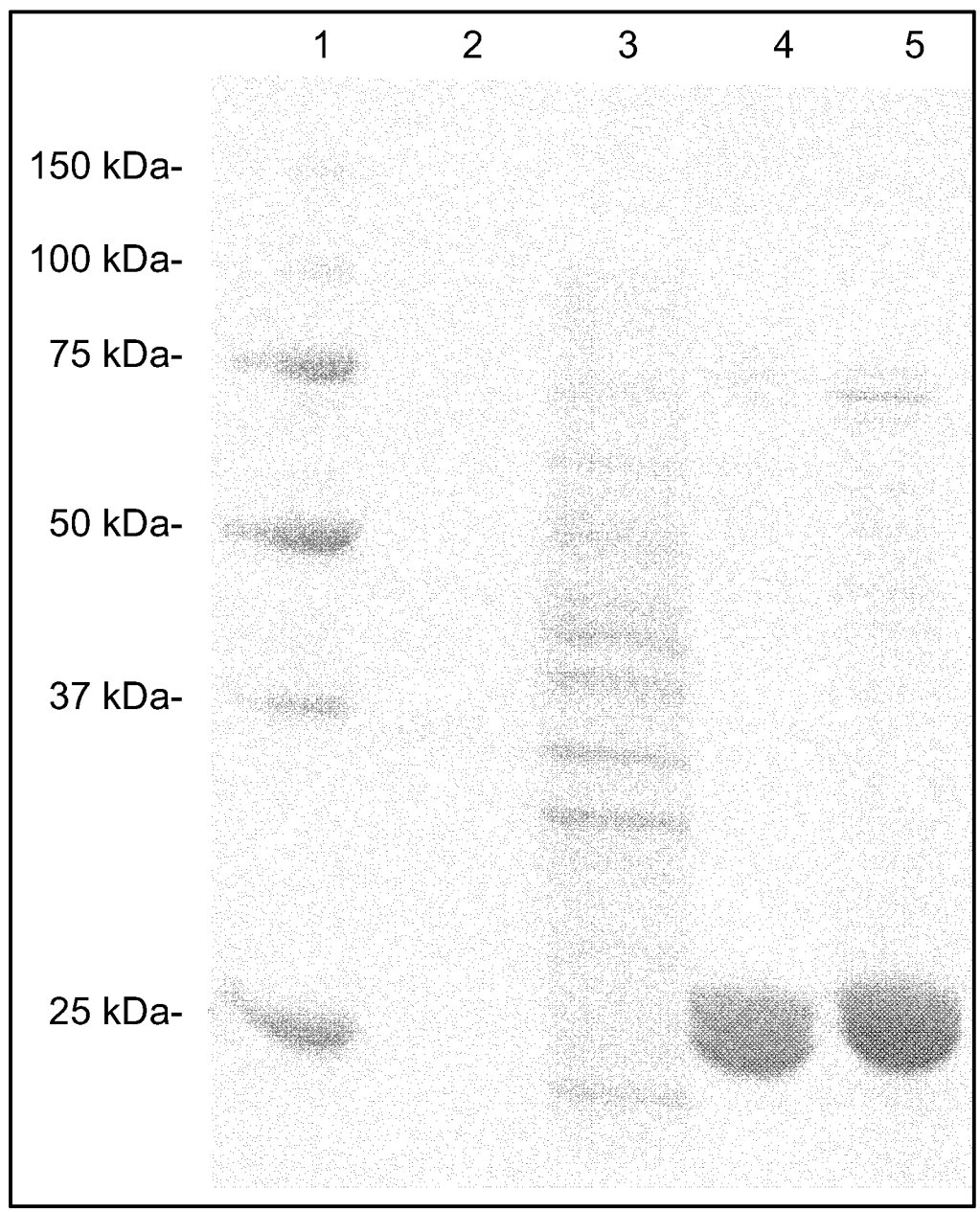
FIG. 3 is a protein gel image showing expression and purification of Fab 6 (lane 4) and Fab 20 (lane 5).

Expression and purification of the Fab proteins generated purified proteins and expression clones that were purified to high homogeneity with affinity chromatography using Protein G. The protein gel of FIG. 3 shows the protein size marker (lane 1), the uninduced total Fab protein (lane 2), the post-induced Fab protein (lane 3), affinity purified Fab 6 (lane 4), and affinity purified Fab 20 (lane 5). According to FIG. 3, both Fab 6 and Fab 20 had a protein weight of about 25 kDA.

Example 9: ITC Determination of Fab Binding to $NP^{Ct}$ of Zaire EBOV

As shown in FIG. 4, isothermal titration calorimetry (ITC) was performed to determine if there was binding of Fab6 and Fab20 to the Zaire $NP^{Ct}$. Data from ITC indicated that both Fabs bind to the Zaire $NP^{Ct}$ with ~5 nM dissociation constants ($K_D$) and the binding is strongly enthalpy driven, with small negative contribution from entropy (FIG. 5). The data strongly support the notion that both Fabs are good candidates for optimization.

Figure 4B:
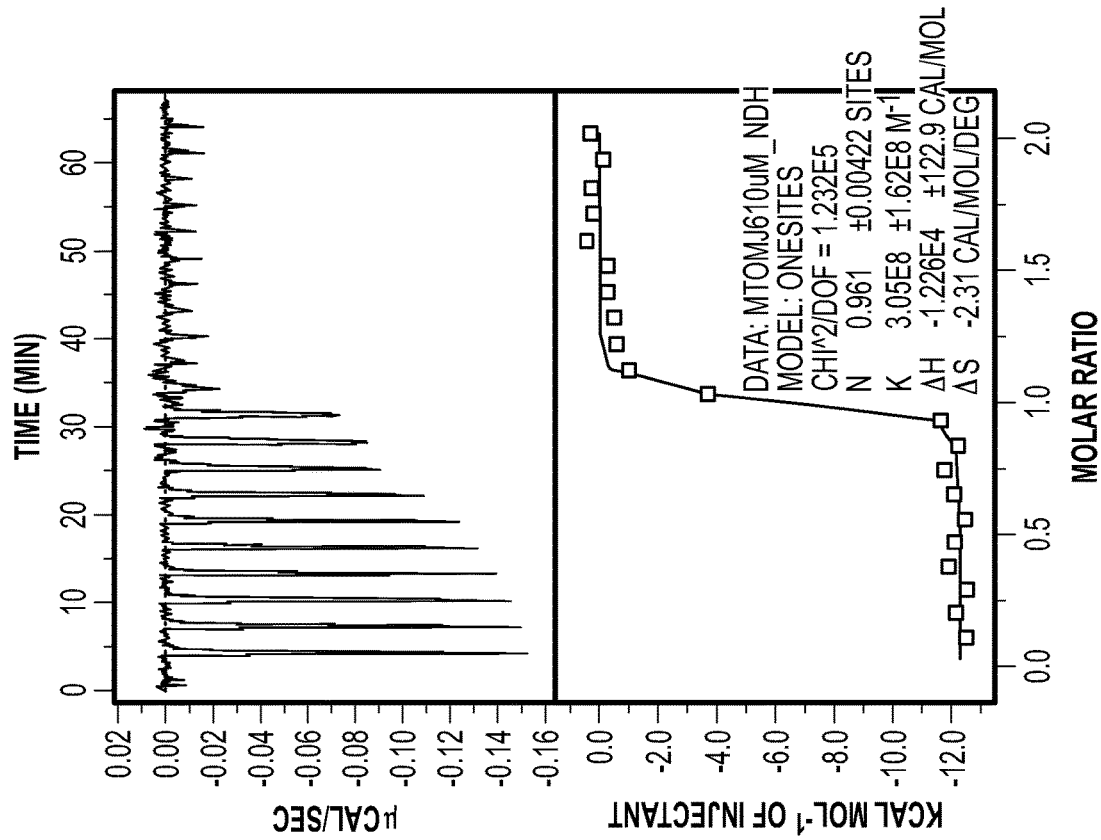
FIG. 4B is a graph showing the results of an isothermal titration calorimetry binding assay of Fab 6 to the C-terminal domain of Zaire Nucleoprotein.
Figure 4A:
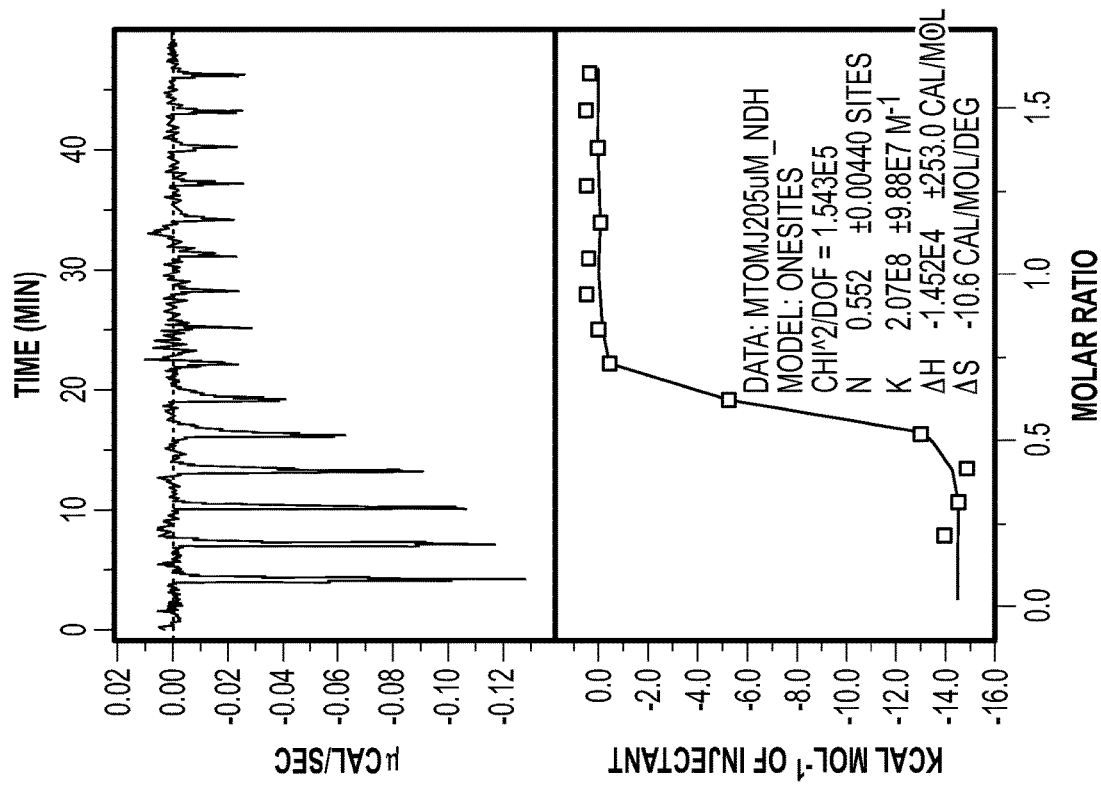
FIG. 4A is a graph showing the results of an isothermal titration calorimetry binding assay of Fab 20 to the C-terminal domain of Zaire Nucleoprotein.

Whether Fab6 and Fab20 are capable of recognizing the full-length NP protein ectopically expressed in a eukaryotic cell was investigated. This was necessary to ascertain if the Fabs could bind to the free N-terminus of the $NP^{Ct}$, if the Fabs were high selectivity towards NP, and whether they would cross-react with any eukaryotic proteins. FIG. 4 shows the results of this experiment, which confirms that Fab20 (see FIG. 4A) and Fab6 (see FIG. 4B) are highly selective, have no cross-reactivity, and have very high sensitivity when binding to Zaire $NP^{Ct}$.

Figure 5A:
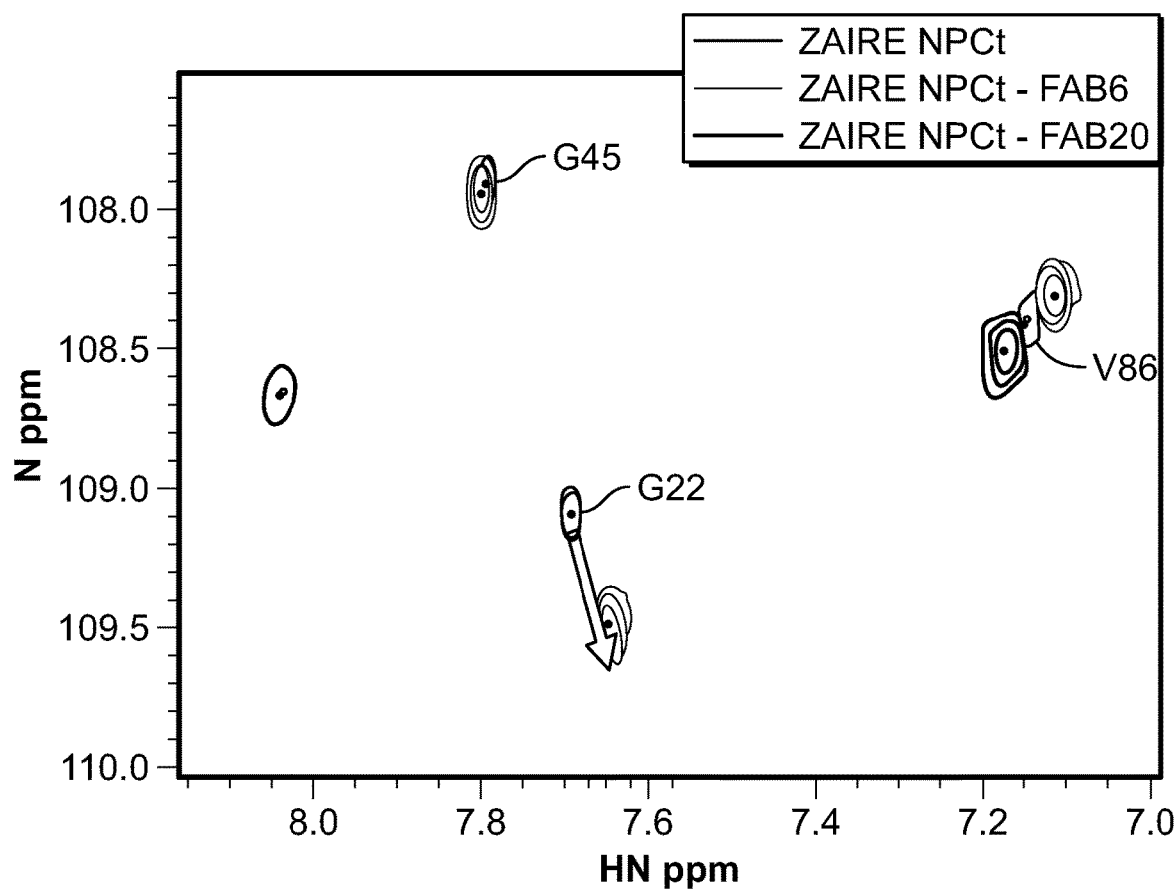
FIG. 5A is a graph showing the spectra of 1) free, labeled C-terminal domain of Zaire Nucleoprotein (NP$^{Ct}$), 2) a complex of Fab 20 and labeled NP$^{Ct}$, and 3) a complex of Fab 6 and labeled NP$^{Ct}$.
Figure 5B:
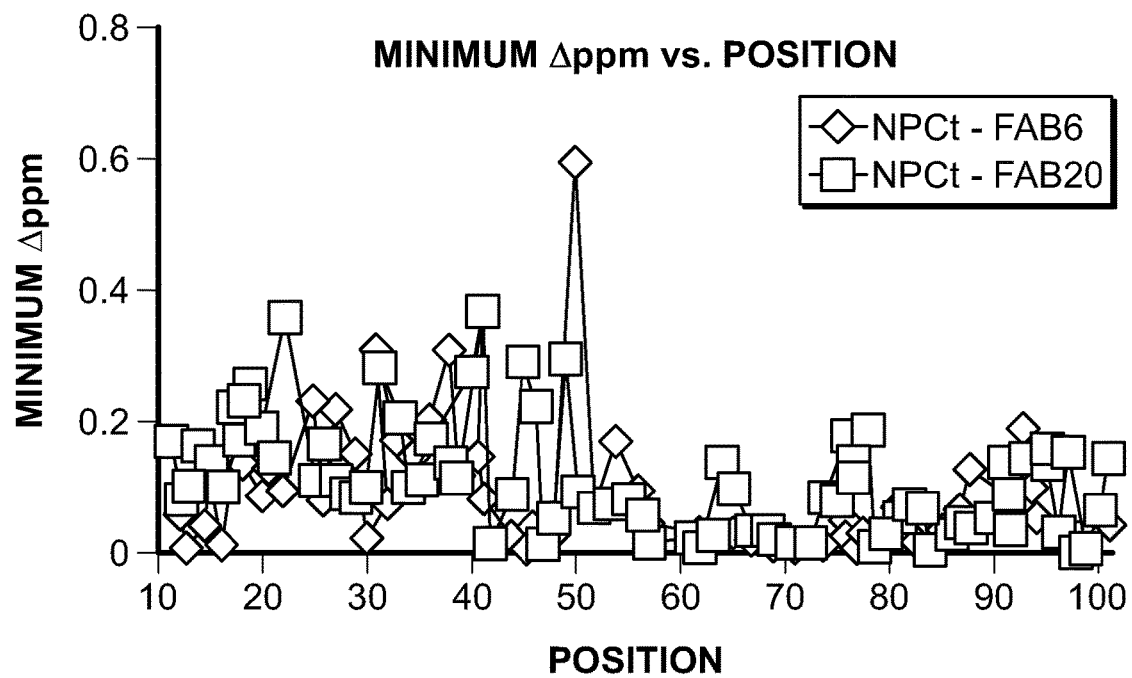
FIG. 5B is a graph showing the estimated shift in the peaks of the Fab 6 (♦) and Fab 20 (■) complexes along the amino acid sequence.
Figure 5C:
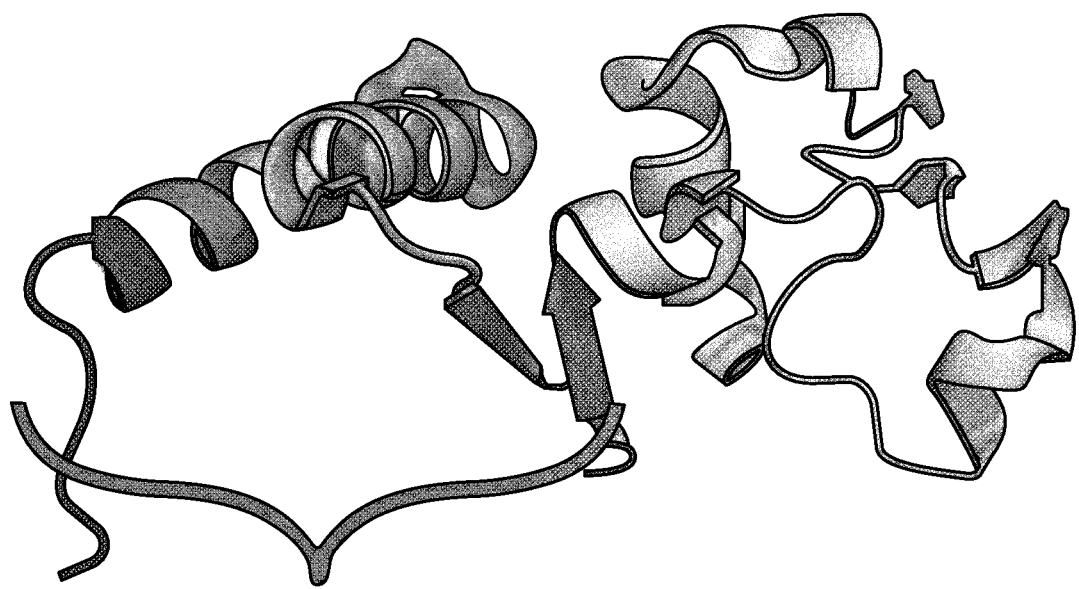
FIG. 5C is a representative tertiary protein structure of the predicted binding epitopes of Fab 6 and Fab 20.

Example 10: Structural Characterization of Fab Binding to $NP^{Ct}$ of Zaire EBOV The structural characterization of the interaction of each Fab antibody with Zaire $NP^{Ct}$ was determined using heteronuclear NMR. $^{15}$N-labeled $NP^{Ct}$ samples, alone and in the presence of each of Fab6 and Fab20, were used to record $^{1}$H-$^{15}$N HSQC spectra, where only the Zaire $NP^{Ct}$ was isotopically labeled (see FIG. 5). For example, FIG. 5A shows a graph with NMR data results of a fragment of $^{1}$H-$^{15}$N HSQC overlaid spectra of free $NP^{Ct}$ with backbone amide assignments (green), a $NP^{Ct}$ complex with Fab20 (red), and a $NP^{Ct}$ complex with Fab6 (blue). In the spectra of complexes the peaks nearest the assigned peak for free $NP^{Ct}$ is assumed to correspond to the same amide (e.g., a black arrow). FIG. 5B shows a graphical comparison of the estimates of the shifts in the peaks of the Fab6 and Fab20 complexes along the $NP^{Ct}$ amino acid sequence. Based on these analyses, FIG. 5C shows a putative crystal structure of the most likely topological location of the antibody-interacting epitopes for both Fab6 and Fab20. This experiment confirmed that both Fab6 and Fab20 most likely bind to the N-terminal helical hairpin and the first β-hairpin of the C-terminal end of Nucleoprotein (NP$^{Ct}$).

Figure 6A:
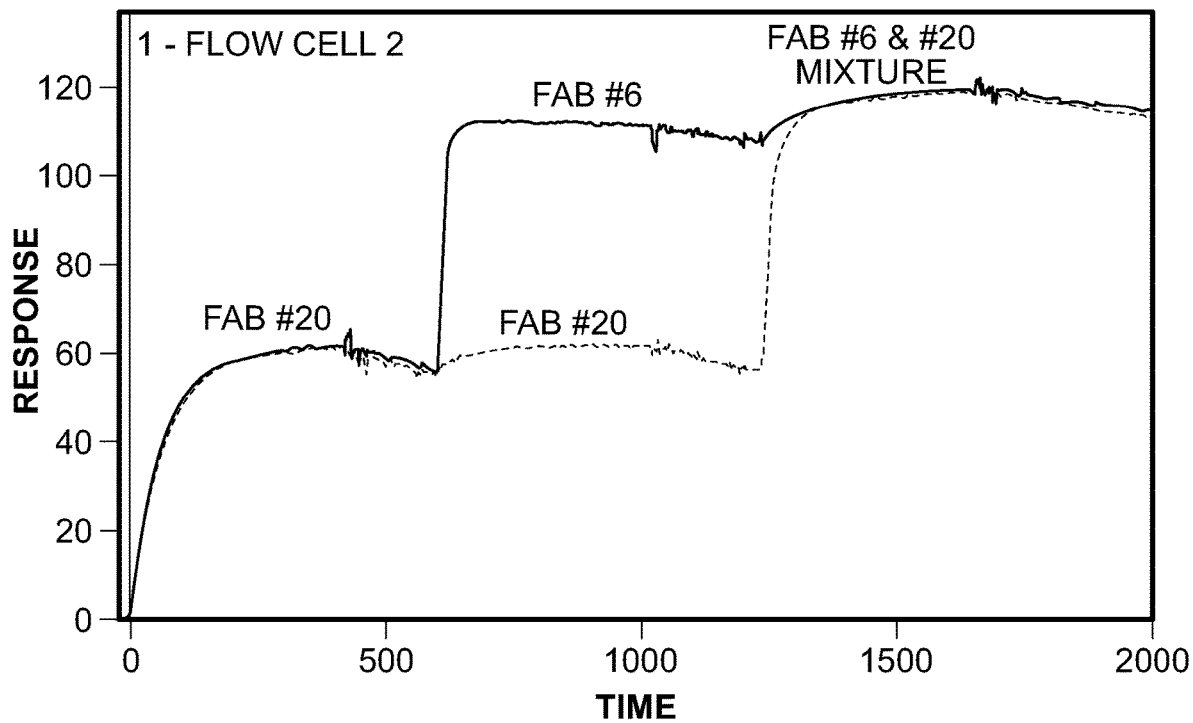
FIG. 6A is a graph showing the epitope mapping patterns of a mixture of Fab 6 and Fab 20.
Figure 6B:
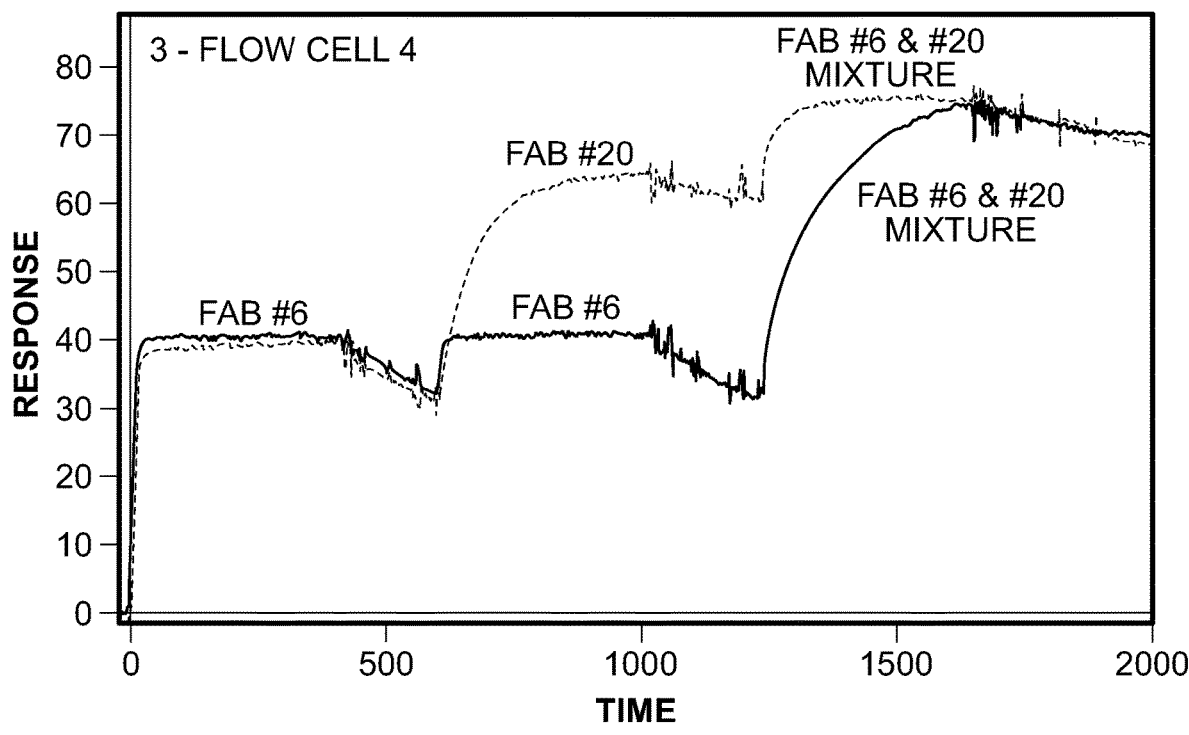
FIG. 6B is a graph showing the epitope mapping patterns of a mixture of Fab 6 and Fab 20.
Figure 7A:
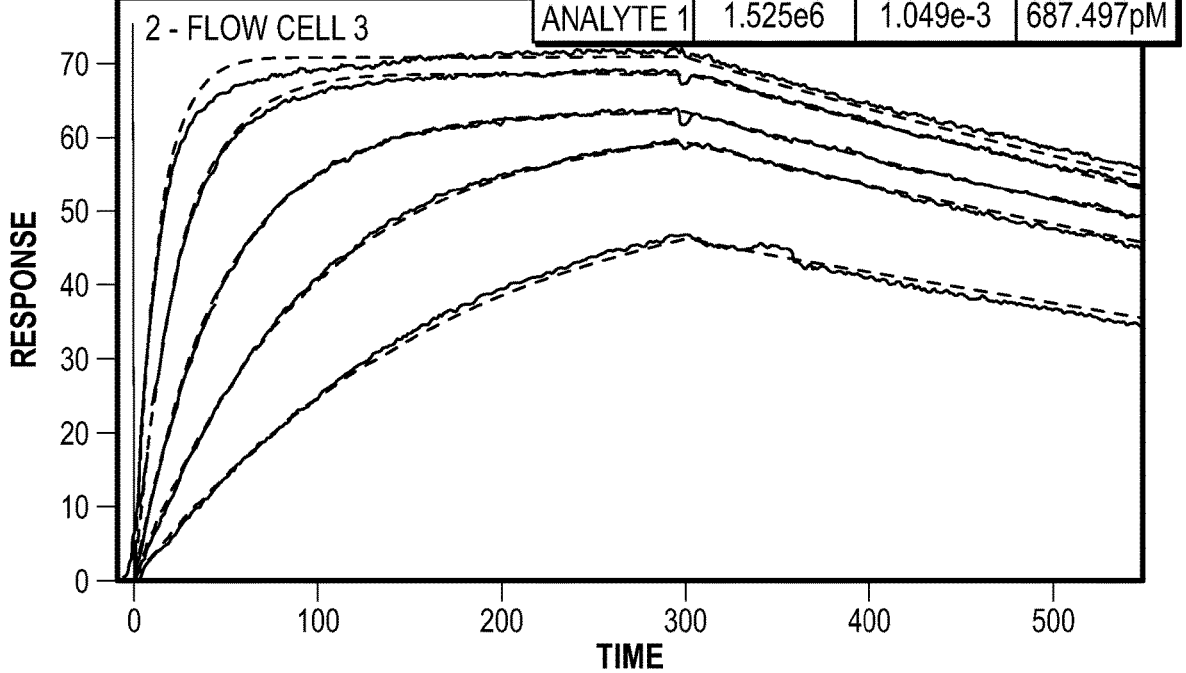
FIG. 7A is a graph showing the epitope binding affinity of Fab 6 to Zaire EBOV NP$^{Ct}$.
Figure 7B:
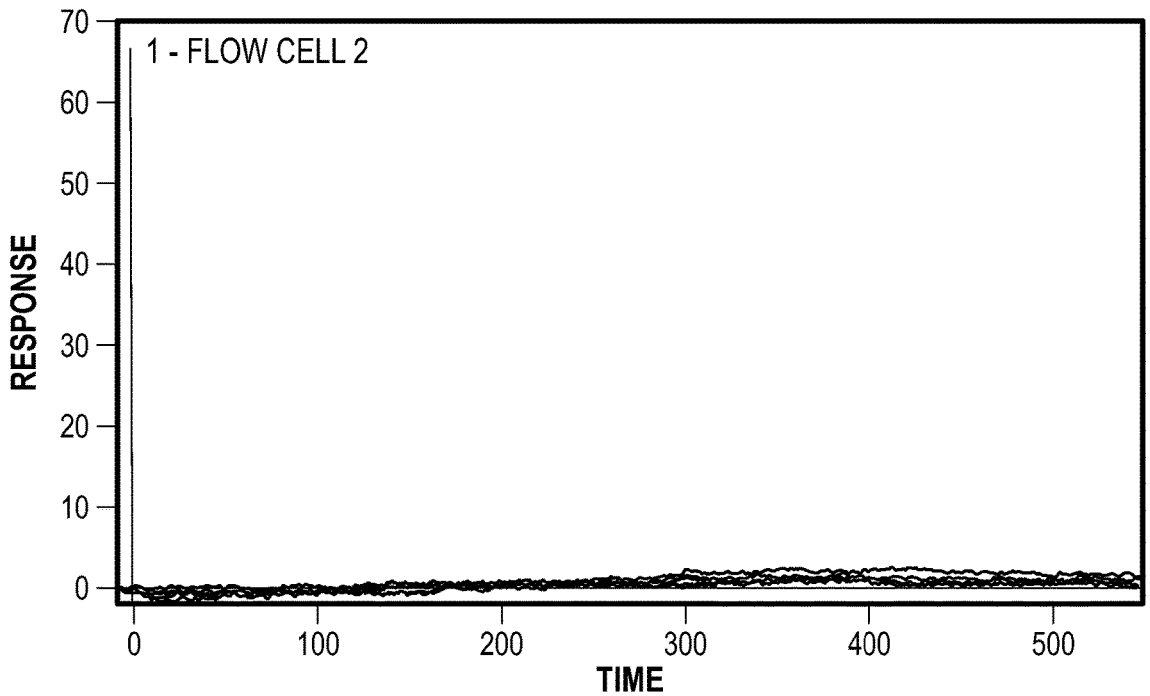
FIG. 7B is a graph showing the epitope binding affinity of Fab 6 to Reston EBOV NP$^{Ct}$.
Figure 7C:
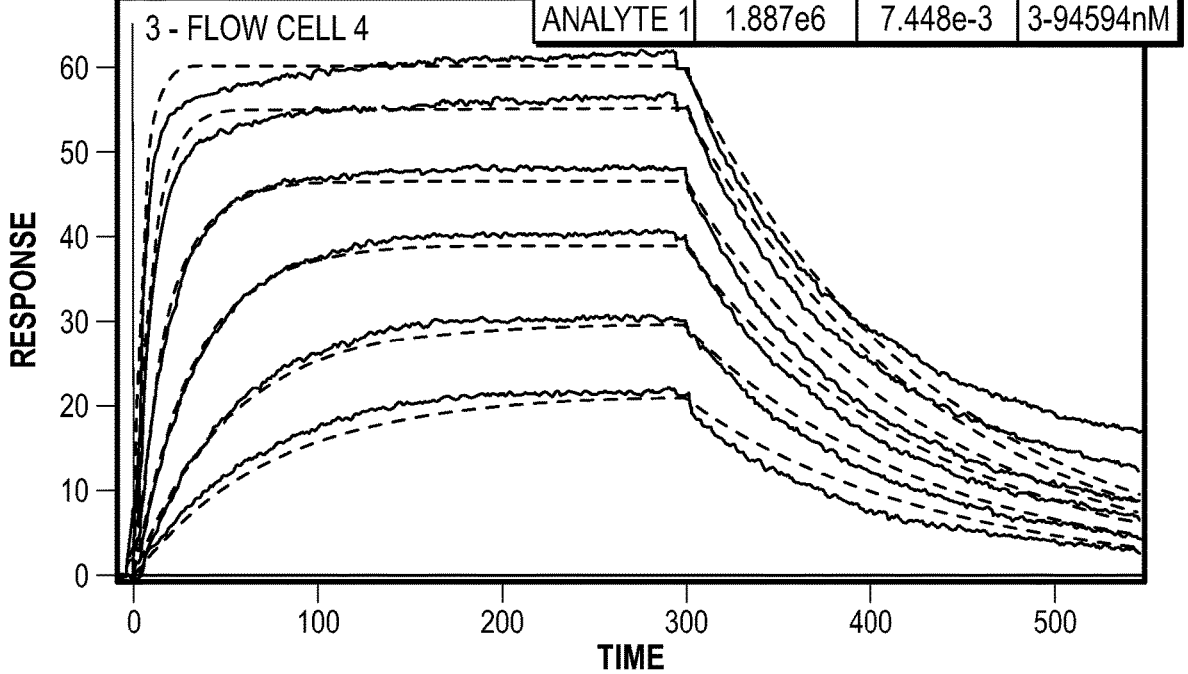
FIG. 7C is a graph showing the epitope binding affinity of Fab 6 to Bundibugyo EBOV NP$^{Ct}$.
Figure 7D:
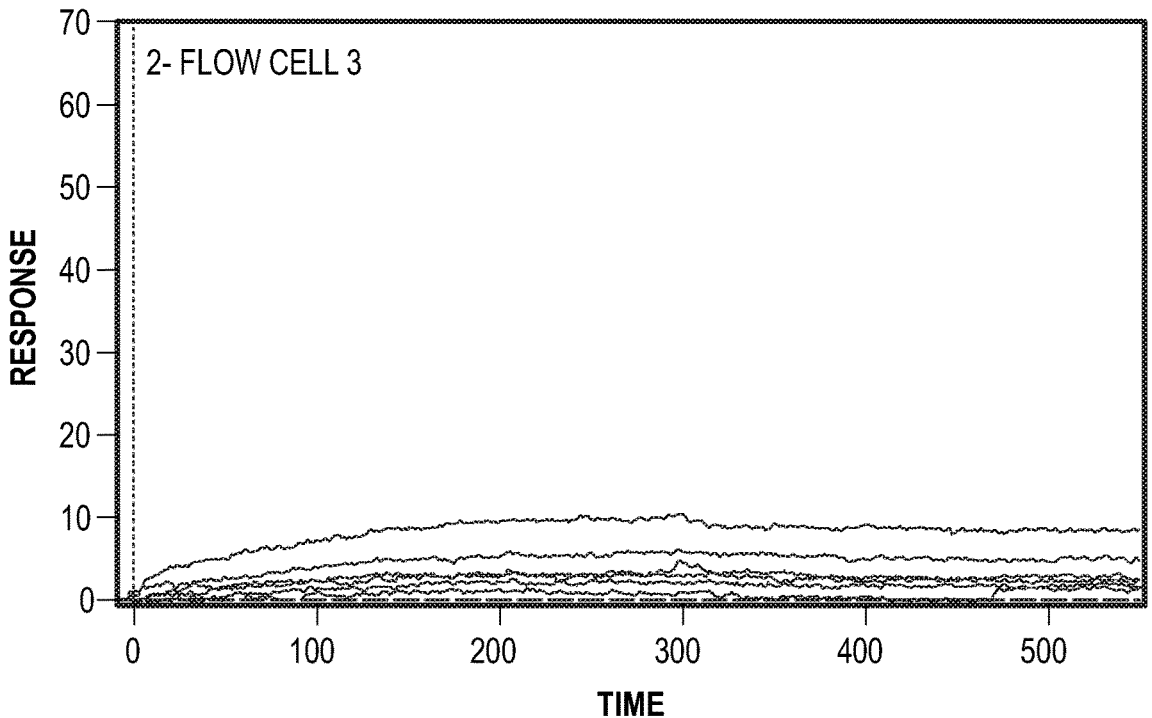
FIG. 7D is a graph showing the epitope binding affinity of Fab 6 to Sudan EBOV NP$^{Ct}$.
Figure 7E:
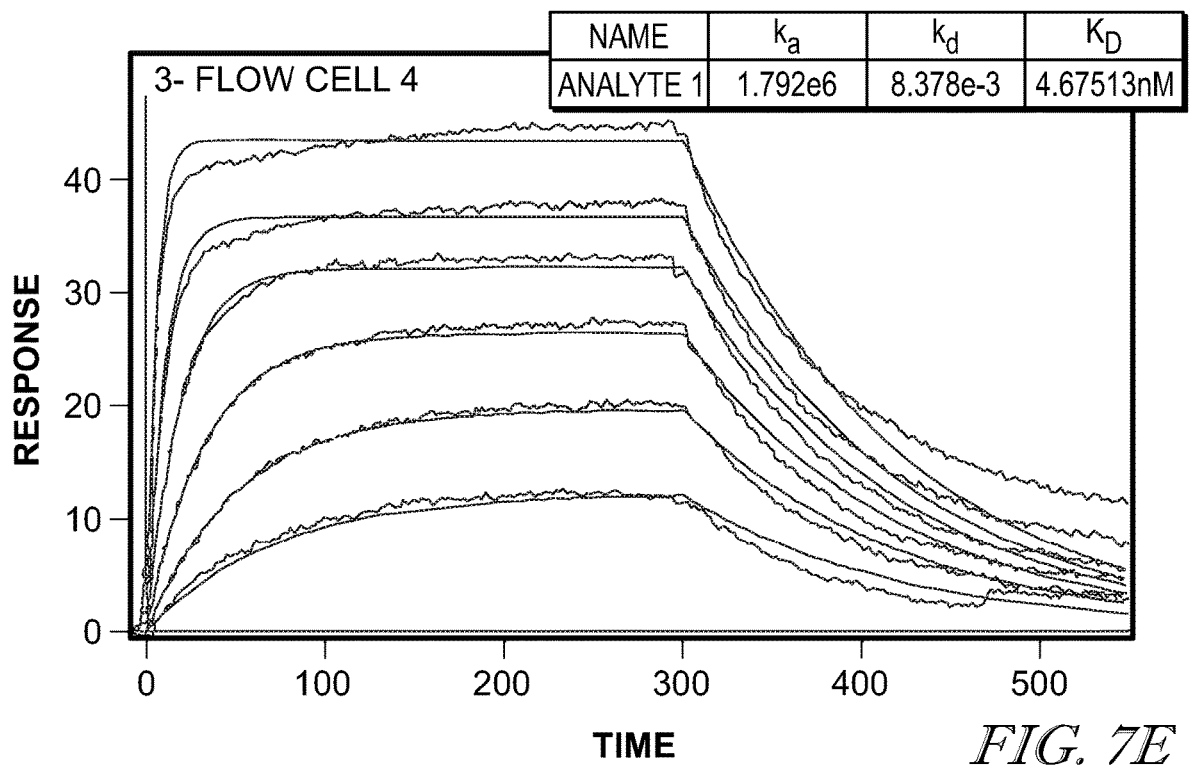
FIG. 7E is a graph showing the epitope binding affinity of Fab 6 to Tai Forest EBOV NP$^{Ct}$.
Figure 7F:
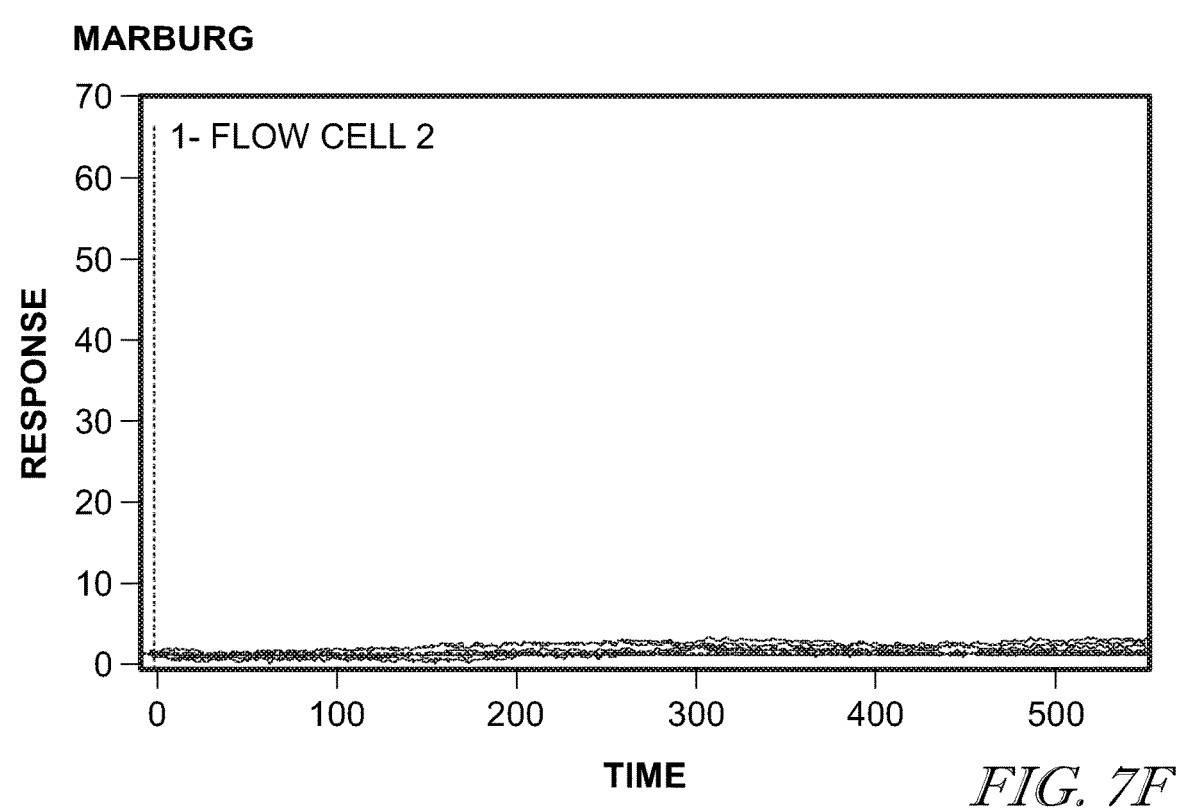
FIG. 7F is a graph showing the epitope binding affinity of Fab 6 to Marburg EBOV NP$^{Ct}$.

Example 11: Fab Binding Affinity for the NP$^{Ct}$ Domain from the Zaire EBOV Fab6 and Fab20 were then tested using Surface Plasmon Resonance (SPR), as described in Example 1, to determine whether they have a high binding affinity for the Zaire Nucleoprotein (see FIGS. 6-8). As shown in FIG. 6. a mixture of Fab6 and Fab20 were analyzed. The figures demonstrate Fab6 and Fab20 have high affinity for the target antigen. Furthermore, Fab6 and Fab20 do not compete with one another for binding to Zaire Nucleoprotein, but rather produce an additive effect (see FIG. 6b) when Fab6 and Fab20 are mixed, indicating that the two antibodies bind to independent sites on the Zaire Nucleoprotein. In addition, the affinity of Fab 6 and Fab 20 to bind to the NP$^{Ct}$ of each of the 5 EBOV strains was also tested (see FIGS. 7 and 8). In particular, FIGS. 7A-7E show the ability of Fab 6 to bind to the NP$^{Ct}$ of the Zaire, Reston, Bundibugyo, Sudan, Tai Forest EBOV strains, respectively. FIG. 7F shows the ability of Fab 6 to bind to the NP$^{Ct}$ of the Marburg virus.

Figure 8A:
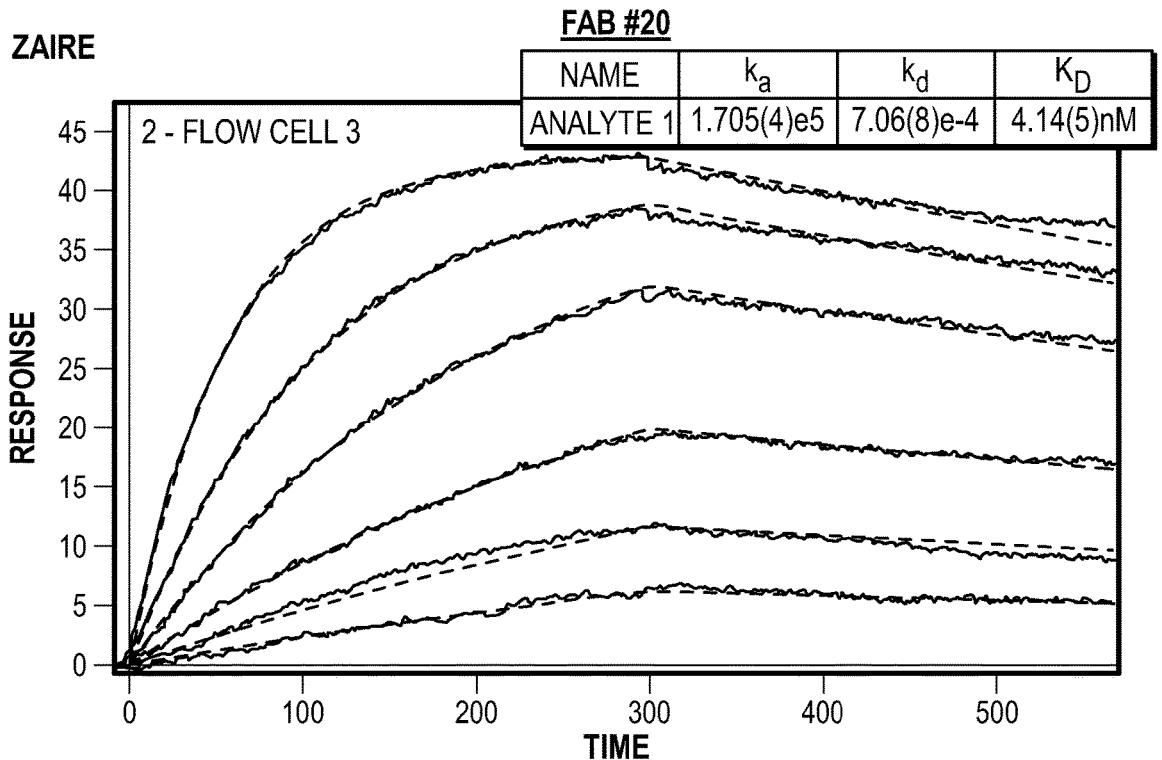
FIG. 8A is a graph showing the epitope binding affinity of Fab 20 to Zaire EBOV NP$^{Ct}$.
Figure 8B:
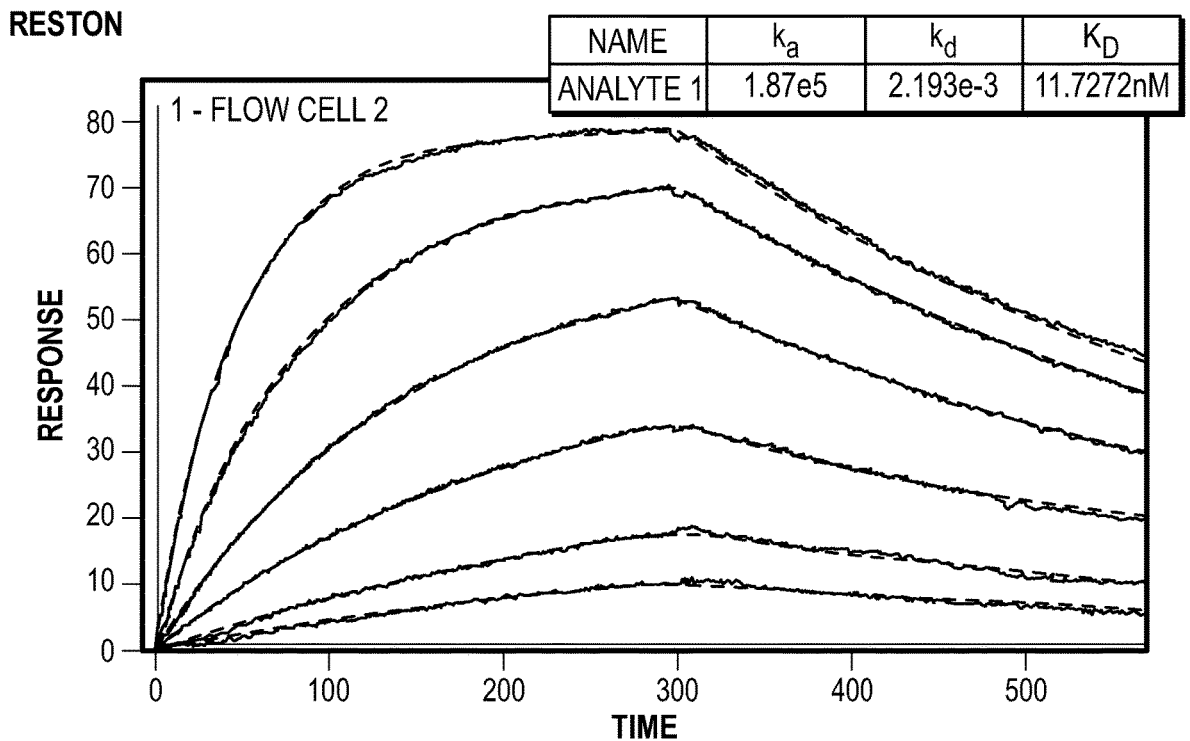
FIG. 8B is a graph showing the epitope binding affinity of Fab 20 to Reston EBOV NP$^{Ct}$.
Figure 8C:
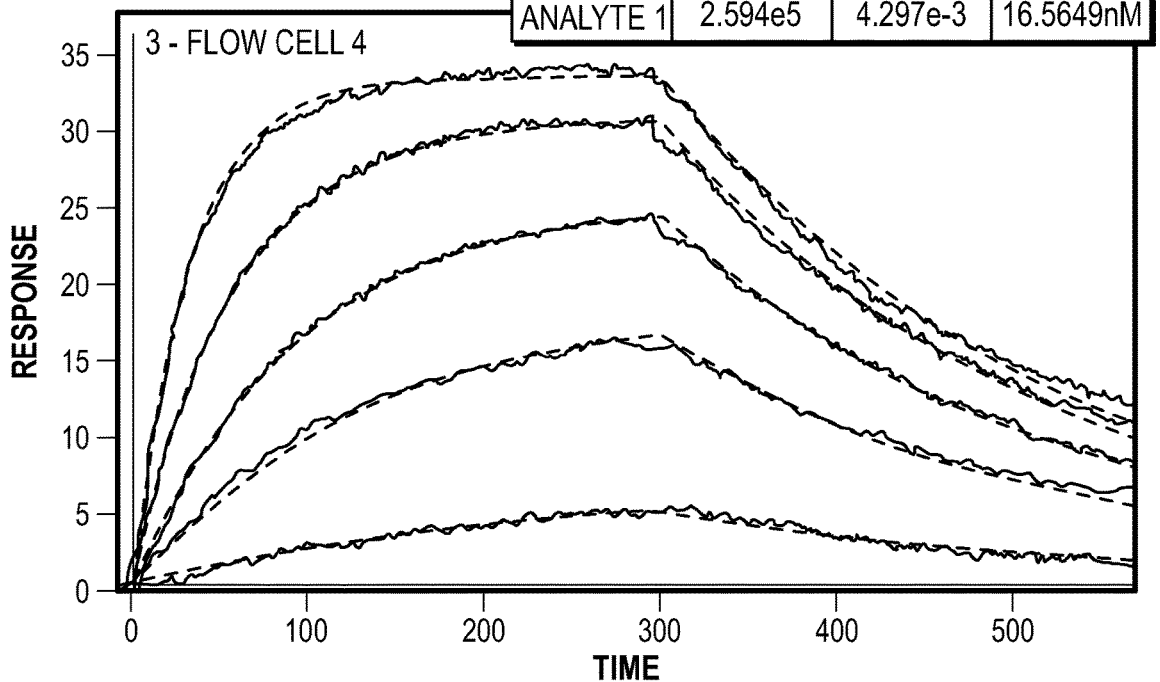
FIG. 8C is a graph showing the epitope binding affinity of Fab 20 to Bundibugyo EBOV NP$^{Ct}$.
Figure 8D:
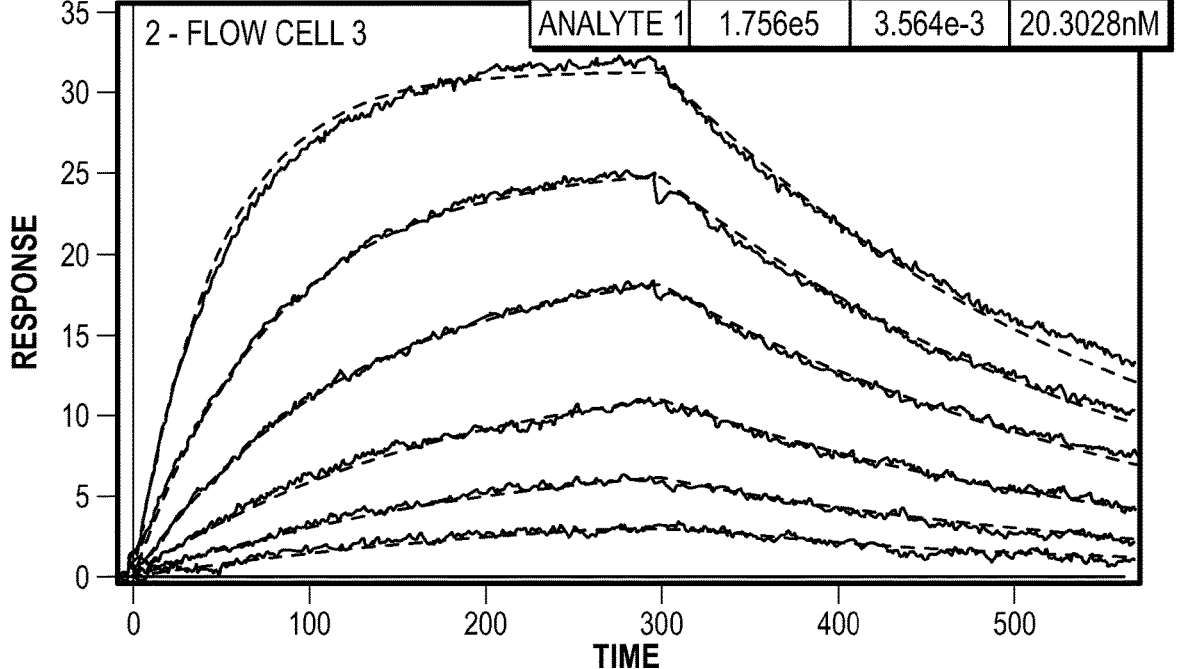
FIG. 8D is a graph showing the epitope binding affinity of Fab 20 to Sudan EBOV NP$^{Ct}$.
Figure 8E:
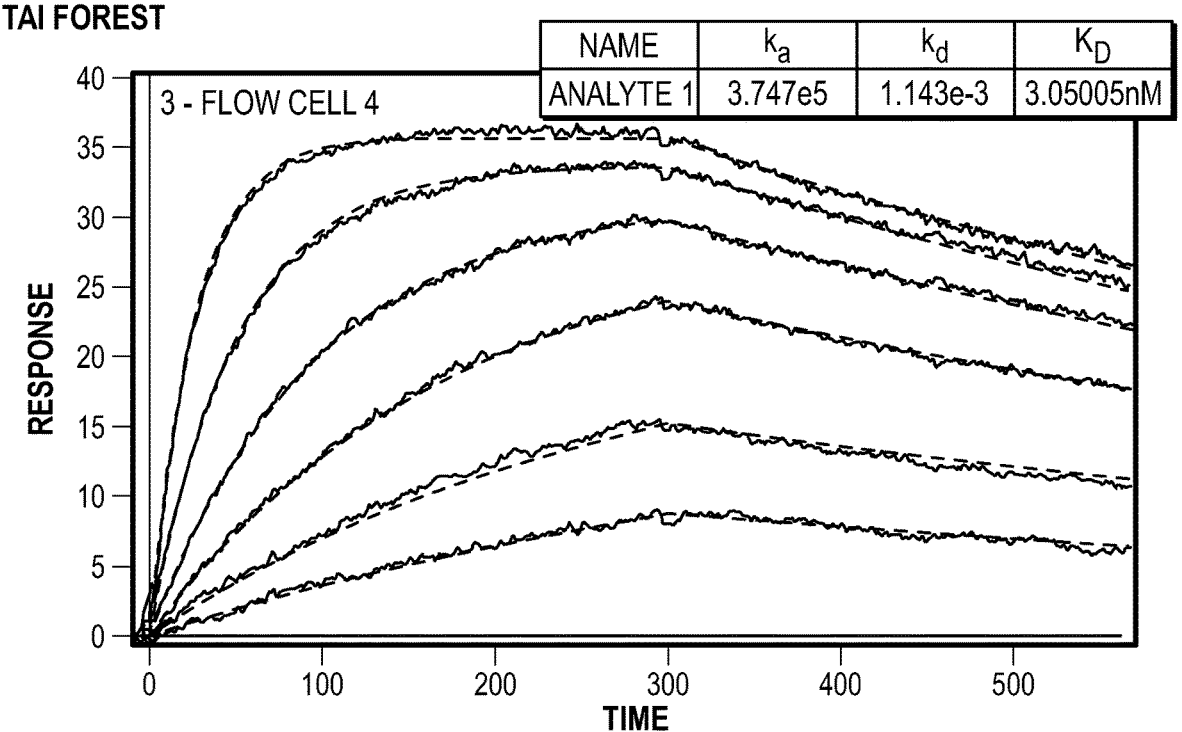
FIG. 8E is a graph showing the epitope binding affinity of Fab 20 to Tai Forest EBOV NP$^{Ct}$.
Figure 8F:
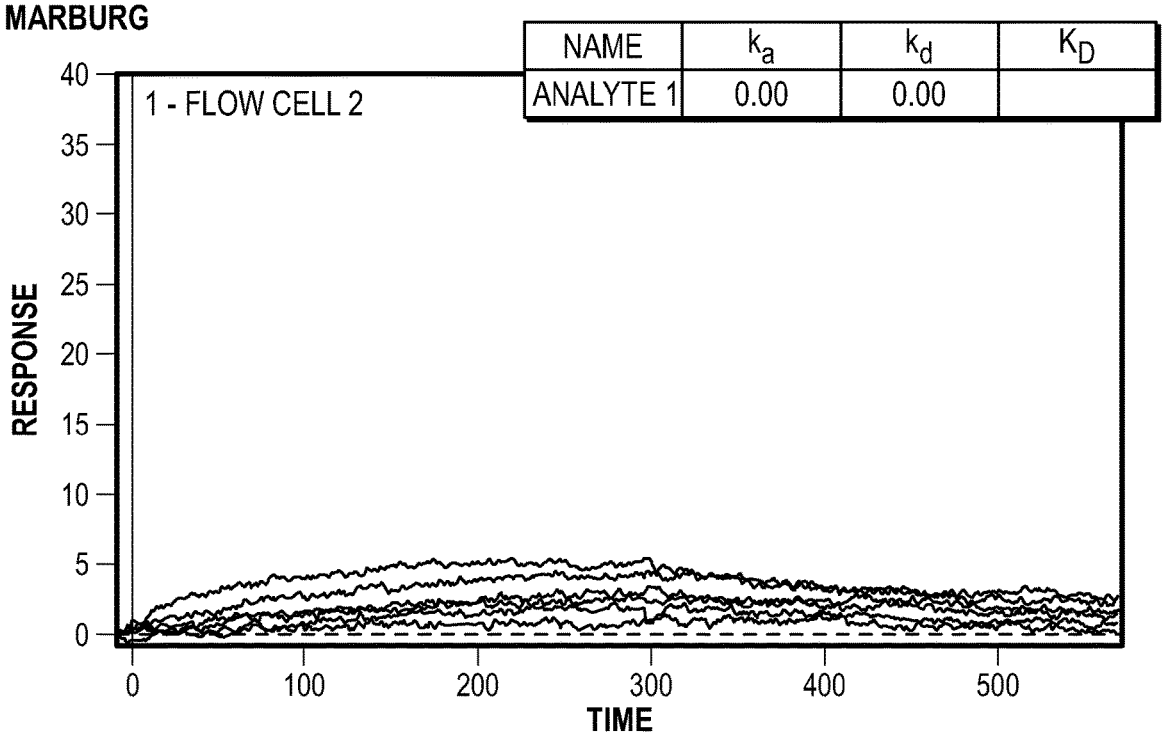
FIG. 8F is a graph showing the epitope binding affinity of Fab 20 to Marburg EBOV NP$^{Ct}$.

Similarly, FIGS. 8A-8E show the ability of Fab 20 to bind to the NP$^{Ct}$ of the Zaire, Reston, Bundibugyo, Sudan, Tai Forest EBOV strains, respectively. FIG. 8F shows the ability of Fab 20 to bind to the NP$^{Ct}$ of the Marburg virus. These data confirm that both Fab6 and Fab20 have higher binding affinity for the Zaire Nucleoprotein than any other strain of filovirus that affect humans. Notably, Fab 20 binding affinity to the Reston strain of EBOV (see FIG. 8B) was higher than that shown for the Zaire strain of EBOV (see FIG. 8A). However, the Reston viral strain of EBOV is believed to date to not infect humans.

Example 12: Analysis of Fab Binding to Tertiary Structure of Zaire EBOV NP$^{Ct}$ Diffracting crystals of the Zaire NP$^{Ct}$ complex with Fab20 were obtained. Preliminary data were collected to 3.2 Å (at SER-CAT beamline at Argonne National Laboratory, Chicago, Ill.), and a tentative model was obtained using molecular replacement with three independent search moieties, including the Fab variable domain, the constant domain, and the Zaire NP$^{Ct}$. Importantly, the putative epitope on the NP$^{Ct}$ is located exactly where the NMR data identified a binding surface or patch.

X-ray crystallography data was processed to 2.6 Å resolution and carried out via some partial refinement of the model, such that the current R and R-free factors for a model that lacks all of the CDR loops are 0.30 and 0.41, respectively. Based on all of this information, a putative crystal structure characterization of the NP$^{Ct}$/Fab20 complex was prepared.

Example 13: Amino Acid Sequence Characterization of Fab20

FIG. 9 is an illustrative embodiment of the Fab20 antibody amino acid sequence. The Fab20 heavy chain (see FIG. 9A) and light chain (see FIG. 9B) amino acids of the present disclosure comprise SEQ ID NO: 212 and SEQ ID NO: 213, respectively. Illustrative embodiments of the CDRS of Fab20 include, but are not limited to the following: 1) ISYSSI (SEQ ID NO: 43), 2) SIYSYSGYTS (SEQ ID NO: 96), 3) SYWYHVGSWHYTGM (SEQ ID NO: 145), and 4) SSSSLI (SEQ ID NO: 35). More specifically, illustrative embodiments of the CDRS of the Fab20 heavy chain sequence (see FIG. 9A) include, but are not limited to the following: 1) ISYSSI (SEQ ID NO: 43), 2) SIYSYSGYTS (SEQ ID NO: 96), and 3) SYWYHVGSWHYTGM (SEQ ID NO: 145). In addition, illustrative embodiments of the CDRS of the Fab20 light chain sequence (see FIG. 9B) include, but are not limited to SSSSLI (SEQ ID NO: 35).

Example 14: Amino Acid Sequence Characterization of Fab6

FIG. 10 is an illustrative embodiment of the Fab6 antibody amino acid sequence. The Fab6 heavy chain (see FIG. 10A) and light chain (see FIG. 10B) amino acids of the present disclosure comprise SEQ ID NO: 210 and SEQ ID NO: 211, respectively. Illustrative embodiments of the CDRs of Fab6 include, but are not limited to the following: 1) VYYYYI (SEQ ID NO: 105), 2) SISPYYGYTS (SEQ ID NO: 51), 3) WSYDQSMSYKSGM (SEQ ID NO: 104), AND 4) YSYSLV (SEQ ID NO: 106).

More specifically, illustrative embodiments of the CDRs of the Fab6 heavy chain sequence (see FIG. 10A) include, but are not limited to the following: 1) VYYYYI (SEQ ID NO: 105), 2) SISPYYGYTS (SEQ ID NO: 51), 3) WSYDQSMSYKSGM (SEQ ID NO: 104). In addition, illustrative embodiments of the CDRs of the Fab6 light chain sequence (see FIG. 10B) include, but are not limited to YSYSLV (SEQ ID NO: 106).

CONCLUSION

The present disclosure demonstrates for the first time that the Nucleoprotein of the Ebola viruses contain two distinct globular domains (i.e., the C-terminal and N-terminal domains) that may be produced in E. coli in a recombinant form. The N-terminal domain of the Nucleoprotein (NP$^{Nt}$) is within the stretch of amino acid residues ranging from about 1-412. The second globular domain is located at the C-terminal end of the Nucleoprotein (NP$^{Ct}$) within the stretch of amino acid residues ranging from about 641-739. NMR and X-ray crystallography data of the crystal structures confirmed that a fragment encompassing NP$^{Ct}$ is completely folded. In fact, crystal structures obtained for two distinct forms of this NP$^{Ct}$ domain revealed a novel fold, with a topology distantly related to some members of the β-grasp superfamily.

An intriguing aspect of EBOV NP$^{Ct}$ is that it has relatively low amino acid sequence conservation among the five strains or subtypes of EBOV, and even less when compared with proteins from LLOV and MARV. This is surprising given that the NP$^{Ct}$ has been implicated in several protein-protein interactions involving other EBOV proteins, so a significantly higher conservation of solvent-exposed residues might be expected. Future studies will specify how the high sequence variation of the EBOV NP$^{Ct}$ impacts on the protein contact interactions.

The biochemistry of the EBOV NP revealed the distinct two-domain architecture of the Nucleoprotein, and provided visualization in atomic detail of the structure of the C-terminal domain (see FIG. 1). This globular domains is the most diverse protein domain of the EBOV genome among the five strains (see FIG. 1). Crystal structures of the proteins from the Tai Forest and Bundibugyo EBOV strains were also prepared (data not shown). Thus, the C-terminal domain is particularly suited as a bait or epitope for strain-selective Fabs. Further, the structure and sequence of this C-terminal domain are unlike any protein in the human genome, and the probability of cross-reactivity of Fabs raised against this domain with any human protein is minimal.

Thus, the NP$^{Ct}$ is an ideal target of a diagnostic antibody, particularly a canonical polyclonal antibody that should be (a) highly immunogenic, (b) abundant in the tested sample, and (c) distinct from any endogenous material in order to reduce the incidence of false positive results. As described herein, the existing diagnostic tests to identify EBOV utilize the VP40 protein as an antigen. The present disclosure is directed to antibodies comprising the nucleoprotein (NP) as a better option.

For example, while VP40 is the most abundant protein in the mature virion, NP is the most abundant viral protein in the infected cells, because its gene is located at the 3'-end (see FIG. 1). It is the concentration of NP that determines the timing of the switch from gene transcription to genome replication. As described herein, it has been determined that NP is detectable by an ELISA assay in the plasma and blood of humans and animals (e.g., monkeys) infected with EBOV.

However, a benefit of the Fab antibodies of the present disclosure is that virtually any antigen present in the blood or plasma of a subject or patient can be used to obtain specific Fabs with high affinity ($K_D$ in the ~nM range) and high selectivity for EBOV detection. In addition, Fabs of the present disclosure are based on the well characterized Herceptin® template, an FDA approved biologic.

The invention described herein incorporates an in vitro phage display system, rather than canonical animal immunization, so the issue of immunogenicity is irrelevant and/or inapplicable. In addition, recombinant products can be obtained using bacterial E. coli expression, dramatically reducing the cost of Fab antibody generation. The Fabs obtained through the phage-display screening protocol can also be engineered for enhanced sensitivity, selectivity, and/or stability using protein engineering approaches based on the structure of complexes with antigens. For example, the recombinant Fabs are stable, and can be lyophilized and deployed by adding water. Thus, large stockpiles of Fabs can be maintained at low cost, and additional amounts can be produced within very short periods of time (e.g., within days).

However, as the synthetic Fabs of the present disclosure recognize specific protein conformations, it is important to note that the NP$^{Ct}$ has a unique tertiary structure, not observed among any eukaryotic proteins. Thus, there is also an increase in specificity of the Fab antibodies described herein over prior art polyclonal antibodies. In addition, recombinant Fabs can be coupled to various detection schemes (e.g., light or radiation emitting imaging methods), further enhancing sensitivity.

Various modification and variation of the described methods and compositions of the present application will be apparent to those skilled in the art without departing from the scope and spirit of the present application. Although the present application has been described in connection with specific preferred embodiments, it should be understood that the present application as claimed should not be unduly limited to such specific embodiments. Indeed, various modifications of the described modes for carrying out the present application that are obvious to those skilled in the relevant fields are intended to be within the scope of the following claims.

The invention claimed is:

1. An antibody that specifically binds to the C-terminal domain of the Nucleoprotein of Ebola virus, wherein the heavy chain of said antibody comprises the following complementarity determining region (CDR) sequences:
SEQ ID NO: 43, SEQ ID NO: 96, and SEQ ID NO: 145; and the light chain of said antibody comprises the amino acid sequence of SEQ ID NO: 213.

2. The antibody of claim 1, wherein the antibody is a monoclonal antibody.

3. The antibody of claim 1, wherein the antibody is a chimeric antibody.

4. The antibody of claim 1, wherein the antibody is a fragment binding protein (Fab).

5. The antibody of claim 1, wherein the antibody is expressed as a recombinant antibody having a variant Fc domain.

6. An antibody that specifically binds to the C-terminal domain of the Nucleoprotein of an Ebola virus strain selected from the group consisting of Tai Forest, Sudan, Bundibugyo, Reston, and Zaire, said antibody comprising
a heavy chain amino acid sequence that comprises the complementarity determining region (CDR) sequences of SEQ ID NO: 145, SEQ ID NO: 43, and SEQ ID NO: 96 and
a light chain amino acid sequence of SEQ ID NO: 213.

7. The antibody of claim 1, wherein said antibody binds an amino acid sequence selected from the group consisting of SEQ ID NO: 1, SEQ ID NO: 2, SEQ ID NO: 3, SEQ ID NO: 4, and SEQ ID NO: 5.

8. The antibody of claim 1, wherein the antibody comprises a heavy chain of SEQ ID NO: 212 and a light chain of SEQ ID NO: 213.

9. An antibody that specifically binds to the C-terminal domain of the Nucleoprotein of an Ebola virus strain, wherein the antibody is a Fab fragment consisting of a heavy chain sequence of SEQ ID NO: 212 and a light chain of SEQ ID NO: 213.

10. The antibody of claim 9, wherein the antibody is labeled with a detectable moiety.

11. A pharmaceutical composition comprising the antibody of claim 1, and a pharmaceutically acceptable carrier, excipient, or diluent.

12. The antibody of claim 1, wherein the antibody is labeled with a detectable moiety.

* * * * *